(12) United States Patent
Oberoi et al.

(10) Patent No.: US 11,327,071 B2
(45) Date of Patent: *May 10, 2022

(54) ASSESSMENT OF PREECLAMPSIA USING ASSAYS FOR FREE AND DISSOCIATED PLACENTAL GROWTH FACTOR

(71) Applicant: Progenity, Inc., San Diego, CA (US)

(72) Inventors: Pankaj Oberoi, Rockville, MD (US); Sharat Singh, Rancho Santa Fe, CA (US); Amin Mazloom, Del Mar, CA (US)

(73) Assignee: PROGENITY, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/393,708

(22) Filed: Aug. 4, 2021

(65) Prior Publication Data

US 2021/0373001 A1 Dec. 2, 2021

Related U.S. Application Data

(63) Continuation of application No. 17/119,410, filed on Dec. 11, 2020, now Pat. No. 11,112,403, which is a continuation of application No. PCT/US2020/063408, filed on Dec. 4, 2020.

(60) Provisional application No. 62/947,957, filed on Dec. 13, 2019, provisional application No. 62/943,739, filed on Dec. 4, 2019.

(51) Int. Cl.
G01N 33/537 (2006.01)
G01N 33/68 (2006.01)
G01N 33/74 (2006.01)

(52) U.S. Cl.
CPC ....... *G01N 33/5375* (2013.01); *G01N 33/689* (2013.01); *G01N 33/6863* (2013.01); *G01N 33/74* (2013.01); *G01N 2800/368* (2013.01); *G01N 2800/50* (2013.01)

(58) Field of Classification Search
None
See application file for complete search history.

(56) References Cited

U.S. PATENT DOCUMENTS

| | | |
|---|---|---|
| 4,777,964 A | 10/1988 | Briggs et al. |
| 4,919,889 A | 4/1990 | Jones et al. |
| 5,096,830 A | 3/1992 | Senyei et al. |
| 5,223,440 A | 6/1993 | Teng et al. |
| 5,281,522 A | 1/1994 | Senyei et al. |
| 5,431,171 A | 7/1995 | Harrison et al. |
| 5,468,619 A | 11/1995 | Senyei et al. |
| 5,516,702 A | 5/1996 | Senyei et al. |
| 5,597,700 A | 1/1997 | Konstantinov et al. |
| 5,616,719 A | 4/1997 | Davalian et al. |
| 5,641,636 A | 6/1997 | Strauss, III et al. |
| 5,650,394 A | 7/1997 | Terao et al. |
| 5,698,404 A | 12/1997 | Strauss, III et al. |
| 5,783,396 A | 7/1998 | Voroteliak et al. |
| 5,807,675 A | 9/1998 | Davalian et al. |
| 5,861,319 A | 1/1999 | Lin et al. |
| 5,877,029 A | 3/1999 | Fuks et al. |
| 5,891,722 A | 4/1999 | Fuks et al. |
| 5,898,005 A | 4/1999 | Singh et al. |
| 5,968,758 A | 10/1999 | Fuks et al. |
| 6,126,597 A | 10/2000 | Smith et al. |
| 6,126,616 A | 10/2000 | Sanyal |
| 6,140,099 A | 10/2000 | Strauss, III et al. |
| 6,149,590 A | 11/2000 | Smith et al. |
| 6,267,722 B1 | 7/2001 | Anderson et al. |
| 6,312,393 B1 | 11/2001 | Abreu et al. |
| 6,394,952 B1 | 5/2002 | Anderson et al. |
| 6,395,499 B1 | 5/2002 | Abramovitz et al. |
| 6,410,583 B1 | 6/2002 | Labelle et al. |
| 6,544,193 B2 | 4/2003 | Abreu et al. |
| 6,556,977 B1 | 4/2003 | Lapointe et al. |
| 6,605,705 B1 | 8/2003 | Oda et al. |
| 6,610,480 B1 | 8/2003 | Shimkets et al. |
| 6,678,669 B2 | 1/2004 | Lapointe et al. |
| 6,790,635 B1 | 9/2004 | Seiki et al. |
| 6,867,051 B1 | 3/2005 | Anderson et al. |
| 6,875,567 B1 | 4/2005 | Shimkets et al. |
| 6,878,522 B2 | 4/2005 | Li et al. |
| 6,884,593 B1 | 4/2005 | Hirai et al. |
| 6,936,476 B1 | 8/2005 | Anderson et al. |
| 7,041,063 B2 | 5/2006 | Abreu et al. |
| 7,083,940 B2 | 8/2006 | Oxvig et al. |
| 7,109,044 B1 | 9/2006 | Oda et al. |
| 7,144,913 B2 | 12/2006 | Wang et al. |

(Continued)

FOREIGN PATENT DOCUMENTS

| | | |
|---|---|---|
| EP | 0913405 A1 | 5/1999 |
| EP | 1575416 A2 | 9/2005 |

(Continued)

OTHER PUBLICATIONS

Moore et al., The Journal of Maternal-Fetal and Neonatal Medicine, 2012; 25(12): 2651-2657 (Year: 2012).*
Peter Hornbeck, Current Protocols in Immunology (1991) 2.1.1-2.1.22 (Year: 1991).*
Radelescu et al., Mediators of Inflammation vol. 2016, Article ID 3027363, 8 pages; http://dx.doi.org/10.I 155/2016/3027363 (Year: 2016).*

(Continued)

*Primary Examiner* — Christina M Borgeest
(74) *Attorney, Agent, or Firm* — Wilson Sonsini Goodrich & Rosati

(57) ABSTRACT

Described herein are methods, compositions, kits, and systems for detecting free and bound PlGF, and using detection of such species to distinguish between pregnant women with or without preeclampsia or related conditions.

18 Claims, 17 Drawing Sheets

(56) References Cited

U.S. PATENT DOCUMENTS

| | | |
|---|---|---|
| 7,191,068 B2 | 3/2007 | Rosenfeld et al. |
| 7,217,725 B2 | 5/2007 | Krauss et al. |
| 7,228,295 B2 | 6/2007 | Lapointe et al. |
| 7,270,970 B2 | 9/2007 | Anderson et al. |
| 7,314,727 B2 | 1/2008 | Mase et al. |
| 7,335,362 B2 | 2/2008 | Karumanchi et al. |
| 7,344,892 B2 | 3/2008 | Thadhani et al. |
| 7,399,596 B2 | 7/2008 | Oda et al. |
| 7,403,805 B2 | 7/2008 | Abreu et al. |
| 7,407,659 B2 | 8/2008 | Karumanchi et al. |
| 7,425,419 B2 | 9/2008 | Poston et al. |
| 7,435,419 B2 | 10/2008 | Karumanchi et al. |
| 7,445,940 B2 | 11/2008 | Caniggia et al. |
| 7,488,585 B2 | 2/2009 | Meiri et al. |
| 7,517,889 B2 | 4/2009 | Harris et al. |
| 7,524,636 B2 | 4/2009 | Bryant-Greenwood et al. |
| 7,528,133 B1 | 5/2009 | Copland, III et al. |
| 7,582,643 B2 | 9/2009 | Blake et al. |
| 7,635,571 B2 | 12/2009 | Ullman et al. |
| 7,635,757 B2 | 12/2009 | Freeman et al. |
| 7,638,287 B2 | 12/2009 | Poston et al. |
| 7,642,249 B2 | 1/2010 | Langevin et al. |
| 7,654,957 B2 | 2/2010 | Abreu et al. |
| 7,709,272 B2 | 5/2010 | Fuks et al. |
| 7,740,849 B2 | 6/2010 | Karumanchi et al. |
| 7,754,495 B2 | 7/2010 | Caniggia et al. |
| 7,756,559 B2 | 7/2010 | Abreu et al. |
| 7,794,953 B2 | 9/2010 | Pentyala et al. |
| 7,809,417 B2 | 10/2010 | Abreu et al. |
| 7,811,279 B2 | 10/2010 | John et al. |
| 7,846,433 B2 | 12/2010 | Karumanchi et al. |
| 7,863,007 B2 | 1/2011 | Voroteliak et al. |
| 7,902,373 B2 | 3/2011 | Blake et al. |
| 7,935,496 B2 | 5/2011 | Buhimschi et al. |
| 7,943,294 B2 | 5/2011 | Hussa et al. |
| 7,947,449 B2 | 5/2011 | Karumanchi et al. |
| 8,060,195 B2 | 11/2011 | Gurewitsch et al. |
| 8,067,445 B2 | 11/2011 | Hutchinson et al. |
| 8,068,990 B2 | 11/2011 | Rosenfeld et al. |
| 8,071,807 B2 | 12/2011 | Hutchinson et al. |
| 8,114,610 B2 | 2/2012 | Fuks et al. |
| 8,133,859 B2 | 3/2012 | Kimura et al. |
| 8,160,692 B2 | 4/2012 | Principe et al. |
| 8,193,183 B2 | 6/2012 | Lim et al. |
| 8,242,145 B2 | 8/2012 | Hutchinson et al. |
| 8,283,451 B2 | 10/2012 | Poston et al. |
| 8,338,484 B2 | 12/2012 | Hutchinson et al. |
| 8,362,044 B2 | 1/2013 | Hutchinson et al. |
| 8,366,640 B2 | 2/2013 | Bauer et al. |
| 8,372,581 B2 | 2/2013 | Hussa et al. |
| 8,378,107 B2 | 2/2013 | Hutchinson et al. |
| 8,383,654 B2 | 2/2013 | Hutchinson et al. |
| 8,426,449 B2 | 4/2013 | Hutchinson et al. |
| 8,497,381 B2 | 7/2013 | Hutchinson et al. |
| 8,501,688 B2 | 8/2013 | Kimura et al. |
| 8,501,959 B2 | 8/2013 | Hutchinson et al. |
| 8,517,960 B2 | 8/2013 | Bauer et al. |
| 8,518,716 B2 | 8/2013 | Hubel et al. |
| 8,524,748 B2 | 9/2013 | Hutchinson et al. |
| 8,552,154 B2 | 10/2013 | Freeman et al. |
| 8,552,364 B2 | 10/2013 | Graves et al. |
| 8,647,832 B2 | 2/2014 | Cuckle et al. |
| 8,835,183 B2 | 9/2014 | Bashirians et al. |
| 8,871,448 B2 | 10/2014 | Buhimschi et al. |
| 8,932,823 B2 | 1/2015 | Cuckle et al. |
| 8,981,063 B2 | 3/2015 | Chen |
| 9,005,949 B2 | 4/2015 | Oxvig et al. |
| 9,250,251 B2 | 2/2016 | Nicolaides et al. |
| 9,518,992 B2 | 12/2016 | Karumanchi et al. |
| 9,777,315 B2 | 10/2017 | Fredriksson et al. |
| 9,797,903 B2 | 10/2017 | Ragolia |
| 9,797,911 B2 | 10/2017 | Keshet et al. |
| 9,810,695 B2 | 11/2017 | Garovic |
| 9,925,211 B2 | 3/2018 | Karumanchi |
| 9,925,261 B2 | 3/2018 | Karumanchi et al. |
| 10,054,599 B2 | 8/2018 | Lim et al. |
| 10,281,475 B2 | 5/2019 | Chaiworapongsa et al. |
| 10,302,657 B2 | 5/2019 | Denk et al. |
| 10,408,838 B2 | 9/2019 | Ragolia |
| 10,413,591 B2 | 9/2019 | Karumanchi et al. |
| 10,656,163 B2 | 5/2020 | Ahola et al. |
| 11,112,403 B2 | 9/2021 | Oberoi et al. |
| 2001/0023419 A1 | 9/2001 | Lapointe et al. |
| 2001/0025140 A1 | 9/2001 | Torok et al. |
| 2001/0053876 A1 | 12/2001 | Torok et al. |
| 2002/0022218 A1 | 2/2002 | Li et al. |
| 2002/0031513 A1 | 3/2002 | Leibovitz et al. |
| 2002/0046054 A1 | 4/2002 | Morand et al. |
| 2002/0049389 A1 | 4/2002 | Abreu |
| 2003/0004906 A1 | 1/2003 | Lapointe et al. |
| 2003/0027854 A1 | 2/2003 | Arimura et al. |
| 2003/0099651 A1 | 5/2003 | Leibovitz et al. |
| 2003/0105731 A1 | 6/2003 | Lapointe et al. |
| 2003/0113319 A1 | 6/2003 | Leibovitz et al. |
| 2003/0139687 A1 | 7/2003 | Abreu et al. |
| 2003/0190678 A1 | 10/2003 | Mase et al. |
| 2004/0014063 A1 | 1/2004 | Batteux et al. |
| 2004/0038314 A1 | 2/2004 | Oda et al. |
| 2004/0039297 A1 | 2/2004 | Abreu et al. |
| 2004/0039298 A1 | 2/2004 | Abreu et al. |
| 2004/0078219 A1 | 4/2004 | Kaylor et al. |
| 2004/0100376 A1 | 5/2004 | Lye et al. |
| 2004/0157222 A1 | 8/2004 | Smolyar |
| 2004/0162323 A1 | 8/2004 | Krauss et al. |
| 2004/0180934 A1 | 9/2004 | Wang et al. |
| 2004/0185509 A1 | 9/2004 | Gervais et al. |
| 2004/0197834 A1 | 10/2004 | Gervais et al. |
| 2004/0197930 A1 | 10/2004 | Rosenfeld et al. |
| 2004/0241752 A1 | 12/2004 | Anderson et al. |
| 2004/0266025 A1 | 12/2004 | Hickok et al. |
| 2005/0101841 A9 | 5/2005 | Kaylor et al. |
| 2005/0131287 A1 | 6/2005 | Kaylor et al. |
| 2005/0163771 A1 | 7/2005 | Leibovitz et al. |
| 2005/0170444 A1 | 8/2005 | Karumanchi et al. |
| 2005/0215609 A1 | 9/2005 | Yoshikawa et al. |
| 2005/0260683 A1 | 11/2005 | Bryant-Greenwood et al. |
| 2005/0277912 A1 | 12/2005 | John et al. |
| 2006/0008923 A1 | 1/2006 | Anderson et al. |
| 2006/0014302 A1 | 1/2006 | Martinez et al. |
| 2006/0024722 A1 | 2/2006 | Fischer-Colbrie et al. |
| 2006/0024723 A1 | 2/2006 | Hussa et al. |
| 2006/0024724 A1 | 2/2006 | Hussa et al. |
| 2006/0024725 A1 | 2/2006 | Hussa et al. |
| 2006/0024757 A1 | 2/2006 | Hussa et al. |
| 2006/0040337 A1 | 2/2006 | Meiri et al. |
| 2006/0166242 A1 | 7/2006 | Pennell et al. |
| 2006/0166295 A1 | 7/2006 | Woods et al. |
| 2006/0204532 A1 | 9/2006 | John et al. |
| 2006/0240495 A1 | 10/2006 | Buhimschi et al. |
| 2006/0240498 A1 | 10/2006 | Friedman et al. |
| 2007/0003992 A1 | 1/2007 | Pentyala et al. |
| 2007/0016074 A1 | 1/2007 | Abreu et al. |
| 2007/0020609 A1 | 1/2007 | Oda et al. |
| 2007/0054951 A1 | 3/2007 | Li et al. |
| 2007/0128589 A1 | 6/2007 | Sanders et al. |
| 2007/0142718 A1 | 6/2007 | Abreu et al. |
| 2007/0161125 A1 | 7/2007 | Rosenfeld et al. |
| 2007/0196864 A1 | 8/2007 | Pentyala et al. |
| 2007/0244131 A1 | 10/2007 | Lim et al. |
| 2007/0249686 A1 | 10/2007 | Bonnert et al. |
| 2007/0265278 A1 | 11/2007 | Harris et al. |
| 2007/0265291 A1 | 11/2007 | Harris et al. |
| 2008/0009552 A1 | 1/2008 | Pennell et al. |
| 2008/0090759 A1 | 4/2008 | Kokenyesi et al. |
| 2008/0194600 A1 | 8/2008 | Langevin et al. |
| 2008/0227113 A1 | 9/2008 | Pentyala et al. |
| 2008/0233597 A1 | 9/2008 | Shiina et al. |
| 2008/0254479 A1 | 10/2008 | Kokenyesi et al. |
| 2008/0261922 A1 | 10/2008 | Carley et al. |
| 2008/0299594 A1 | 12/2008 | Rosenfeld et al. |
| 2009/0036469 A1 | 2/2009 | Stefany et al. |
| 2009/0036761 A1 | 2/2009 | Abreu et al. |
| 2009/0055099 A1 | 2/2009 | Rosenfeld et al. |
| 2009/0058072 A1 | 3/2009 | Weber et al. |

(56) References Cited

U.S. PATENT DOCUMENTS

| | | |
|---|---|---|
| 2009/0068692 A1 | 3/2009 | Voroteliak et al. |
| 2009/0081206 A1 | 3/2009 | Leibovitz et al. |
| 2009/0171234 A1 | 7/2009 | Gurewitsch et al. |
| 2009/0176247 A1 | 7/2009 | Bashirians et al. |
| 2009/0176804 A1 | 7/2009 | Yang et al. |
| 2009/0197959 A1 | 8/2009 | Hutchinson et al. |
| 2009/0227036 A1 | 9/2009 | Meiri et al. |
| 2009/0299212 A1 | 12/2009 | Principe et al. |
| 2010/0004331 A1 | 1/2010 | Hutchinson et al. |
| 2010/0008911 A1 | 1/2010 | Streisand et al. |
| 2010/0017143 A1 | 1/2010 | Nagalla et al. |
| 2010/0029006 A1 | 2/2010 | Rosenblatt et al. |
| 2010/0075990 A1 | 3/2010 | Endres et al. |
| 2010/0081673 A1 | 4/2010 | Hutchinson et al. |
| 2010/0093621 A1 | 4/2010 | Kimura et al. |
| 2010/0113503 A1 | 5/2010 | Hutchinson et al. |
| 2010/0130574 A1 | 5/2010 | Egg et al. |
| 2010/0145180 A1 | 6/2010 | Abreu et al. |
| 2010/0251394 A1 | 9/2010 | Dore et al. |
| 2010/0298368 A1 | 11/2010 | Stearns et al. |
| 2010/0311190 A1 | 12/2010 | Fuks et al. |
| 2010/0318025 A1 | 12/2010 | John et al. |
| 2010/0323911 A1 | 12/2010 | Devarajan et al. |
| 2010/0330077 A1 | 12/2010 | Armer et al. |
| 2011/0002866 A1 | 1/2011 | Lubit et al. |
| 2011/0021573 A1 | 1/2011 | Hutchinson et al. |
| 2011/0021599 A1 | 1/2011 | Cotsarelis et al. |
| 2011/0028717 A1 | 2/2011 | Kugimiya et al. |
| 2011/0028807 A1 | 2/2011 | Abreu et al. |
| 2011/0034558 A1 | 2/2011 | Brittain et al. |
| 2011/0039852 A1 | 2/2011 | Hutchinson et al. |
| 2011/0040161 A1 | 2/2011 | Abreu et al. |
| 2011/0060026 A1 | 3/2011 | Hynd et al. |
| 2011/0065139 A1 | 3/2011 | Mullerad et al. |
| 2011/0071175 A1 | 3/2011 | Hynd et al. |
| 2011/0090048 A1 | 4/2011 | Li et al. |
| 2011/0098302 A1 | 4/2011 | Hutchinson et al. |
| 2011/0098352 A1 | 4/2011 | Hutchinson et al. |
| 2011/0112134 A1 | 5/2011 | Hutchinson et al. |
| 2011/0130453 A1 | 6/2011 | Hutchinson et al. |
| 2011/0144160 A1 | 6/2011 | Hutchinson et al. |
| 2011/0152338 A1 | 6/2011 | Hutchinson et al. |
| 2011/0159533 A1 | 6/2011 | Karkouche et al. |
| 2011/0166070 A1 | 7/2011 | Stewart et al. |
| 2011/0184254 A1 | 7/2011 | Grove et al. |
| 2011/0190227 A1 | 8/2011 | Hutchinson et al. |
| 2011/0237972 A1 | 9/2011 | Garfield et al. |
| 2011/0245303 A1 | 10/2011 | Hutchinson et al. |
| 2011/0301168 A1 | 12/2011 | Hutchinson et al. |
| 2011/0312927 A1 | 12/2011 | Nachaegari et al. |
| 2011/0312928 A1 | 12/2011 | Nachaegari et al. |
| 2011/0312974 A1 | 12/2011 | Hutchinson et al. |
| 2011/0318308 A1 | 12/2011 | Ragolia et al. |
| 2011/0319445 A1 | 12/2011 | Hutchinson et al. |
| 2012/0004233 A1 | 1/2012 | Stearns et al. |
| 2012/0009609 A1 | 1/2012 | Fuks et al. |
| 2012/0016029 A1 | 1/2012 | Hutchinson et al. |
| 2012/0022119 A1 | 1/2012 | Hutchinson et al. |
| 2012/0040356 A1 | 2/2012 | Hussa et al. |
| 2012/0046261 A1 | 2/2012 | Manuck et al. |
| 2012/0052595 A1 | 3/2012 | Wallace et al. |
| 2012/0058123 A1 | 3/2012 | Hutchinson et al. |
| 2012/0059055 A1 | 3/2012 | Hutchinson et al. |
| 2012/0082598 A1 | 4/2012 | Baydoun et al. |
| 2012/0157422 A1 | 6/2012 | Poston et al. |
| 2012/0196285 A1 | 8/2012 | Okamoto et al. |
| 2012/0202740 A1 | 8/2012 | Kimura et al. |
| 2012/0238469 A1 | 9/2012 | Equils et al. |
| 2012/0238894 A1 | 9/2012 | Principe et al. |
| 2012/0270747 A1 | 10/2012 | Elovitz et al. |
| 2013/0005728 A1 | 1/2013 | Harris et al. |
| 2013/0005741 A1 | 1/2013 | Harris et al. |
| 2013/0029957 A1 | 1/2013 | Giliyar et al. |
| 2013/0053670 A1 | 2/2013 | Aina-Mumuney et al. |
| 2013/0065902 A1 | 3/2013 | Aissaoui et al. |
| 2013/0071865 A1 | 3/2013 | Fuks et al. |
| 2013/0079375 A1 | 3/2013 | Endres et al. |
| 2013/0109685 A1 | 5/2013 | Aissaoui et al. |
| 2013/0158036 A1 | 6/2013 | Hutchinson et al. |
| 2013/0171672 A1 | 7/2013 | Hussa et al. |
| 2013/0177485 A1 | 7/2013 | Mullerad et al. |
| 2013/0203068 A1 | 8/2013 | Roby et al. |
| 2013/0225922 A1 | 8/2013 | Schentag et al. |
| 2013/0288249 A1 | 10/2013 | Gullberg et al. |
| 2015/0330989 A1 | 11/2015 | Burwick et al. |
| 2015/0338415 A1 | 11/2015 | Hund et al. |
| 2016/0327563 A1 | 11/2016 | Hurskainen et al. |
| 2017/0003304 A1 | 1/2017 | Demirdjian et al. |
| 2017/0023446 A1 | 1/2017 | Rietveld et al. |
| 2018/0003713 A1 | 1/2018 | Ragolia |
| 2018/0036271 A1 | 2/2018 | Ahmed et al. |
| 2018/0114600 A1 | 4/2018 | Roberts et al. |
| 2018/0259534 A1 | 9/2018 | Chaparro Padilla et al. |
| 2019/0079097 A1 | 3/2019 | Cooper et al. |
| 2019/0227074 A1 | 7/2019 | Denk et al. |
| 2019/0317108 A1 | 10/2019 | Schuitemaker |
| 2019/0353667 A1 | 11/2019 | Anderberg et al. |
| 2020/0038354 A1 | 2/2020 | Ahmed et al. |
| 2020/0264188 A1 | 8/2020 | Cooper et al. |
| 2021/0172938 A1 | 6/2021 | Oberoi et al. |

FOREIGN PATENT DOCUMENTS

| | | |
|---|---|---|
| EP | 1804836 A2 | 7/2007 |
| EP | 1804836 B1 | 11/2010 |
| EP | 1952156 B1 | 5/2011 |
| EP | 1839056 B1 | 8/2011 |
| EP | 2385134 A1 | 11/2011 |
| EP | 2172220 B1 | 1/2013 |
| EP | 1575416 B1 | 10/2013 |
| EP | 2434283 B1 | 3/2014 |
| EP | 2245180 B1 | 6/2014 |
| EP | 2912458 A1 | 9/2015 |
| EP | 1664797 B1 | 11/2015 |
| EP | 2776839 B1 | 8/2017 |
| EP | 2791683 B1 | 11/2017 |
| EP | 2867670 B1 | 5/2018 |
| EP | 2649454 B1 | 6/2018 |
| EP | 3339860 A1 | 6/2018 |
| EP | 3339861 A1 | 6/2018 |
| EP | 3097422 B1 | 7/2018 |
| EP | 2965088 B1 | 12/2018 |
| EP | 2972383 B1 | 8/2019 |
| WO | WO-9309432 A1 | 5/1993 |
| WO | WO-9309438 A1 | 5/1993 |
| WO | WO-9815830 A2 | 4/1998 |
| WO | WO-9828006 A1 | 7/1998 |
| WO | WO-2006069373 A2 | 6/2006 |
| WO | WO-2009097584 A1 | 8/2009 |
| WO | WO-2011128357 A2 | 10/2011 |
| WO | WO-2013068475 A1 | 5/2013 |
| WO | WO-2013169751 A1 | 11/2013 |
| WO | WO-2014001244 A1 | 1/2014 |
| WO | WO-2014036440 A2 | 3/2014 |
| WO | WO-2014066568 A1 | 5/2014 |
| WO | WO-2014078622 A1 | 5/2014 |
| WO | WO-2014135488 A1 | 9/2014 |
| WO | WO-2015082545 A1 | 6/2015 |
| WO | WO-2016019176 A1 | 2/2016 |
| WO | WO-2016132136 A1 | 8/2016 |
| WO | WO-2019055661 A1 | 3/2019 |
| WO | WO-2021113710 A1 | 6/2021 |

OTHER PUBLICATIONS

Holets et al. Trophoblast CD274 (B7-H1) Is Differentially Expressed Across Gestation: Influence of Oxygen Concentration. Biology of Reproduction 74, 352-358 (2006). Published online Oct. 26, 2005.

Robinson et al. Soluble endoglin as a second-trimester marker for preeclampsia. Am J Obstet Gynecol 2007;197:174e1-174.e5.

Siddiqui et al. Decorin over-expression by decidual cells in preeclampsia: a potential blood biomarker. American Journal of Obstetrics & Gynecology, vol. 215, Issue 3, p. 361.e1-361.e15 (Sep. 2016). Available online Mar. 19, 2016.

(56) References Cited

OTHER PUBLICATIONS

U.S. Appl. No. 17/234,574 Office Action dated Aug. 24, 2021.
U.S. Appl. No. 16/141,881 Office Action dated Jun. 15, 2021.
U.S. Appl. No. 17/119,410 Notice of Allowance dated Jun. 28, 2021.
U.S. Appl. No. 17/119,410 Office Action dated Feb. 26, 2021.
Akolekar et al. Competing Risks Model in Early Screening for Preeclampsia by Biophysical and Biochemical Markers. Fetal Diagn Ther 33:8-15 (2013). Published online Aug. 16, 2012. DOI: 10.1159/000341264.
Akolekar et al. Prediction of early, intermediate and late preeclampsia from maternal factors, biophysical and biochemical markers at 11-13 weeks. Prenat Diagn 31:66-74 (2011). DOI: 10.1002/pd.2660.
Anand et al. Serum biomarkers predictive of pre-eclampsia. Biomark Med 9(6):563-575 (2015). doi: 10.2217/bmm.15.21.
Berzan et al. Treatment of Preeclampsia: Current Approach and Future Perspectives. Curr Hypertens Rep 16:473 (2014). 6 pages. DOI: https://doi.org/10.1007/s11906-014-0473-5.
Burwick et al. Complement activation and kidney injury molecule-1-associated proximal tubule injury in severe preeclampsia. Hypertension 64(4):833-8 (Oct. 2014). doi: 10.1161/HYPERTENSIONAHA.114.03456. Epub Jun. 23, 2014.
Caritis, et al. A double-blind study comparing ritodrine and terbutaline in the treatment of preterm labor. American journal of obstetrics and gynecology 150.1 (1984): 7-14. (Abstract).
Carty et al. Novel biomarkers for predicting preeclampsia. Trends in Cardiovascular Medicine. 18(5):186-194 (2008).
Casanova-Morales et al. Identifying Chaotropic and Kosmotropic Agents by Nanorheology. J. Phys. Chem. B 2018, 122, 14, 3754-3759 (Mar. 14, 2018).
Chobanian et al. The Seventh Report of the Joint National Committee on Prevention, Detection, Evaluation, and Treatment of High Blood Pressure. JAMA 289(19):2560-2572 (May 21, 2003). doi:10.1001/jama.289.19.2560.
CLEC4A ELISA kit; 2006; retrieved from https://cdn.mybiosource.com/tds/protocol_manuals/800000-9999999/M8S7213205.pdf. 8 pages.
Co-pending U.S. Appl. No. 15/329,924, inventors Cooper; Matthew et al., filed Jan. 27, 2017.
Co-pending U.S. Appl. No. 17/234,574, inventors Cooper; Matthew et al., filed Apr. 19, 2021.
Cowans et al. Early first-trimester maternal serum placental growth factor in trisomy 21 pregnancies. Ultrasound Obstet Gynecol 2011; 37: 515-519.
Cowans et al. Stability of first trimester placental growth factor in serum and whole blood. Prenat Diagn 31:1193-1197 (2011). First published: Oct. 26, 2011.
Darmochwal-Kolarz et al. The expression of B7-H1 and B7-H4 co-stimulatory molecules on myeloid and plasmacytoid dendritic cells in pre-eclampsia and normal pregnancy. J Reprod Immunol 99 (2013) 33-38.
Dissociation constant, chemeurope.com. Published Mar. 19, 2007. Retrieved Apr. 1, 2021 at URL: https://www.chemeurope.com/en/encyclopedia/Dissociation_constant.html. 4 pages.
Doucet et al. Development and Validation of an ELISA at Acidic pH for the Quantitative Determination of IL-13 in Human Plasma and Serum. Disease Markers, vol. 35, Issue 5, pp. 465-474 (2013). DOI: http://dx.doi.org/10.1155/2013/290670.
Dwivedi, et al. Systematic review of the role of prostaglandins. World J Pharm Pharm Sci. 3(2). (2013): 2249-69.
Easy molecular bonding-crosslinking technology. Thermo Scientific Crosslinking Technical Handbook. Thermo Scientific. Published Aug. 16, 2015. Retrieved Apr. 1, 2021 from URL: <url: http://tools.thermofisher.com/content/sfs/brochures/1602163-Crosslinking-Reagents-</url:>Handbook.pdf. 56 pages.
Elecsys® sFlt-1/PlGF (Preeclampsia). (Website.) Roche Diagnostics. 4 pages. Accessed Oct. 30, 2018 at URL: https://diagnostics.roche.com/global/en/products/params/elecsys-sflt-1-plgf-preeclampsia.html.

Emptoz-Bonneton et al. Novel Human Corticosteroid-Binding Globulin Variant with Low Cortisol-Binding Affinity. The Journal of Clinical Endocrinology & Metabolism, vol. 85, Issue 1, Jan. 1, 2000, pp. 361-367.
EP18167167.8 Communication and Search Report dated Jun. 18, 2018.
EP18856306.8 Extended European Search Report dated Feb. 3, 2021.
EP18856306.8 Partial Supplementary European Search Report dated Oct. 5, 2020.
Fortier, et al. A postgenomic integrated view of prostaglandins in reproduction: implications for other body systems. J Physiol Pharmacol59.Suppl 1 (2008): 65-89.
Gravett, et al. Proteomic Analysis of Cervical-Vaginal Fluid: Identification of Novel Biomarkers for Detection of Intra-Amniotic Infection. J Proteome Res. Jan. 2007; 6(1): 89-96. doi:10.1021/pr060149v.
Helliwell, et al. Gestational Age-Dependent Up-Regulation of Prostaglandin D Synthase (PGDS) and Production of PGDS-Derived Antiinflammatory Prostaglandins in Human Placenta, The Journal of Clinical Endocrinology & Metabolism, vol. 91, Issue 2, Feb. 1, 2006, pp. 597-606, https://doi.org/10.1210/jc.2005-1982.
Human C. Type Lectin Domain Family 4 Member A (CLEC4A) Elisa Kit (Competitive ELISA), Catalog No. MBS7213205 (2017). 8 pages. Retrieved Jul. 10, 2020 from URL: https://cdn.mybiosource.com/tds/protocol_manuals/800000-9999999/MBS7213205.pdf.
Human Fibroblast Growth Factor-21 ELISA. Cat. No. RD191108200R, BioVendor Research and Diagnostic Products, Czech Republic. BioMedical Specimen Bank, Czech Republic. (Sep. 2013). 2 pages. Retrieved from http://npt.ir/uploads/RD191108200R.pdf.
Hund et al. Influence of the sFlt-1/PlGF ratio on clinical decision-making in women with suspected preeclampsia—the PreOS study protocol. Hypertension in Pregnancy 34(1):102-115 (Jan. 28, 2015). DOI: https://doi.org/10.3109/10641955.2014.982331.
Hund et al. Multicenter prospective clinical study to evaluate the prediction of short-term outcome in pregnant women with suspected preeclampsia (Prognosis): study protocol. BMC Pregnancy and Childbirth 14:324 (Sep. 18, 2014.) 10 pages. DOI: https://doi.org/10.1186/1471-2393-14-324.
Hypertension in pregnancy. Report of the American College of Obstetricians and Gynecologists' Task Force on Hypertension in Pregnancy. Obstet Gynecol 122(5):1122-1131 (Nov. 1, 2013). doi: 10.1097/01.AOG.0000437382.03963.88.
Iyer et al. The crystal structure of human placenta growth factor-1 (PlGF-1), an angiogenic protein, at 2.0 A resolution. J Biol Chem. Apr. 13, 2001;276(15):12153-61. doi: 10.1074/jbc.M008055200. Epub Nov. 7, 2000.
Khan, et al. Prostaglandins in labor—a translational approach. Front Biosci 13 (2008): 5794-5809.
Klein et al. Influence of the sFlt-1/PlGF Ratio on Clinical Decision-Making in Women with Suspected Preeclampsia. PLOS One (May 31, 2016). 19 pages. DOI:10.1371/journal.pone.0156013.
Kuhle et al. Comparison of three analytical platforms for quantification of the neurofilament light chain in blood samples: ELISA, electrochemiluminescence immunoassay and Simoa. Clin Chem Lab Med. Oct. 1, 2016;54(10):1655-61. doi: 10.1515/cclm-2015-1195.
Kumar, et al. Role of Lipocalin-type prostaglandin D2 synthase (L-PGDS) and its metabolite, prostaglandin D2, in preterm birth. Prostaglandins & other lipid mediators 118 (Apr. 1, 2015): 28-33.
Lecarpentier et al. Total Versus Free Placental Growth Factor Levels in the Pathogenesis of Preeclampsia. Hypertension, vol. 76, Issue 3, pp. 875-883 (Sep. 2020). Originally published Jul. 13, 2020. DOI: https://doi.org/10.1161/HYPERTENSIONAHA.120.15338.
Lee, et al. Amniotic fluid prostaglandin concentrations increase before the onset of spontaneous labor at term. The Journal of Maternal-Fetal & Neonatal Medicine 21.2 (2008): 89-94.
Li et al. Progress in Exosome Isolation Techniques. Theranostics 7(3):789-804 (Jan. 26, 2017). doi: 10.7150/thno.18133.
Liu et al. Integrating multiple 'omics' analysis identifies serological protein biomarkers for preeclampsia. BMC Medicine 11:236 (2016). 12 pages.

(56) References Cited

OTHER PUBLICATIONS

Lowe et al. SOMANZ guidelines for the management of hypertensive disorders of pregnancy 2014. Australian and New Zealand Journal of Obstetrics and Gynaecology 2015; 55: e1-e29.

Lundberg et al., Homogeneous antibody-based proximity extension assays provide sensitive and specific detection of low-abundant proteins in human blood, Nucleic Acids Res.(2011) 39(15):e102. 8 pages.

Luttun et al. Soluble VEGF receptor Flt1: the elusive preeclampsia factor discovered? The Journal of Clinical Investigation, vol. 111, No. 5, pp. 600-602 (Mar. 2003). DOI:10.1172/JCI200318015.

Marceau, et al. Role of nuclear receptors Peroxisome Proliferator-Activated Receptors (PPARs) and Liver X receptors (LXRs) in the human placental pathophysiology. Recent Advances in Research on the Human Placenta. IntechOpen, 2012. 379-396.

Maynard et al. Excess placental soluble fms-like tyrosine kinase 1 (sFlt1) may contribute to endothelial dysfunction, hypertension, and proteinuria in preeclampsia. The Journal of Clinical Investigation, vol. 111, No. 5, pp. 649-658 (Mar. 2003). DOI: 10.1172/JCI17189.

McConway et al. Differences in circulating concentrations of total, free and bound leptin relate to gender and body composition in adult humans. Ann Clin Biochem 37:717-723 (2000).

Mestecky, Jiri, et al. "Manual for collection and processing of mucosal specimens." Laboratory for Assessment of Mucosal Immune Responses Induced by AIDS Vaccines in Clinical Trial Volunteers, National Institute of Health, Division of AIDS (1999).

Molvarec et al. Circulating angiogenic factors determined by electrochemiluminescence immunoassay in relation to the clinical features and laboratory parameters in women with preeclampsia. Hypertension Research 33:892-898 (Jun. 10, 2010).

Myatt. Association of maternal biomarkers with obstetric outcomes. Reproductive Sciences. vol. 20, Suppl. 1, Abstract S-207 (2013). 60th Annual Meeting, Society for Gynecologic Investigation, Orlando, FL, USA, Mar. 20-23, 2013.

Myatt. Identification of different phenotypes of preeclampsia by clustering analysis of biomarker profiles. Reproductive Sciences. vol. 20, Suppl. 1, Abstract F-255 (2013). 60th Annual Meeting, Society for Gynecologic Investigation, Orlando, FL, USA, Mar. 20-23, 2013.

Nitert et al. Placental fibroblast growth factor 21 is not altered in late-onset preeclampsia. Reprod Biol Endocrinol. 2015; 13: 14. Published online Mar. 8, 2015. doi: 10.1186/s12958-015-0006-3. 8 pages.

O'Gorman et al. Competing risks model in screening for preeclampsia by maternal factors and biomarkers at 11-13 weeks gestation. American Journal of Obstetrics and Gynecology 214(1):103.e1-103.e12 (Jan. 2016). DOI: https://doi.org/10.1016/j.ajog.2015.08.034.

Olson, et al. Role of the prostaglandins in labour and prostaglandin receptor inhibitors in the prevention of preterm labour. Front Biosci. Jan. 1, 2007;12:1329-43.

Park et al. Placenta growth factor. Potentiation of vascular endothelial growth factor bioactivity, in vitro and in vivo, and high affinity binding to Flt-1 but not to Flk-1/KDR. J Biol Chem, vol. 269, No. 41, Issue of Oct. 14, pp. 25646-25654 (1994).

Park et al. Screening models using multiple markers for early detection of late-onset preeclampsia in low-risk pregnancy. BMC Pregnancy and Childbirth. 14:35 (2014). 11 pages.

Patton, et al. Proteomic analysis of the cerebrospinal fluid of patients with restless legs syndrome/Willis-Ekbom disease. Fluids and Barriers of the CNS 10.1 (2013): 20. 8 pages.

PCT/US2013/066490 Written Opinion of the International Searching Authority dated Jan. 14, 2014.

PCT/US2013/066490 International Search Report dated Jan. 14, 2014.

PCT/US2015/042976 International Search Report and Written Opinion dated Nov. 23, 2015.

PCT/US2018/050893 International Search Report and Written Opinion dated Dec. 12, 2018.

PCT/US2020/063408 International Search Report and Written Opinion dated Feb. 10, 2021.

Pennings et al. Integrative data mining to identify novel candidate serum biomarkers for preeclampsia screening. Prenatal Diagnosis 31:1153-1159 (Sep. 22, 2011).

Pettipher, et al. Antagonism of the prostaglandin D 2 receptors DP 1 and CRTH2 as an approach to treat allergic diseases. Nature Reviews Drug Discovery 6.4 (2007): 313-325.

Phillips, et al. Genes for prostaglandin synthesis, transport and inactivation are differentially expressed in human uterine tissues, and the prostaglandin F synthase AKR1B1 is induced in myometrial cells by inflammatory cytokines. Molecular human reproduction 17.1 (Jul. 1, 2010): 1-13.

Phillips, et al. Prostaglandin pathway gene expression in human placenta, amnion and choriodecidua is differentially affected by preterm and term labour and by uterine inflammation. BMC pregnancy and childbirth 14.1 (Jan. 1, 2014): 241. 14 pages.

Phipps et al. Preeclampsia: Updates in Pathogenesis, Definitions, and Guidelines. Clinical Journal of the American Society of Nephrology 11(6):1102-1113 (Jun. 2016). DOI: https://doi.org/10.2215/CJN.12081115..

Pinhal-Enfield, et al. The role of macrophages in the placenta. Embryology—Updates and Highlights on Classic Topics. IntechOpen, 2012.

Pirianov, et al. The cyclopentenone 15-deoxy-delta12,14-prostaglandin J2 delays lipopolysaccharide-induced preterm delivery and reduces mortality in the newborn mouse. Endocrinology 150.2 (Epub Oct. 9, 2008): 699-706.

Poon et al. First-Trimester Prediction of Hypertensive Disorders in Pregnancy. Hypertension 53:812-818 (Mar. 9, 2009). doi: 10.1161/HYPERTENSIONAHA.108.127977.

Poon et al. First-trimester maternal factors and biomarker screening for preeclampsia. Prenatal Diagnosis 34(7):618-627 (Jul. 2014). First published Apr. 25, 2014. DOI: https://doi.org/10.1002/pd.4397.

Preeclampsia and angiogenic factors. sFlt-1/PlGF ratio in the diagnosis of preeclampsia. Cobas booklet, Roche (2013). 12 pages.

Quantikine ELISA—Human Endoglin/CD105 Immunoassay. Catalog No. DNDG00. Package Insert. R&D Systems, Inc. Published on Oct. 10, 2004. Retrieved Apr. 1, 2021 from URL: https://resources.rndsystems.com/pdfs/datasheets/dndg00.pdf. 16 pages.

Quantikine ELISA—Human PlGF Immunoassay. Catalog No. DPG00, SPG00, PDPG00. Package Insert. Published on Dec. 11, 2012. Retrieved Apr. 1, 2021 at URL: https://resources.rndsystems.com/pdfs/datasheets/dpg00.pdf. 16 pages.

Rinaldi, et al. Anti-inflammatory mediators as physiological and pharmacological regulators of parturition. Expert review of clinical immunology7.5 (2011): 675-696.

Romero et al. Expression of placental fibroblast growth factor 21 (FGF21) is increased in placental tissue from pregnancies with preeclampsia. Placenta, vol. 35, Issue 9, Sep. 2014, p. A84. DOI: https://doi.org/10.1016/j.placenta.2014.06.271.

Sabbisetti et al. Blood kidney injury molecule-1 is a biomarker of acute and chronic kidney injury and predicts progression to ESRD in type I diabetes. J Am Soc Nephrol 25:2177-2186 (2014).

Sano, et al. Immuno-PCR: Very sensitive antigen detection by means of specific antibody-DNA conjugates. Science. 258 (1992): 120-122.

Shiki, et al. Changes of lipocalin-type prostaglandin D synthase level during pregnancy. J Obstet Gynaecol Res. Feb. 2004;30(1):65-70.

Spencer et al. ADAM12s in maternal serum as a potential marker of pre-eclampsia. Prenatal Diagnosis 28:212-216 (Feb. 8, 2008).

Spencer et al. Low levels of maternal serum PAPP-A in the first trimester and the risk of pre-eclampsia. Prenatal Diagnosis 28(1):7-10 (Jan. 2008). First published Nov. 14, 2007. DOI: https://doi.org/10.1002/pd.1890.

Spencer et al. Screening for trisomy 21 in twin pregnancies in the first trimester: an update of the impact of chorionicity on maternal serum markers. Prenatal Diagnosis 28(1):49-52 (Jan. 2008). DOI: https://doi.org/10.1002/pd.1923.

Stepan et al. Serum levels of the adipokine fibroblast growth factor-21 are increased in preeclampsia . Cytokine, vol. 62, Issue 2, May 2013, pp. 322-326. Available online Mar. 29, 2013.

(56) References Cited

OTHER PUBLICATIONS

Sykes, et al. Anti-inflammatory prostaglandins for the prevention of preterm labour. Reproduction 148.2 (2014): R29-R40.

Sykes, et al. Changes in the Th1: Th2 Cytokine Bias in Pregnancy and the Effects of the Anti-Inflammatory Cyclopentenone Prostaglandin 15-Deoxy-Prostaglandin. Mediators of inflammation 2012 (2012). 12 pages.

Taylor et al. High plasma cellular fibronectin levels correlate with biochemical and clinical features of preeclampsia but cannot be attributed to hypertension alone. 165(4) Part 1, pp. 895-901 (Oct. 1991). DOI: https://doi.org/10.1016/0002-9378(91)90435-T.

Tejera et al. Preeclampsia: a bioinformatics approach through protein-protein interaction networks analysis. BMC Systems Biology 6:97 (2012). 9 pages.

Thorsen, Stine Buch et al. Detection of serological biomarkers by proximity extension assay for detection of colorectal neoplasias in symptomatic individuals. Journal of Translational Medicine 11(253): 1-13 (2013).

Tsiakkas et al. Maternal serum placental growth factor at 12, 22, 32 and 36 weeks' gestation in screening for pre-eclampsia. Ultrasound Obstet Gynecol 47:472-477 (Mar. 7, 2016). DOI: 10.1002/uog.15816.

Ullman et al. Luminescent oxygen channeling assay (LOCI): sensitive, broadly applicable homogeneous immunoassay method. Clinical Chemistry 42(9):1518-1526 (Sep. 1996).

Ullman et al. Luminescent oxygen channeling immunoassay: measurement of particle binding kinetics by chemiluminescence. PNAS 91(12):5426-5430 (Jun. 7, 1994). DOI: https://doi.org/10.1073/pnas.91.12.5426.

U.S. Appl. No. 14/438,110 Notice of Allowance dated Jun. 19, 2017.

U.S. Appl. No. 14/438,110 Office Action dated Aug. 12, 2016.

U.S. Appl. No. 14/438,110 Office Action dated Feb. 21, 2017.

U.S. Appl. No. 15/708,582 Office Action dated Sep. 4, 2018.

U.S. Appl. No. 16/141,881 Office Action dated Apr. 16, 2020.

U.S. Appl. No. 16/141,881 Office Action dated Feb. 5, 2021.

U.S. Appl. No. 16/141,881 Office Action dated Oct. 2, 2019.

Verlohren et al. New Gestational Phase-Specific Cutoff Values for the Use of the Soluble fms-Like Tyrosine Kinase-1/Placental Growth Factor Ratio as a Diagnostic Test for Preeclampsia. Hypertension 63(2):346-352 (Oct. 28, 2013).

Verlohren et al. The sFlt-1/PlGF ratio in different types of hypertensive pregnancy disorders and its prognostic potential in preeclamptic patients. American Journal of Obstetrics & Gynecology, Month 2011, pp. 1.e1-1.e8 (2011). doi: 10.1016/j.ajog.2011.07.037.

Verlohren et al. An automated method for the determination of the sFlt-1/PlGF ratio in the assessment of preeclampsia. American Journal of Obstetrics and Gynecology. 202(2):161.e1-161.e11 (Feb. 2010). DOI: https://doi.org/10.1016/j.ajog.2009.09.016.

Wang et al. Increased urinary levels of podocyte glycoproteins, matrix metallopeptidases, inflammatory cytokines, and kidney injury biomarkers in women with preeclampsia. Am J Physiol Renal Physiol 309(12):F1009-F1017 (2015). First published Oct. 14, 2015; doi:10.1152/ajprenal.00257.2015.

Warner, et al. Cyclooxygenases: new forms, new inhibitors, and lessons from the clinic. The FASEB journal 18.7 (May 1, 2004): 790-804.

Weinstein. Syndrome of hemolysis, elevated liver enzymes, and low platelet count: A severe consequence of hypertension in pregnancy. American Journal of Obstetrics and Gynecology 142(2):159-167 (Jan. 15, 1982). DOI: https://doi.org/10.1016/S0002-9378(16)32330-4.

Whelton et al. 2017 ACC/AHA/AAPA/ABC/ACPM/AGS/APhA/ASH/ASPC/NMA/PCNA Guideline for the Prevention, Detection, Evaluation, and Management of High Blood Pressure in Adults. Journal of the American College of Cardiology 71(19):e127-248 (May 2018). DOI: 10.1016/j.jacc.2017.11.006.

Xiao et al. Combined biomarkers evaluation for diagnosing kidney injury in preeclampsia. Hypertens Pregnancy 32(4):439-49 (Nov. 2013). doi: 10.3109/10641955.2013.827203. Epub Aug. 19, 2013.

Zegels, et al. Comprehensive proteomic analysis of human cervical-vaginal fluid using colposcopy samples. Proteome science 7.1 (2009): 17. 16 Pages.

Zeisler et al. Predictive Value of the sFlt-1:PlGF Ratio in Women with Suspected Preeclampsia. N Engl J Med 374:13-22 (2016). DOI: 10.1056/NEJMoa1414838.

\* cited by examiner

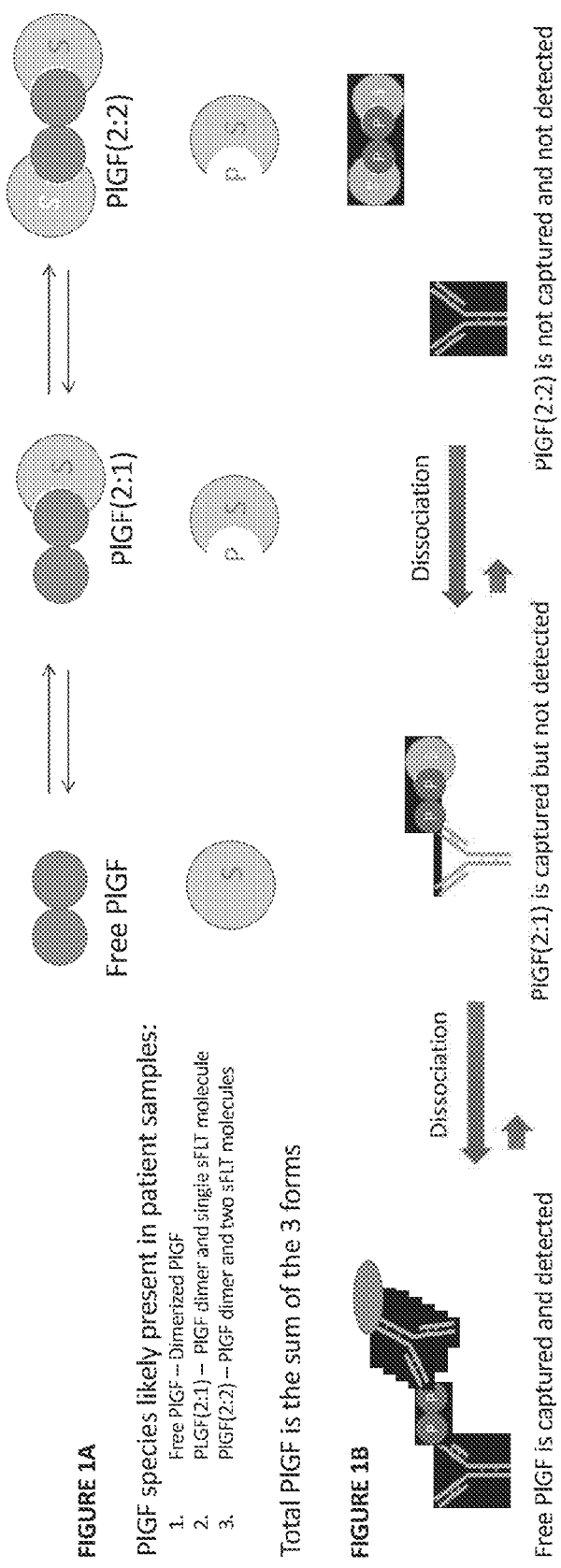

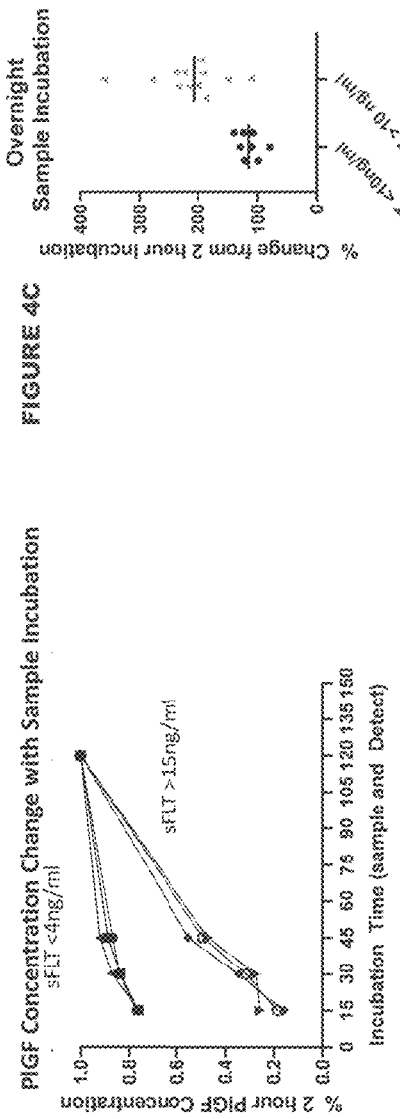
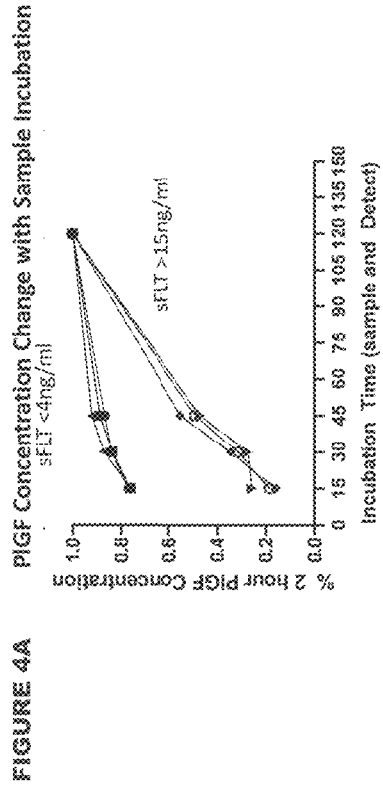
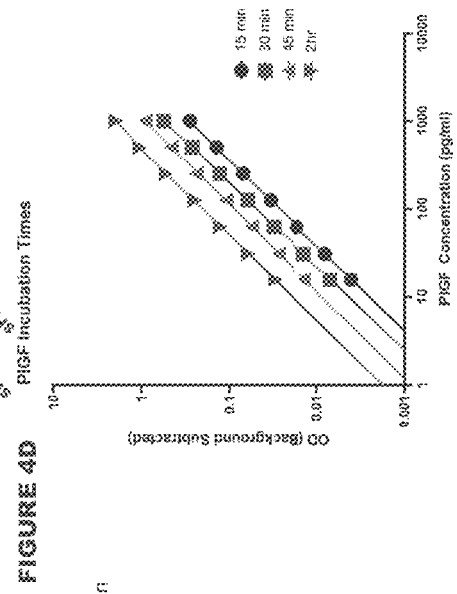
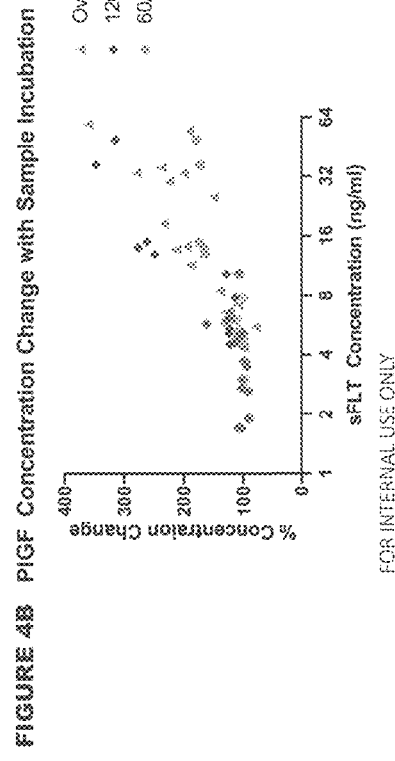
FIGURE 4A  PlGF Concentration Change with Sample Incubation
FIGURE 4B  PlGF Concentration Change with Sample Incubation
FIGURE 4C  Overnight Sample Incubation
FIGURE 4D  PlGF Incubation Times

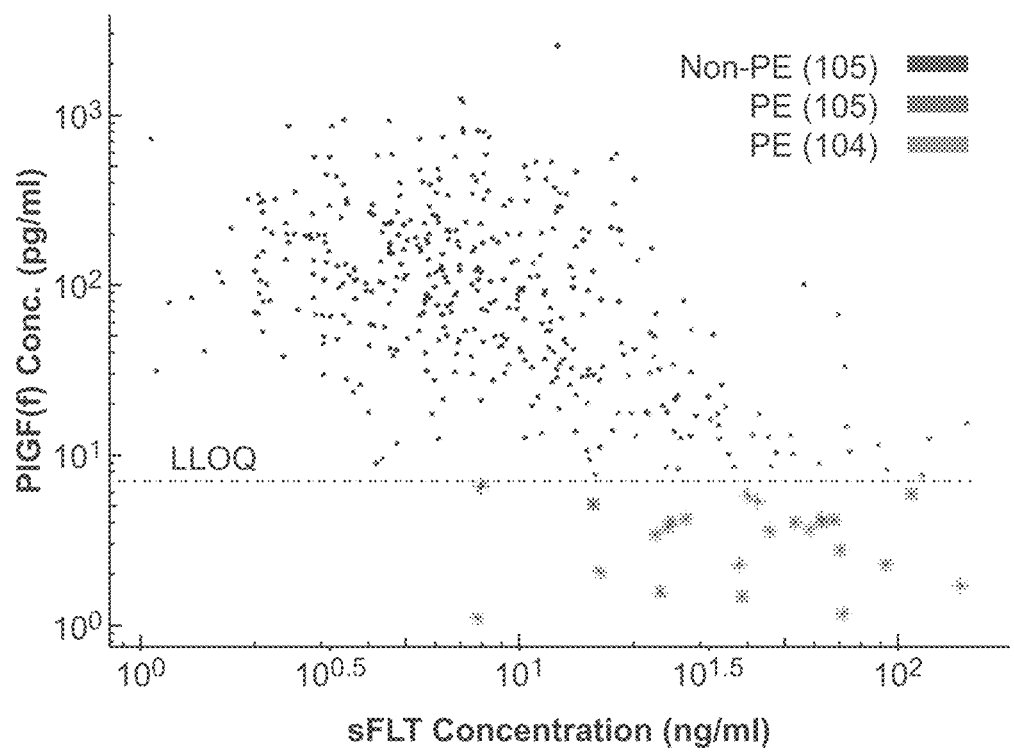
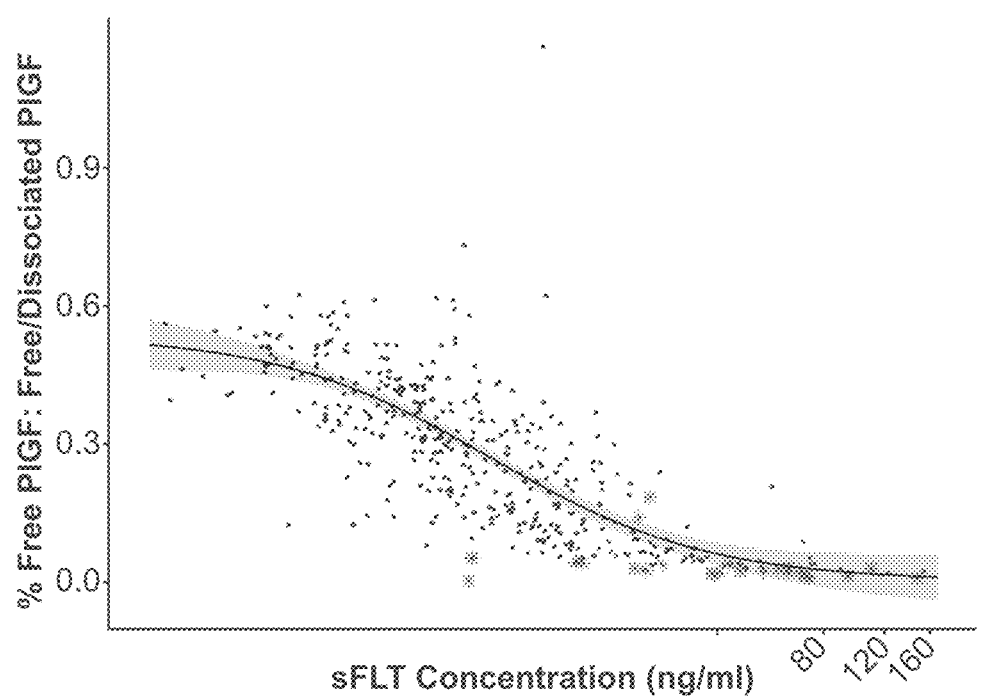
FIG. 6

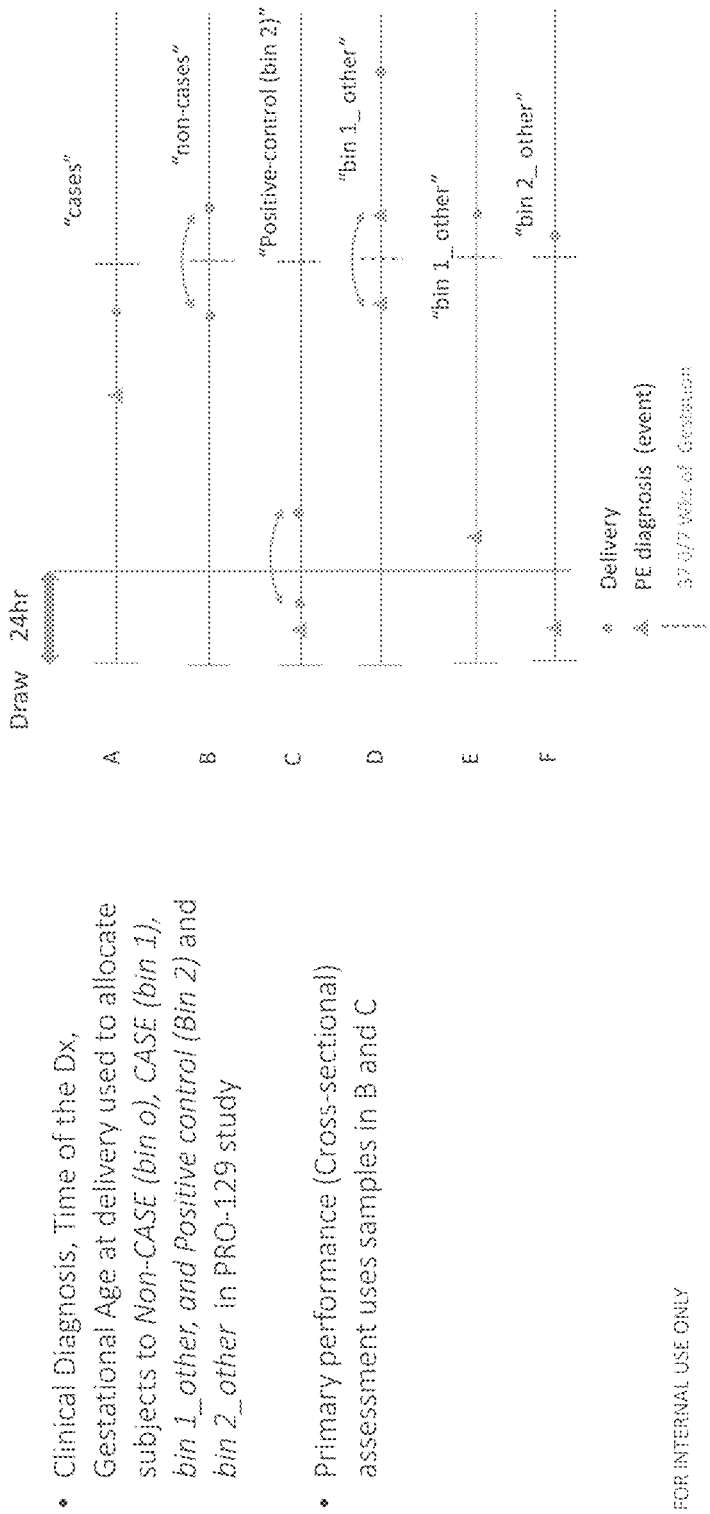

ASSESSMENT OF PREECLAMPSIA USING ASSAYS FOR FREE AND DISSOCIATED PLACENTAL GROWTH FACTOR

CROSS-REFERENCE STATEMENT

This application is a continuation of U.S. application Ser. No. 17/119,410, filed Dec. 11, 2020, which is a continuation of International Application No. PCT/US2020/063408, filed Dec. 4, 2020, which claims the benefit of U.S. Provisional Application No. 62/943,739 entitled "Detection Of Preeclampsia Using Assays For Free And Dissociated Placental Growth Factor", filed on Dec. 4, 2019 and U.S. Provisional Application No. 62/947,957 entitled "Detection Of Preeclampsia Using Assays For Free And Dissociated Placental Growth Factor", filed on Dec. 13, 2019, all of which are incorporated by reference herein in their entireties.

BACKGROUND OF THE INVENTION

Preeclampsia is a serious multisystem complication of pregnancy. The incidence of the disorder is generally considered to be between 2% to 8% of all pregnancies, and the disorder carries significant morbidity and mortality risks for both mothers and infants. Preeclampsia is the second largest cause of maternal/fetal deaths and is responsible for approximately twenty billion dollars in healthcare costs annually. In the United States, approximately one million women present with classical symptoms of preeclampsia (hypertension and/or proteinuria after the $20^{th}$ month of gestation) each year.

The cause(s) and pathogenesis of preeclampsia remain uncertain, and the identification (or ruling out) of preeclampsia using the classical clinical symptoms of the disease is non-ideal. The presentation of classical clinical symptoms can be highly variable, and the symptoms can be indicative of other distinct disorders, such as chronic hypertension, gestational hypertension, temporary high blood pressure, and gestational diabetes. Current laboratories tests (e.g., tests for proteinuria) can be prone to inaccuracies, or are useful for detection of preeclampsia only during relatively late periods in the progression of the disorder. Methods for more reliably predicting whether a pregnant woman will or will not have preeclampsia may, among other things, (1) lead to more timely diagnosis, (2) improve the accuracy of a diagnosis, and/or (3) prevent the unnecessary treatment of women with some preeclampsia symptoms.

Previous studies have used free levels of the vascular factors PlGF and/or sFLT as biomarkers of preeclampsia. However, levels of these free factors alone measured using known methods have limited sensitivity and specificity.

SUMMARY OF THE INVENTION

In some aspects, the present disclosure provides for a method of determining whether a pregnant human female is at risk of suffering from preeclampsia comprising: determining a free Placental Growth Factor to dissociated Placental Growth Factor (PlGF-f:PlGF-d) ratio of a biological sample collected from the pregnant human female, wherein a PlGF-f:PlGF-d ratio less than a first threshold value indicates a heightened risk that the pregnant human female will suffer from preeclampsia, and wherein a PlGF-f:PlGF-d ratio greater than a second threshold value indicates a reduced risk that the pregnant human female will suffer from preeclampsia. In some embodiments, the method comprises collecting the biological sample. In some embodiments, the biological sample is a fluid, whole blood, peripheral blood, serum, plasma, urine, or amniotic fluid sample. In some embodiments, the method comprises collecting the biological sample via venipuncture, fingerstick sampling, or arterial sampling. In some embodiments, the biological sample is collected from the pregnant woman at gestational week 20 or later. In some embodiments, the biological sample is collected from the pregnant woman prior to gestational week 30. In some embodiments, the risk of developing preeclampsia is the risk of developing preeclampsia within the following one, two, three or more weeks. In some embodiments, the PlGF-f:PlGF-d ratio is determined at least in part by: (a) determining a PlGF-f level by contacting a first PlGF probe to a first portion of the biological sample; and (b) determining a PlGF-d level by contacting the first PlGF probe to a second portion of the biological sample, wherein the first portion of the biological sample is untreated, and wherein a treatment is applied to the second portion of the biological sample, and wherein the treatment dissociates a PlGF complex. In some embodiments, the PlGF complex comprises PlGF and s-FLT. In some embodiments, the treatment is applied for at least 5, 10, 15, 20, 25, 30, 40, 50, 60, 90, or 120 minutes. In some embodiments, the treatment comprises increasing the temperature of the second portion of the biological sample. In some embodiments, the treatment comprises increasing the temperature to at least 30° C., at least 37° C., or at least 45° C. for at least 1 hour or at least 2 hours. In some embodiments, the treatment comprises increasing or decreasing the pH of the second portion of the biological sample. In some embodiments, the treatment comprises contacting the second portion of the biological sample with an agent that prevents PlGF from assembling into a PlGF complex. In some embodiments, the agent is selected from: a surfactant, a detergent, a chaotropic agent, a PlGF-binding protein, and an s-FLT-binding protein. In some embodiments, the first unmodified portion of the biological sample has not been stored at a temperature above about 20° C. In some embodiments, the method has a LLOQ for PlGF of 20 pg/ml or less. In some embodiments, the method comprises (a) determining a level of at least one secondary biomarker selected from total sFLT, free sFLT, Endoglin, KIM-1, FGF21, Decorin, Clec4A and CD274; and (b) determining the pregnant woman as being at risk or not at risk of preeclampsia by application of a trained algorithm to the PlGF-f:PlGF-d ratio in combination with the determined level least one of the secondary biomarker In some embodiments, the trained algorithm comprises a logistic regression, random forest, nearest centroid, gradient boosting method, linear discriminant analysis, neural network, or support vector machine algorithm. In some embodiments, the level of the at least one secondary biomarker is determined by an immunoassay. In some embodiments, the immunoassay is selected from a capture ELISA, an indirect ELISA, a TR-FRET assay, a proximity extension assay, an amplified luminescent proximity (LOCI) assay, a luminescent oxygen channeling immunoassay, or a lateral flow assay.

In some aspects, the present disclosure provides for a method of treating a pregnant human female comprising: determining whether the pregnant human female has an elevated risk of preeclampsia or reduced risk of preeclampsia by: obtaining a biological sample from the pregnant human female, determining a PlGF-f:PlGF-d ratio in the biological sample, and optionally determining a level of one or more secondary biomarkers in the biological sample, applying a classifier to the PlGF-f:PlGF-d ratio and, optionally, the level of one or more secondary biomarkers to classify the pregnant human female as having an elevated risk of preeclampsia or a reduced risk of preeclampsia; if the pregnant human female has an elevated risk of preeclampsia, then determining the blood pressure of the pregnant human female at a frequency of at least one time per week, and if the pregnant human female has a reduced risk of preeclampsia, then determining the blood pressure of the pregnant human female at a frequency of less than one time per week. In some embodiments, the method comprises, if the pregnant human female is determined to have an elevated risk of preeclampsia, then administering an antihypertensive drug to the pregnant human female. In some embodiments, the antihypertensive drug is a central alpha agonist, a vasodilator, a calcium-channel blocker, an alpha-blocker, acetylsalicylic acid, or a beta-blocker. In some embodiments, the antihypertensive drug is methyldopa, labetalol, nifedipine, verapamil, clonidine, hydralazine, diazoxide, prazosin, or oxprenolol. In some embodiments, the method comprises administering a cervical ripening or labor-inducing agent to the pregnant woman when the pregnant woman is determined to be at risk of suffering from preeclampsia. In some embodiments, the cervical ripening or labor-inducing agent comprises a prostaglandin, oxytocin, misoprostol, mifepristone, or relaxin.

In some embodiments, the present disclosure provides for a method for avoiding unnecessary treatment of preeclampsia, the method comprising: (a) contacting a biological sample that has been collected from a pregnant human female with a plurality of different antigen-specific probes to determine levels of three or more markers, wherein the three or more markers comprise at least (i) PlGF-f and PlGF-d; and (ii) at least one of sFLT, Endoglin, KIM-1, FGF21, or free sFLT; and (b) proceeding with treatment of the pregnant human in a manner that avoids unnecessary treatment of preeclampsia based at least in part on the amounts or concentrations of the three or more markers determined in (a). In some embodiments, the method comprises collecting the biological sample. In some embodiments, the biological sample is a fluid, whole blood, peripheral blood, serum, plasma, urine, or amniotic fluid sample. In some embodiments, the method comprises collecting the biological sample via venipuncture, fingerstick sampling, or arterial sampling. In some embodiments, the biological sample is collected from the pregnant woman at gestational week 20 or later. In some embodiments, the biological sample is collected from the pregnant woman prior to gestational week 30. In some embodiments, the risk of developing preeclampsia is the risk of developing preeclampsia within the following one, two, three or more weeks. In some embodiments, the PlGF-f:PlGF-d ratio is determined at least in part by: (a) determining a PlGF-f level by contacting a first PlGF probe to a first portion of the biological sample; and (b) determining a PlGF-d level by contacting the first PlGF probe to a second portion of the biological sample, wherein the first portion of the biological sample is untreated, and wherein a treatment is applied to the second portion of the biological sample, and wherein the treatment dissociates a PlGF complex. In some embodiments, the PlGF complex comprises PlGF and s-FLT. In some embodiments, the treatment is applied for at least 5, 10, 15, 20, 25, 30, 40, 50, 60, 90, or 120 minutes. In some embodiments, the treatment comprises increasing the temperature of the second portion of the biological sample. In some embodiments, the treatment comprises increasing the temperature to at least 30° C., at least 37° C., or at least 45° C. for at least 1 hour or at least 2 hours. In some embodiments, the treatment comprises increasing or decreasing the pH of the second portion of the biological sample. In some embodiments, the treatment comprises contacting the second portion of the biological sample with an agent that prevents PlGF from assembling into a PlGF complex. In some embodiments, the agent is selected from: a surfactant, a detergent, a chaotropic agent, a PlGF-binding protein, and an s-FLT-binding protein. In some embodiments, the first unmodified portion of the biological sample has not been stored at a temperature above about 20° C. In some embodiments, the method has a LLOQ for PlGF of 20 pg/ml or less. In some embodiments, the method comprises (a) determining a level of at least one secondary biomarker selected from total sFLT, free sFLT, Endoglin, KIM-1, FGF21, Decorin, Clec4A and CD274; and (b) determining the pregnant woman as being at risk or not at risk of preeclampsia by application of a trained algorithm to the PlGF-f:PlGF-d ratio in combination with the determined level least one of the secondary biomarker In some embodiments, the trained algorithm comprises a logistic regression, random forest, nearest centroid, gradient boosting method, linear discriminant analysis, neural network, or support vector machine algorithm. In some embodiments, the level of the at least one secondary biomarker is determined by an immunoassay. In some embodiments, the immunoassay is selected from a capture ELISA, an indirect ELISA, a TR-FRET assay, a proximity extension assay, an amplified luminescent proximity (LOCI) assay, a luminescent oxygen channeling immunoassay, or a lateral flow assay.

In some embodiments, the present disclosure provides for a system for ruling out preeclampsia in a pregnant female subject for a specified period of time, the system comprising: a processor; an input module for inputting levels of at least three markers in a biological sample, wherein the at least three markers comprise at least (i) PlGF-f and PlGF-d; and (ii) at least one of sFLT, Endoglin, KIM-1, FGF21, or free sFLT; a computer readable medium containing instructions that, when executed by the processor, perform a first algorithm on the input levels of the at least three markers; and an output module providing one or more indicia based on the input levels of the at least three markers, wherein the one or more indicia are indicative of the subject not having preeclampsia for at least a specified period of time. In some embodiments, the biological sample is a fluid, whole blood, peripheral blood, serum, plasma, urine, or amniotic fluid sample. In some embodiments, the biological sample is collected from the pregnant woman at gestational week 20 or later. In some embodiments, the biological sample is collected from the pregnant woman prior to gestational week 30. In some embodiments, the risk of developing preeclampsia is the risk of developing preeclampsia within the following one, two, three or more weeks. In some embodiments, the PlGF-f:PlGF-d ratio is determined at least in part by: (a) determining a PlGF-f level by contacting a first PlGF probe to a first portion of the biological sample; and (b) determining a PlGF-d level by contacting the first PlGF probe to a second portion of the biological sample, wherein the first portion of the biological sample is untreated, and wherein a treatment is applied to the second portion of the biological sample, and wherein the treatment dissociates a PlGF complex. In some embodiments, the PlGF complex comprises PlGF and s-FLT. In some embodiments, the treatment is applied for at least 5, 10, 15, 20, 25, 30, 40, 50, 60, 90, or 120 minutes. In some embodiments, the treatment comprises increasing the temperature of the second portion of the biological sample. In some embodiments, the treatment comprises increasing the temperature to at least 30° C., at least 37° C., or at least 45° C. for at least 1 hour or at least 2 hours. In some embodiments, the treatment comprises increasing or decreasing the pH of the second portion of the biological sample. In some embodiments, the treatment comprises contacting the second portion of the biological sample with an agent that prevents PlGF from assembling into a PlGF complex. In some embodiments, the agent is selected from: a surfactant, a detergent, a chaotropic agent, a PlGF-binding protein, and an s-FLT-binding protein. In some embodiments, the first unmodified portion of the biological sample has not been stored at a temperature above about 20° C. In some embodiments, the method has a LLOQ for PlGF of 20 pg/ml or less. In some embodiments, the method comprises (a) determining a level of at least one secondary biomarker selected from total sFLT, free sFLT, Endoglin, KIM-1, FGF21, Decorin, Clec4A and CD274; and (b) determining the pregnant woman as being at risk or not at risk of preeclampsia by application of a trained algorithm to the PlGF-f:PlGF-d ratio in combination with the determined level least one of the secondary biomarker In some embodiments, the trained algorithm comprises a logistic regression, random forest, nearest centroid, gradient boosting method, linear discriminant analysis, neural network, or support vector machine algorithm. In some embodiments, the level of the at least one secondary biomarker is determined by an immunoassay. In some embodiments, the immunoassay is selected from a capture ELISA, an indirect ELISA, a TR-FRET assay, a proximity extension assay, an amplified luminescent proximity (LOCI) assay, a luminescent oxygen channeling immunoassay, or a lateral flow assay.

In some aspects, the present disclosure provides for a method for determining a PlGF-f:PlGF-d ratio in a biological sample comprising: (a) isolating a first aliquot of the biological sample for the detection of PlGF-f and a second aliquot of the biological sample for the detection of PlGF-d; (b) determining an amount of PlGF-f in the first aliquot; (b) applying a treatment to the second aliquot to dissociate PlGF complexes; and (c) determining an amount of PlGF-d in the second aliquot. In some embodiments, the biological sample has not been stored at a temperature above about 20° C. In some embodiments, the amount of PlGF-f and the amount of PlGF-d are determined using the same reagents. In some embodiments, the PlGF complex comprises PlGF and s-FLT. In some embodiments, the treatment is applied for at least 5, 10, 15, 20, 25, 30, 40, 50, 60, 90, or 120 minutes. In some embodiments, the treatment comprises increasing the temperature of the second portion of the biological sample. In some embodiments, the treatment comprises increasing the temperature to at least 30° C. for at least 1 hour. In some embodiments, the treatment comprises increasing or decreasing the pH of the second portion of the biological sample. In some embodiments, the treatment comprises contacting the second portion of the biological sample with an agent that prevents PlGF from assembling into a PlGF complex. In some embodiments, the agent is selected from: a surfactant, a detergent, a chaotropic agent, a PlGF-binding protein, and an s-FLT-binding protein. In some embodiments, the method has a LLOQ for PlGF of 20 pg/ml or less.

In some aspects, the present disclosure provides for a method for determining a PlGF-f:PlGF-d ratio in a biological sample comprising PlGF, the method comprising, (a) determining an amount of PlGF-f in a first aliquot of the biological sample by: (i) contacting the first aliquot with a capture reagent for a first time at a first temperature, wherein the PlGF-f binds to the capture reagent to form a PlGF-f-capture reagent complex; (ii) contacting the PlGF-f-capture reagent complex with a detector reagent for a second time at a second temperature, wherein the PlGF-f-capture reagent complex binds to the second reagent to form a first ternary complex comprising PlGF-f, the capture reagent, and the detector reagent; and (iii) detecting the first ternary complex; and (b) determining an amount of PlGF-d in a second aliquot of the biological sample by: (i) contacting the second aliquot with the capture reagent for a third time at a third temperature, wherein the PlGF-d binds to the capture reagent to form a PlGF-d-capture reagent complex; (ii) contacting the PlGF-d-capture reagent complex with the detector reagent for a fourth time at a fourth temperature, wherein the PlGF-d-capture reagent complex binds to the second reagent to form a second ternary complex comprising PlGF-d, the capture reagent, and the detector reagent; and (iii) detecting the second ternary complex; wherein a PlGF-s-Flt1 complex is stable at the first temperature and the PlGF-s-Flt1 complex dissociates at the second temperature. In some embodiments, (a) the first temperature is less than 30° C., less than 25° C., between 15° C. and 30° C., between 15° C. and 25° C., between 20° C. and 25° C., or about 22° C.; (b) the second temperature is less than 30° C., less than 25 C, between 15 C and 30 C, between 15° C. and 25° C., between 20° C. and 25° C., or about 22° C.; (c) the third temperature is at least 30° C., at least 35° C., between 30° C. and 45° C., about 30° C., about 37° C. or about 45° C.; (d) the fourth temperature is at least 30° C., at least 35° C., between 30° C. and 45° C., about 30° C., about 37° C. or about 45° C.; (e) the first time is less than 1 hour, less than 45 minutes, between 10 minutes and 30 minutes, about 30 minutes, about 20 minutes, or about 15 minutes; (f) the second time is less than 1 hour, less than 45 minutes, between 10 minutes and 30 minutes, about 30 minutes, about 20 minutes, or about 15 minutes; (g) the third time is at least 1 hour, between 1 hour and 3 hours, between 90 minutes and 150 minutes, or about 120 minutes; and (h) the fourth time is at least 1 hour, between 1 hour and 3 hours, between 90 minutes and 150 minutes, or about 120 minutes. In some embodiments, the first time is about 30 minutes, the second time is about 30 minutes, the third time is about 2 hours, the fourth time is about 2 hours, the first temperature is about 22° C., the second temperature is about 22° C., the third temperature is about 37° C., and the fourth temperature is about 37° C. In some embodiments, step b is conducted in the presence of a blocking antibody that prevents s-FLT from rebinding to PlGF. In some embodiments, the biological sample is blood, serum, plasma, amniotic fluid, or urine. In some embodiments, the biological sample is serum or plasma. In some embodiments, the biological sample is collected from a pregnant human female. In some embodiments, the pregnant human female has been pregnant for at least 20 weeks. In some embodiments, the pregnant human female has been pregnant for no more than 30 weeks. In some embodiments, the biological sample is stored at a storage temperature and the storage temperature never exceeds 30° C. In some embodiments, the storage temperature is less than 0° C. In some embodiments, the storage temperature is about −80° C. In some embodiments, the biological sample is diluted prior to step a. In some embodiments, the capture reagent comprises an antibody or an antigen-binding fragment thereof.

In some embodiments, the detector reagent comprises an antibody or an antigen-binding fragment thereof. In some embodiments, the capture reagent is attached to a solid support. In some embodiments, the detector reagent is attached to a solid support. In some embodiments, the detector reagent comprises a detectable label. In some embodiments, the label is a fluorophore, an enzyme, or an electrochemiluminescent tag. In some embodiments, (a)

further comprises contacting the first aliquot with a cross-linking agent that prevents the dissociation of a PlGF-sFLT complex.

In some aspects, the present disclosure provides for a method for determining a PlGF-f:PlGF-d ratio in a biological sample, wherein PlGF-f is determined using a reagent that can bind to PlGF-f but cannot bind to PlGF-d. In some embodiments, the reagent is an antibody or antigen-binding fragment thereof. In some embodiments, the reagent binds to residues on the PlGF-1 molecule that are involved in recognition of s-Flt-1.

In some aspects, the present disclosure provides for a method for determining a PlGF-f:PlGF-d ratio in a biological sample, wherein PlGF-d is determined using a reagent that can bind to PlGF-d but cannot bind to PlGF-f. In some embodiments, the reagent is an antibody or antigen-binding fragment thereof. In some embodiments, the reagent binds to the interface between PlGF and s-Flt-1.

In some aspects, the present disclosure provides for a method for determining a PlGF-f:PlGF-d ratio in a biological sample comprising separating the biological sample into a free PlGF component and a PlGF complex component, determining the amount of PlGF in the free PlGF component, and determining the amount of PlGF in the PlGF complex component. In some embodiments, the separating is performed by anion exchange chromatography, cation exchange chromatography, gel filtration chromatography or filtration. In some embodiments, the biological sample is contacted with a chemical crosslinking agent prior to the separating.

In some aspects, the present disclosure provides for a method of determining whether a pregnant human female is at risk of suffering from preeclampsia comprising: (a) determining a free Placental Growth Factor to dissociated Placental Growth Factor (PlGF-f:PlGF-d) ratio of a biological sample collected from the pregnant human female, wherein a PlGF-f:PlGF-d ratio less than a first threshold value indicates a heightened risk that the pregnant human female will suffer from preeclampsia, and wherein a PlGF-f:PlGF-d ratio greater than a second threshold value indicates a reduced risk that the pregnant human female will suffer from preeclampsia. In some embodiments, the first threshold value and the second threshold value are the same value. In some embodiments, the method comprises collecting the biological sample. In some embodiments, the biological sample is a fluid, whole blood, peripheral blood, serum, plasma, urine, or amniotic fluid sample. In some embodiments, the method further comprises collecting the biological sample via venipuncture, fingerstick sampling, or arterial sampling. In some embodiments, the biological sample is collected from the pregnant woman at gestational week 20 or later. In some embodiments, the biological sample is collected from the pregnant woman at gestational week 28 or later. In some embodiments, the biological sample is collected from the pregnant woman at gestational week 35 or later. In some embodiments, the biological sample is collected from the pregnant woman prior to gestational week 30. In some embodiments, the biological sample is collected from the pregnant woman prior to gestational week 37. In some embodiments, the biological sample is collected from the pregnant woman at gestational week 28 to 36 6/7. In some embodiments, the biological sample is collected from the pregnant woman at gestational week 35 to 36 6/7. In some embodiments, the risk of developing preeclampsia is the risk of developing preeclampsia within the following one, two, three or more weeks. In some embodiments, the risk of developing preeclampsia is the risk of developing preeclampsia within the following two weeks. In some embodiments, the PlGF-f:PlGF-d ratio is determined at least in part by: (a) determining a PlGF-f level by contacting a first PlGF probe to a first portion of the biological sample; and (b) determining a PlGF-d level by contacting the first PlGF probe to a second portion of the biological sample, wherein the first portion of the biological sample is untreated, and wherein a treatment is applied to the second portion of the biological sample wherein the treatment dissociates a PlGF complex. In some embodiments, the PlGF complex comprises PlGF and s-FLT. In some embodiments, the treatment is applied for at least 5, 10, 15, 20, 25, 30, 40, 50, 60, 90, or 120 minutes. In some embodiments, the treatment comprises increasing the temperature of the second portion of the biological sample. In some embodiments, the treatment comprises increasing the temperature to at least 30° C., at least 37° C., or at least 45° C. for at least 1 hour or at least 2 hours. In some embodiments, the treatment comprises increasing or decreasing the pH of the second portion of the biological sample. In some embodiments, the treatment comprises contacting the second portion of the biological sample with an agent that prevents PlGF from assembling into a PlGF complex. In some embodiments, the agent is selected from: a surfactant, a detergent, a chaotropic agent, a PlGF-binding protein, and an s-FLT-binding protein. In some embodiments, the first unmodified portion of the biological sample has not been stored at a temperature above about 20° C. In some embodiments, the method has a LLOQ for PlGF of 20 pg/ml or less. In some embodiments, the method further comprises (a) determining a level of at least one secondary biomarker selected from total sFLT, free sFLT, Endoglin, KIM-1, FGF21, Decorin, Clec4A and CD274; and (b) determining the pregnant woman as being at risk or not at risk of preeclampsia by application of a trained algorithm to the PlGF-f:PlGF-d ratio in combination with the determined level of the at least one secondary biomarker. In some embodiments, the trained algorithm comprises a logistic regression, random forest, nearest centroid, gradient boosting method, linear discriminant analysis, neural network, or support vector machine algorithm. In some embodiments, the level of the at least one secondary biomarker is determined by an immunoassay. In some embodiments, the immunoassay is selected from a capture ELISA, an indirect ELISA, a TR-FRET assay, a proximity extension assay, an amplified luminescent proximity (LOCI) assay, a luminescent oxygen channeling immunoassay, or a lateral flow assay. In some embodiments, the method further comprises proceeding with treatment of the pregnant human in a manner that avoids unnecessary treatment of preeclampsia comprises administering an anti-hypertensive drug or repeating (a) at a particular frequency. In some embodiments, the method further comprises administering an anti-hypertensive drug, wherein the antihypertensive drug is a central alpha agonist, a vasodilator, a calcium-channel blocker, an alpha-blocker, acetylsalicylic acid, or a beta-blocker.

In some aspects, the present disclosure provides for a method of determining whether a pregnant human female is at risk of suffering from preeclampsia comprising: (a) determining a level of at least PlGF-f. In some embodiments, a PlGF-f level less than a first threshold value indicates a heightened risk that the pregnant human female will suffer from preeclampsia. In some embodiments, a PlGF-f level greater than a second threshold value indicates a reduced risk that the pregnant human female will suffer from preeclampsia. In some embodiments, the first threshold value and the second threshold value are the same value. In some embodiments, the method further comprises determining a level of PlGF-d. In some embodiments, the method further comprises determining a ratio of PlGF-f to PlGF-d. In some embodiments, a ratio of PlGF-f to PlGF-d less than a first threshold value indicates a reduced risk the pregnant human female will suffer from preeclampsia. In some embodiments, a ratio of PlGF-f to PlGF-d greater than a second threshold value indicates an increased risk the pregnant human female will suffer from preeclampsia. In some embodiments, the method comprises collecting the biological sample. In some embodiments, the biological sample is a fluid, whole blood, peripheral blood, serum, plasma, urine, or amniotic fluid sample. In some embodiments, the method further comprises collecting the biological sample via venipuncture, fingerstick sampling, or arterial sampling. In some embodiments, the biological sample is collected from the pregnant woman at gestational week 20 or later. In some embodiments, the biological sample is collected from the pregnant woman at gestational week 28 or later. In some embodiments, the biological sample is collected from the pregnant woman at gestational week 35 or later. In some embodiments, the biological sample is collected from the pregnant woman prior to gestational week 30. In some embodiments, the biological sample is collected from the pregnant woman prior to gestational week 37. In some embodiments, the biological sample is collected from the pregnant woman at gestational week 28 to 36 6/7. In some embodiments, the biological sample is collected from the pregnant woman at gestational week 35 to 36 6/7. In some embodiments, the risk of developing preeclampsia is the risk of developing preeclampsia within the following one, two, three or more weeks. In some embodiments, the risk of developing preeclampsia is the risk of developing preeclampsia within the following two weeks. In some embodiments, the PlGF-f:PlGF-d ratio is determined at least in part by: (a) determining a PlGF-f level by contacting a first PlGF probe to a first portion of the biological sample; and (b) determining a PlGF-d level by contacting the first PlGF probe to a second portion of the biological sample, wherein the first portion of the biological sample is untreated, and wherein a treatment is applied to the second portion of the biological sample wherein the treatment dissociates a PlGF complex. In some embodiments, the PlGF complex comprises PlGF and s-FLT. In some embodiments, the treatment is applied for at least 5, 10, 15, 20, 25, 30, 40, 50, 60, 90, or 120 minutes. In some embodiments, the treatment comprises increasing the temperature of the second portion of the biological sample. In some embodiments, the treatment comprises increasing the temperature to at least 30° C., at least 37° C., or at least 45° C. for at least 1 hour or at least 2 hours. In some embodiments, the treatment comprises increasing or decreasing the pH of the second portion of the biological sample. In some embodiments, the treatment comprises contacting the second portion of the biological sample with an agent that prevents PlGF from assembling into a PlGF complex. In some embodiments, the agent is selected from: a surfactant, a detergent, a chaotropic agent, a PlGF-binding protein, and an s-FLT-binding protein. In some embodiments, the first unmodified portion of the biological sample has not been stored at a temperature above about 20° C. In some embodiments, the method has a LLOQ for PlGF of 20 pg/ml or less. In some embodiments, the method further comprises (a) determining a level of at least one secondary biomarker selected from total sFLT, free sFLT, Endoglin, KIM-1, FGF21, Decorin, Clec4A and CD274; and (b) determining the pregnant woman as being at risk or not at risk of preeclampsia by application of a trained algorithm to the PlGF-f:PlGF-d ratio in combination with the determined level of the at least one secondary biomarker. In some embodiments, the trained algorithm comprises a logistic regression, random forest, nearest centroid, gradient boosting method, linear discriminant analysis, neural network, or support vector machine algorithm. In some embodiments, the level of the at least one secondary biomarker is determined by an immunoassay. In some embodiments, the immunoassay is selected from a capture ELISA, an indirect ELISA, a TR-FRET assay, a proximity extension assay, an amplified luminescent proximity (LOCI) assay, a luminescent oxygen channeling immunoassay, or a lateral flow assay. In some embodiments, the method further comprises proceeding with treatment of the pregnant human in a manner that avoids unnecessary treatment of preeclampsia comprises administering an anti-hypertensive drug or repeating (a) at a particular frequency. In some embodiments, the method further comprises administering an anti-hypertensive drug, wherein the antihypertensive drug is a central alpha agonist, a vasodilator, a calcium-channel blocker, an alpha-blocker, acetylsalicylic acid, or a beta-blocker.

In some aspects, the present disclosure provides for a method of treating a pregnant human female comprising the steps of: determining whether the pregnant human female has an elevated risk of preeclampsia or reduced risk of preeclampsia by: obtaining a biological sample from the pregnant human female, determining a PlGF-f:PlGF-d ratio in the biological sample, and optionally determining a level of one or more secondary biomarkers in the biological sample; applying a classifier to the PlGF-f:PlGF-d ratio and, optionally, the level of one or more secondary biomarkers to classify the pregnant human female as having an elevated risk of preeclampsia or a reduced risk of preeclampsia; if the pregnant human female has an elevated risk of preeclampsia, then determining the blood pressure of the pregnant human female at a frequency of at least one time per week, and if the pregnant human female has a reduced risk of preeclampsia, then determining the blood pressure of the pregnant human female at a frequency of less than one time per week. In some embodiments, the pregnant human female is determined to not have an elevated risk of preeclampsia, then administering an antihypertensive drug to the pregnant human female. In some embodiments, the antihypertensive drug is a central alpha agonist, a vasodilator, a calcium-channel blocker, an alpha-blocker, acetylsalicylic acid, or a beta-blocker. In some embodiments, the antihypertensive drug is methyldopa, labetalol, nifedipine, verapamil, clonidine, hydralazine, diazoxide, prazosin, or oxprenolol. In some embodiments, the method further comprises administering a cervical ripening or labor-inducing agent to the pregnant woman when the pregnant woman is determined to be at risk of suffering from preeclampsia. In some embodiments, the cervical ripening or labor-inducing agent comprises a prostaglandin, oxytocin, misoprostol, mifepristone, or relaxin.

In some aspects, the present disclosure provides for a method of treating a pregnant human female comprising the steps of: determining whether the pregnant human female has an elevated risk of preeclampsia or reduced risk of preeclampsia by: obtaining a biological sample from the pregnant human female, determining a level of at least PlGF-f in the biological sample, and optionally determining a level of one or more secondary biomarkers in the biological sample. In some embodiments, the method further comprises applying a classifier to the PlGF-f level and, optionally, the level of one or more secondary biomarkers to classify the pregnant human female as having an elevated risk of preeclampsia or a reduced risk of preeclampsia. In some embodiments, the method further comprises determining a level of PlGF-d and applying a classifier to the PlGF-d level. In some embodiments, if the pregnant human female has an elevated risk of preeclampsia, then the method comprises determining the blood pressure of the pregnant human female at a frequency of at least one time per week. In some embodiments, if the pregnant human female has a reduced risk of preeclampsia, then the method further comprises determining the blood pressure of the pregnant human female at a frequency of less than one time per week. In some embodiments, when the pregnant human female is determined to not have an elevated risk of preeclampsia, then the method further comprises administering an antihypertensive drug to the pregnant human female. In some embodiments, the antihypertensive drug is a central alpha agonist, a vasodilator, a calcium-channel blocker, an alpha-blocker, acetylsalicylic acid, or a beta-blocker. In some embodiments, the antihypertensive drug is methyldopa, labetalol, nifedipine, verapamil, clonidine, hydralazine, diazoxide, prazosin, or oxprenolol. In some embodiments, the method further comprises administering a cervical ripening or labor-inducing agent to the pregnant woman when the pregnant woman is determined to be at risk of suffering from preeclampsia. In some embodiments, the cervical ripening or labor-inducing agent comprises a prostaglandin, oxytocin, misoprostol, mifepristone, or relaxin.

In some aspects, the present disclosure provides for a method for avoiding unnecessary treatment of preeclampsia, the method comprising: (a) contacting a biological sample that has been collected from a pregnant human female with a plurality of different antigen-specific probes to determine levels of two or more markers, wherein the two or more markers comprise at least PlGF-f and PlGF-d; and (b) proceeding with treatment of the pregnant human in a manner that avoids unnecessary treatment of preeclampsia based at least in part on the amounts or concentrations of the markers determined in (a). In some embodiments, the two or more markers comprise three or more markers further comprising at least one of sFLT, Endoglin, KIM-1, FGF21, or free sFLT.

In some aspects, the present disclosure provides for a system for ruling out preeclampsia in a pregnant female subject for a specified period of time, the system comprising: a processor; an input module for inputting levels of at least two markers in a biological sample, wherein the at least two markers comprise at least PlGF-f and PlGF-d; and a computer readable medium containing instructions that, when executed by the processor, performs a first algorithm on the input levels of the at least two markers. In some embodiments, the at least two markers comprise at least three markers that further comprise at least one of sFLT, Endoglin, KIM-1, FGF21, or free sFLT. In some embodiments, the system further comprises an output module providing one or more indicia based on the input levels of the at least three markers, wherein the one or more indicia are indicative of the subject not having preeclampsia for at least a specified period of time.

In some aspects, the present disclosure provides for a method for determining levels of free and dissociated PlGF in a biological sample from a subject, the method comprising: (a) isolating a first aliquot of the biological sample for the detection of PlGF-f and a second aliquot of the biological sample for the detection of PlGF-d; (b) determining an amount of PlGF-f in the first aliquot; (c) applying a treatment to the second aliquot to dissociate PlGF complexes; and (d) determining an amount of PlGF-d in the second aliquot. In some embodiments, the method further comprises determining a ratio of the amounts of PlGF-f and PlGF-d. In some embodiments, the biological sample has not been stored at a temperature above about 20° C. In some embodiments, the amount of PlGF-f and the amount of PlGF-d are determined using same reagents. In some embodiments, the PlGF complex comprises PlGF and s-FLT. In some embodiments, the treatment is applied for at least 5, 10, 15, 20, 25, 30, 40, 50, 60, 90, or 120 minutes. In some embodiments, the treatment comprises increasing the temperature of the second portion of the biological sample. In some embodiments, the treatment comprises increasing the temperature to at least 30° C. for at least 1 hour. In some embodiments, the treatment comprises increasing or decreasing the pH of the second portion of the biological sample. In some embodiments, the treatment comprises contacting the second portion of the biological sample with an agent that prevents PlGF from assembling into a PlGF complex or disables PlGF from a PlGF:sFLT1 complex. In some embodiments, the agent is selected from: a surfactant, a detergent, a chaotropic agent, a PlGF-binding protein, and an s-FLT-binding protein. In some embodiments, the method has a LLOQ for PlGF of 20 pg/ml or less.

In some aspects, the present disclosure provides for a method for determining free and dissociated PlGF amounts in a biological sample comprising PlGF, the method comprising: (a) determining an amount of PlGF-f in a first aliquot of the biological sample by: (i) contacting the first aliquot with a capture reagent for a first time at a first temperature, wherein the PlGF-f binds to the capture reagent to form a PlGF-f-capture reagent complex; (ii) contacting the PlGF-f-capture reagent complex with a detector reagent for a second time at a second temperature, wherein the PlGF-f-capture reagent complex binds to the second reagent to form a first ternary complex comprising PlGF-f, the capture reagent, and the detector reagent; and (iii) detecting the first ternary complex; and (b) determining an amount of PlGF-d in a second aliquot of the biological sample by: (i) contacting the second aliquot with the capture reagent for a third time at a third temperature, wherein the PlGF-d binds to the capture reagent to form a PlGF-d-capture reagent complex; (ii) contacting the PlGF-d-capture reagent complex with the detector reagent for a fourth time at a fourth temperature, wherein the PlGF-d-capture reagent complex binds to the second reagent to form a second ternary complex comprising PlGF-d, the capture reagent, and the detector reagent; and (iii) detecting the second ternary complex; wherein a PlGF-s-Flt1 complex is stable at the first temperature and the PlGF-s-Flt1 complex dissociates at the third temperature. In some embodiments: (a) the first temperature is less than 30° C., less than 25° C., between 15° C. and 30° C., between 15° C. and 25° C., between 20° C. and 25° C., or about 22° C.; (b) the second temperature is less than 30 C, less than 25 C, between 15 C and 30 C, between 15° C. and 25° C., between 20° C. and 25° C., or about 22° C.; (c) the third temperature is at least 30° C., at least 35° C., between 30° C. and 45° C., about 30° C., about 37° C. or about 45° C.; (d) the fourth temperature is at least 30° C., at least 35° C., between 30° C. and 45° C., about 30° C., about 37° C. or about 45° C.; (e) the first time is less than 1 hour, less than 45 minutes, between 10 minutes and 30 minutes, about 30 minutes, about 20 minutes, or about 15 minutes; (f) the second time is less than 1 hour, less than 45 minutes, between 10 minutes and 30 minutes, about 30 minutes, about 20 minutes, or about 15 minutes; (g) the third time is at least 1 hour, between 1 hour and 3 hours, between 90 minutes and 150 minutes, or about 120 minutes; or (h) the fourth time is at least 1 hour, between 1 hour and 3 hours, between 90 minutes and 150 minutes, or about 120 minutes. In some embodiments, the first time is about 30 minutes, the second time is about 30 minutes, the third time is about 2 hours, the fourth time is about 2 hours, the first temperature is about 22° C., the second temperature is about 22° C., the third temperature is about 37° C., and the fourth temperature is about 37° C. In some embodiments, step b is conducted in the presence of a blocking antibody that prevents s-FLT from rebinding to PlGF. In some embodiments, the biological sample is blood, serum, plasma, amniotic fluid, or urine. In some embodiments, the biological sample is serum or plasma. In some embodiments, the biological sample is collected from a pregnant human female. In some embodiments, the pregnant human female has been pregnant for at least 20 weeks. In some embodiments, the pregnant human female has been pregnant for no more than 30 weeks. In some embodiments, the biological sample is stored at a storage temperature and the storage temperature never exceeds 30° C. In some embodiments, the storage temperature is less than 0° C. In some embodiments, the storage temperature is about −80° C. In some embodiments, the biological sample is diluted prior to step a. In some embodiments, the capture reagent comprises an antibody or an antigen-binding fragment thereof. In some embodiments, the detector reagent comprises an antibody or an antigen-binding fragment thereof. In some embodiments, the capture reagent is attached to a solid support. In some embodiments, the detector reagent is attached to a solid support. In some embodiments, the detector reagent comprises a detectable label. In some embodiments, the label is a fluorophore, an enzyme, or an electrochemiluminescent tag. In some embodiments, (a) further comprises contacting the first aliquot with a crosslinking agent that prevents the dissociation of a PlGF-sFLT complex.

In some aspects, the present disclosure provides for a method for determining a PlGF-f:PlGF-d ratio in a biological sample, wherein PlGF-f is determined using a reagent that can bind to PlGF-f but cannot bind to PlGF-d. In some embodiments, the reagent is an antibody or antigen-binding fragment thereof. In some embodiments, the reagent binds to residues on the PlGF-1 molecule that are involved in recognition of sFlt-1.

In some aspects, the present disclosure provides for a method for determining a PlGF-f:PlGF-d ratio in a biological sample, wherein PlGF-d is determined using a reagent that can bind to PlGF-d but cannot bind to PlGF-f. In some embodiments, the reagent is an antibody or antigen-binding fragment thereof. In some embodiments, the reagent binds to an interface between PlGF and sFlt-1.

In some aspects, the present disclosure provides for a method for determining free and dissociated PlGF amounts in a biological sample comprising separating the biological sample into a free PlGF component and a PlGF complex component, determining the amount of PlGF in the free PlGF component, and determining the amount of PlGF in the PlGF complex component. In some embodiments, the separating is performed by anion exchange chromatography, cation exchange chromatography, gel filtration chromatography or filtration. In some embodiments, the biological sample is contacted with a chemical crosslinking agent prior to the separating.

In some aspects, the present disclosure provides for a kit for assessing a risk of preeclampsia or ruling out preeclampsia in a pregnant female subject, the kit comprising: (a) an agent or apparatus for dissociating placental growth factor (PLGF) from a PLGF complex with another protein; and (b) at least one probe for specific binding to placental growth factor (PlGF). In some embodiments, the kit is designed to measure the levels of no more than 20, no more than 15, no more than 10, nor more than 8, no more than 7, no more than 6, nor more than 5, or no more than 4 proteins. In some embodiments, the kit is further designed to measure the levels of at least one of sFLT, Endoglin, KIM-1, FGF21, or free sFLT In some embodiments, the kit further comprises at least one probe for specific binding to at least one of sFLT, Endoglin, KIM-1, FGF21, or free sFLT In some embodiments, the kit further comprises instructions for carrying out an immunoassay. In some embodiments, the kit is an enzyme-linked immunosorbent assay kit. In some embodiments, one or more of the probes are attached to a substrate. In some embodiments, the kit is for a lateral flow immunoassay. In some embodiments, the kit further comprises a collection tube for collecting a biological sample from the pregnant female subject. In some embodiments, the collection tube is a collection tube suitable for collection of serum or plasma. In some embodiments, the at least one probe for specific binding to PlGF or the least one probe for specific binding to at least one of sFLT, Endoglin, KIM-1, FGF21, or free sFLT comprises an antibody or antigen-binding fragment or derivative thereof. In some embodiments, the kit further comprising a microwell or multiwell plate. In some embodiments, the microwell or multiwell plate comprises at least one well with the at least one probe for specific binding to PlGF or the least one probe for specific binding to at least one of sFLT, Endoglin, KIM-1, FGF21, or free sFLT conjugated to a surface therein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, which are summarized below. In these figures and the subsequent detailed description, PlGF(f) or PlGF-f refers to free Placental Growth Factor (PlGF), and PlGF(d) or PlGF-d refers to disassociated PlGF as defined herein.

FIGS. 1A and 1B depict schemes showing the species of PlGF predicted to be present in pregnant patient serum samples (A), as well as the predicted behavior of these species in sandwich ELISA assays (B). PlGF species can include free PlGF (e.g., in dimerized form), PLGF (2:1) (e.g., PlGF dimer and single sFLT molecule), and PlGF(2:2) (e.g., PlGF dimer and two sFLT molecules).

FIGS. 4A, 4B, 4C, and 4D illustrate the effects of various capture times and sFLT concentrations on the detection of PlGF using 3rd trimester pregnancy samples.

FIG. 6 shows plots of PE and non-PE patients from the studies segregated using PlGF(f) conc or % free PlGF ((f)/(d)×100) demonstrating that both metrics separate PE samples from non-PE samples and % free PlGF shows improved separation. In this figure blue dot indicates Non-PE, orange dot indicates PE, grey dot indicates PE from 104 cohort, and * indicates below LLOQ.

FIGS. 15A and 15B show the different definitions of clinical categories used in cross-sectional and forward-looking "rule out" analyses performed in Examples 5 and 7.

DETAILED DESCRIPTION OF THE INVENTION

Figure 2B:
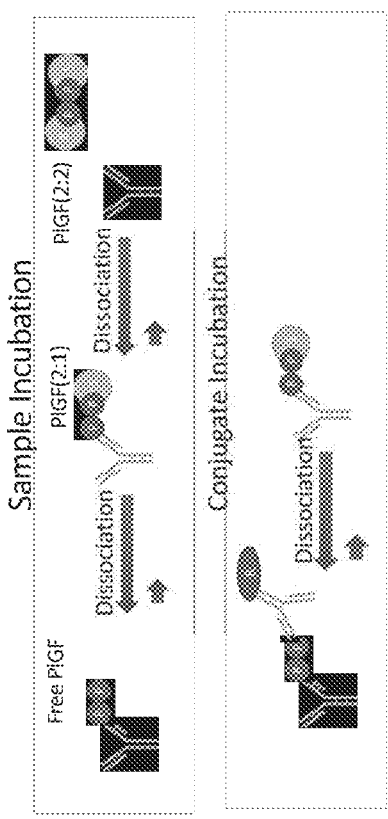
FIGS. 2A and 2B illustrate the change in measured PlGF concentration of PE and Non-PE samples incubated at various capture/detection temperatures (A), as well as the predicted behavior of different PlGF species during sample capture and detection incubation (B).

Detection of preeclampsia using the classic clinical symptoms of the disease is error-prone, risking significant adverse outcome for patients and an added burden to the healthcare system through misdiagnosis. Measurement of proteinuria is prone to inaccuracies (e.g., false negatives and false positives), preeclampsia complications may occur before proteinuria becomes significant, the clinical presentation of preeclampsia can be highly variable in progression rate, onset time, and severity, and the symptoms (hypertension, proteinuria, or both) can be indicative of other distinct disorders that could utilize a less aggressive treatment course (chronic hypertension, gestational hypertension, temporary high blood pressure, and gestational diabetes). Thus, there is significant risk for patients with only suspected preeclampsia to be over treated (e.g., delivered or induced early, thereby unnecessarily putting the infant at risk of preterm birth complications and/or unnecessarily putting the mother at risk of surgical complications), and there is risk for patients with silent or rapidly-progressing preeclampsia to be treated insufficiently aggressively, thereby putting the infant at risk of intrauterine growth restriction or death, and the mother at risk of preeclamptic sequelae such as eclampsia seizures, renal or liver damage, pulmonary edema, placental abruption, and coma).

Application of the sFlt1/PlGF ratio in patient serum as a method for identifying preeclampsia would seem to mitigate these problems, except that this method has limited sensitivity and specificity (see e.g., Zeisler et al. NEJM 274 (2017):13-22 or Verlohren et al. Hypertension. 63(2014): 346-52, where the method was identified as having maximal sensitivity of 80% and specificity of 78.3%) and thus involves a significant proportion of false negatives and false positives, making it of limited use in ruling out a diagnosis of preeclampsia and avoiding the overtreatment/under treatment conundrum.

Accordingly, there is a need for the methods, compositions, systems and kits for improved detection or prediction of preeclampsia in pregnant patients, particularly those that enable the detection or prediction of preeclampsia with a high negative predictive value and/or allow medical professionals to rule out a diagnosis of preeclampsia for an extended period of time.

Definitions

As used in the specification and in the claims, the singular form "a," "an," and "the" include plural referents unless the context clearly dictates otherwise.

The term "hypertension" refers to abnormally high blood pressure. Hypertension can be identified in any suitable manner, such as by reference to a sitting systolic blood pressure (sSBP) of greater than 140 mmHg or a sitting diastolic blood pressure (sDBP) of greater than 90 mmHg. Hypertension can be further classified into class 1 or class 2 hypertension, with class 1 exhibiting sSBP of 140-149 mmHg or 90-99 mmHg sDBP, and class 2 exhibiting greater than 160 mmHg sSBP or 100 mmHg sDBP. (See, e.g., The Seventh Report of the Joint National Committee on Prevention, Detection, Evaluation, and Treatment of High Blood Pressure. JAMA 2003; 289:2560-71.) Other suitable criteria may be used to identify hypertension, such as having a sitting systolic blood pressure of greater than 130 and/or a sitting diastolic blood pressure of greater than 90 mmHg. Hypertension can also be determined according to the 2017 AHA guidelines (see Whelton et al. 2017 ACC/AHA/AAPA/ABC/ACPM/AGS/APhA/ASH/ASPC/NMA/PCNA Guideline for the Prevention, Detection, Evaluation, and Management of High Blood Pressure in Adults, Journal of the American College of Cardiology (2017), doi: 10.1016/j.jacc.2017.11.006). Such guidelines identify "normal" blood pressure as less than 120/80 mmHg, "elevated" as systolic between 120-129 mmHg and diastolic less than 80 mmHg, "stage 1" as systolic between 120-139 mmHg or diastolic between 80-89 mmHg, "stage 2" as systolic at least 140 mmHg or diastolic at least 90 mmHg, and "hypertensive crisis" as systolic over 180 and/or diastolic over 120.

As used herein, the term "proteinuria" is defined as the presence of abnormal protein in the urine. A number of indicator dyes and reagents can used to measure proteinuria semi-quantitatively (e.g., bromophenol blue). In some embodiments, concentrations of protein in urine can be determined by a semi quantitative "dipstick" analysis and graded as negative, trace (10-20 mg/dL), 1+(~30 mg/dL), 2+(~100 mg/dL), 3+(~300 mg/dL), or 4+(~1,000 mg/dL), with 2+ commonly being used as the threshold for problematic proteinuria. In an alternative scheme, concentrations of protein in urine can also be measured per 24-hour urine collection, in which greater than or equal to 300 mg protein indicates proteinuria. In an alternative scheme, concentrations of protein in urine can be measured in a spot urine sample, in which 30 mg of protein per deciliter or greater indicates proteinuria. In yet an alternative scheme, proteinuria can also be expressed as the protein/creatinine ratio (Pr/Cr) in urine, in which a Pr/Cr ratio of >0.3 is indicative of problematic proteinuria.

As used herein, the term "antibody or fragments thereof" is used in the broadest sense and specifically encompasses intact monoclonal antibodies, polyclonal antibodies, multispecific antibodies (e.g. bispecific antibodies formed from at least one binding domain of two intact antibodies), and antibody fragments. Antibody fragments comprise a portion of an intact antibody that retains antigen-binding activity; examples include Fab, Fab', $F(ab)_2$, $F(abc)_2$, and Fv fragments as well as diabodies, linear antibodies, scFvs, and multispecific antibodies formed from antibody fragments.

As used herein, the term "preeclampsia" ("PreE" or "PE") refers to a pregnancy-specific disorder involving multiple organ systems thought to originate from abnormal placentation, dysfunctional trophoblast development, defective placental angiogenesis, and a heightened systemic inflammatory response in the mother. Preeclampsia, when untreated, can progress to ecclampsia, HELLP syndrome, hemorrhagic or ischemic stroke, liver damage, acute kidney injury, and acute respiratory distress syndrome (ARDS). Thus, while preeclampsia frequently presents with symptoms such as hypertension and proteinuria, it is distinct from simple vascular tension disorders and kidney dysfunction (as evidenced by the non-overlapping set of complications that result when it is untreated), and symptoms reflective of vascular tension disorders and kidney dysfunction on their own therefore have less than ideal predictive/diagnostic value for preeclampsia. Further information on the pathophysiology of preeclampsia can be found, e.g., in Phipps et al. Clin J Am Soc Nephrol 11(2016):1102-1113. In some embodiments, a traditional diagnosis of preeclampsia is made when hypertension and proteinuria as defined above are detected at the same time. In other embodiments (see American College of Obstetricians and Gynecologists; Task Force on Hypertension in Pregnancy. Obstet Gynecol. 122 (2013):1122-31, which is explicitly incorporated by reference herein) a traditional diagnosis of preeclampsia is made upon simultaneous detection of hypertension (blood pressure greater than or equal to 140 mmHg systolic or greater than or equal to 90 mmHg diastolic on two occasions at least 4 hours apart after 20 weeks gestation in a woman with a previously normal blood pressure, or blood pressure with greater than equal to 160 mmHg systolic or greater than or equal to 110 mmHg diastolic within a short interval of minutes) and proteinuria (greater than or equal to 300 mg per 24-hour urine collection either measured or extrapolated, or protein creatinine ratio greater than or equal to 0.3, or a dipstick reading of 1+(pre-2013 guidelines) or 2+(post-2013 guidelines))) or upon new onset hypertension in the absence of proteinurea when (a) blood platelet count is less than 100,000 per milliliter, (b) serum creatinine is greater than 1.1 mg/dL or double baseline for the patient, or (c) blood concentration of liver transaminases is twice normal or greater). In some cases, preeclampsia is made without a diagnosis of proteinurea, for instance where evidence of other end-stage organ damage is present.

The term "subject" can include human or non-human animals. Thus, the methods and described herein are applicable to both human and veterinary disease and animal models. Preferred subjects are "patients," i.e., living humans that are receiving medical care for a disease or condition. This includes persons with no defined illness who are being investigated for signs of pathology.

The term "unnecessary treatment of preeclampsia" can refer to treatments for preeclampsia that would be, statistically speaking, unjustified when a practitioner considers the results of a test or procedure described herein, such as a test based on the determination of an amount of concentration of various protein biomarkers. Such unnecessary treatment can include preterm induction based on one or more symptoms or risk factors for preeclampsia.

The term PlGF refers to Placental Growth Factor. PlGF is also referred to as PlGF or PIGF and is encoded by the PGF gene. PlGF includes at least four known isoforms: PlGF-1, PlGF-2, PlGF-3, and PlGF-4.

The term sFLT or sFLT1 refers to the soluble ectodomain of Fms-like tyrosine kinase 1, also known as Vascular Endothelial Growth Factor Receptor 1, FLT-1, FLT1, FRT, or VEGFR1. The term "free PlGF" (also "PlGF(f)" or "PlGF-f") refers to PlGF in a biological sample not complexed another other binding partner. In some embodiments, the other binding partner is sFLT1, with which it can form at least two complexes with PlGF:2:2 sFLT:PlGF and 2:1 sFLT:PlGF complexes.

The term "dissociated PlGF" (also "PlGF(d)" or "PlGF-d") refers to PlGF that has been dissociated from its binding partners in a biological sample by subsequent in vitro treatment. In some embodiments, the other binding partner is sFLT1, with which it can form at least 2:2 sFLT:PlGF and 2:1 sFLT:PlGF complexes. In some embodiments, when treatment is sufficient to dissociate substantially all PlGF complexes with another protein (such as sFLT1), "dissociate PlGF" is equal to "total PlGF" (e.g. the total level of PlGF present in the biological sample).

Subjects

In some embodiments, the methods, compositions, systems and kits provided herein are used for detecting or predicting a condition in a pregnant human subject at any stage in pregnancy. In other embodiments, the pregnant human subject is post-the $20^{th}$ week of gestation. In other embodiments, the pregnant human subject is post-first or -second trimester of pregnancy. In some embodiments, the pregnant human subject is post- or equal to the $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, or $42^{nd}$ week of gestation, or any range between these values.

The methods, compositions, systems and kits are suitable for detecting or predicting a condition of the pregnant subject such as preeclampsia (PreE) or non-preeclampsia (NonPreE). In some embodiments, preeclampsia is further divided into very early-onset (before 25 weeks gestation), early-onset (before 34 weeks gestation) and late-onset (after 34 weeks gestation) preeclampsia. Typically, when the pregnant patient does not exhibit hypertensive or renal symptoms, the patient is considered NonPreE. Further, when the pregnant patient exhibits only hypertensive symptoms alone without signs of proteinuria, the patient is generally only suspected to have preeclampsia. However, as the measurement of proteinuria is prone to inaccuracies (e.g., false negatives and false positives), preeclampsia complications may occur before proteinuria becomes significant, the clinical presentation of preeclampsia can be highly variable (from severe, rapidly progressing, and early-onset to late-onset and less severe), and the symptoms (hypertension, proteinuria, or both) can be indicative of other distinct disorders that could utilize a different treatment course. Thus, there is significant risk for patients with only suspected preeclampsia to be unnecessarily treated (e.g., delivered/induced early putting the infant at risk of preterm birth complications or the mother at risk of surgical complications), and there is risk for patients with silent or rapidly-progressing preeclampsia to be treated insufficiently aggressively (e.g., putting the infant at risk of intrauterine growth restriction or death, and the mother at risk of preeclampsia sequelae such as eclampsia seizures, renal or liver damage, pulmonary edema, placental abruption, and coma).

A subject therefore can be a pregnant female that has no known risk factors or has one or more at-risk factors for a condition such as PreE. In some instances, hypertension and/or proteinuria can indicate a subject at risk of preeclampsia. In some instances, a subject at risk of preeclampsia can have a urine protein content measured as 2+(100 mg/dL) or greater by dipstick assay, greater than or equal to 300 mg per 24-hour urine collection, 30 mg of protein per deciliter or greater in a spot urine sample, or a Pr/Cr ratio in urine of >30 mg per millimole. In some instances, a subject at risk of preeclampsia can have a sitting systolic blood pressure (sSBP) of greater than 140 mmHg or a sitting diastolic blood pressure (sDBP) of greater than 90 mmHg or both. In some instances, sFlt1/PlGF ratio can be used to identify subject at risk of preeclampsia (see, e.g., Zeisler et al. NEJM 274 (2017):13-22 or Verlohren et al. Hypertension. 63(2014): 346-52). In some instances, both hypertension and proteinuria can be used to identify a subject at risk of preeclampsia. In some instances, new onset hypertension in combination with one or more symptoms selected from (a) blood platelet count is less than 100,000 per milliliter, (b) serum creatinine is greater than 1.1 mg/dL or double baseline for the patient, or (c) blood concentration of liver transaminases is twice normal or greater can be used to identify a subject at risk of preeclampsia.

Samples

Methods for detecting molecules (e.g., nucleic acids, proteins, etc.) in a pregnant subject in order to detect, diagnose, monitor, predict, or evaluate the status or outcome of the pregnancy are described in this disclosure. In some cases, the molecules are circulating molecules (e.g. unbound to cells and freely circulating in bodily fluids such as blood, blood plasma or blood serum). In some cases, the molecules are expressed in the cytoplasm of blood, endothelial, or organ cells. In some cases, the molecules are expressed on the surface of blood, endothelial, or organ cells.

The methods, kits, and systems disclosed herein can be used to classify one or more samples from one or more subjects. A sample can be any material containing tissues, cells, nucleic acids, genes, gene fragments, expression products, proteins, polypeptides, exosomes, gene expression products, or gene expression product fragments of a subject to be tested. A sample can include but is not limited to, tissue, cells, plasma, serum, or any other biological material from cells or derived from cells of an individual. The sample can be a heterogeneous or homogeneous population of cells or tissues. The sample can be a fluid that is acellular or depleted of cells (e.g., plasma or serum). In some cases, the sample is from a single patient. In some cases, the method comprises analyzing multiple samples at once, e.g., via massively parallel multiplex expression analysis on protein arrays or the like.

The sample is preferably a bodily fluid. The bodily fluid can be saliva, urine, blood, and/or amniotic fluid. The sample can be a fraction of any of these fluids, such as plasma, serum or exosomes (exemplary exosome isolation techniques can be found, e.g. in Li et al. Theranostics. 7(2017): 789-804). In preferred embodiments, the sample is a blood sample, plasma sample, or serum sample.

The sample may be obtained using any method that can provide a sample suitable for the analytical methods described herein. The sample may be obtained by a non-invasive method such as a throat swab, buccal swab, bronchial lavage, urine collection, scraping of the cervix, cervicovaginal sample secretion collection (e.g. with an ophthalmic sponge such as a Weck-Cel sponge), saliva collection, or feces collection. The sample may be obtained by a minimally-invasive method such as a blood draw. The sample may be obtained by venipuncture.

As used herein "obtaining a sample" includes obtaining a sample directly or indirectly. In some embodiments, the sample is taken from the subject by the same party (e.g. a testing laboratory) that subsequently acquires biomarker data from the sample. In some embodiments, the sample is received (e.g. by a testing laboratory) from another entity that collected it from the subject (e.g. a physician, nurse, phlebotomist, or medical caregiver). In some embodiments, the sample is taken from the subject by a medical professional under direction of a separate entity (e.g. a testing laboratory) and subsequently provided to said entity (e.g. the testing laboratory). In some embodiments, the sample is taken by the subject or the subject's caregiver at home and subsequently provided to the party that acquires biomarker data from the sample (e.g. a testing laboratory). A variety of kits suitable for self or home collection of biological samples have been described commercially and in the literature; see e.g., US20170023446A1 and U.S. Pat. No. 4,777,964A.

Sample Data

The methods, kits, and systems disclosed herein may comprise data pertaining to one or more samples or uses thereof. The data can be representative of an amount or concentration of one or more biomarkers, such as various proteins described herein. Stated differently, the data can be expression level data of proteins or polypeptides. The expression level data of biomarkers described herein can be determined by protein array, proteomics, expression proteomics, mass spectrometry (e.g., liquid chromatography-mass spectrometry (LC-MS), multiple reaction monitoring (MRM), selected reaction monitoring (SRM), scheduled MRM, scheduled SRM), 2D PAGE, 3D PAGE, electrophoresis, proteomic chip, proteomic microarray, Edman degradation, direct or indirect ELISA, immunosorbent assay, immuno-PCR (see, e.g., Sano et al. Science. 258(1992):120-2.), proximity extension assay (see, e.g., Thorsen et al. Journal of Translational Medicine. 11(2013):253, US20130288249A1, U.S. Pat. No. 9,777,315B2), Luminex assay, or homogenous assays such as ALPHAscreen (see, e.g., Application Note. Nature Methods 5, (2008), U.S. Pat. No. 5,898,005A, 5,861,319A), time-resolved fluorescence resonance energy transfer (TR-FRET see e.g., US20130203068A1 and WO1998015830A2), time-resolved fluorescence (TRF), fluorescent oxygen channeling immunoassay (FOCI), or luminescent oxygen channeling immunoassay (LOCI™; see e.g. Ullman et al. Proc Natl Acad Sci USA. 91(1994):5426-5430 or Ullman et al. Clin Chem. 1996 September; 42(9):1518-26 for exemplary methods and reagents).

In some embodiments, the compositions, methods and devices described herein make use of labeled molecules in various sandwich, competitive, or non-competitive assay formats to determine expression levels of biomarkers described herein. Such methods generate a signal that is related to the presence or amount of one or more of the proteins described herein. Suitable assay formats also include chromatographic, mass spectrographic, and protein "blotting" methods. Additionally, certain methods and devices, such as biosensors, optical immunoassays, immunosorbent assays, and enzyme immunoassays, may be employed to determine the presence or amount of analytes without the need for a labeled molecule. Examples of enzyme immunoassays (EIA) include chemiluminescent enzyme immunoassay, electrochemiluminescence immunoassay (ECLIA), and enzyme-linked immunosorbent assay (ELISA), which are further described by Kuhle, Jens, et al. "Comparison of three analytical platforms for quantification of the neurofilament light chain in blood samples: ELISA, electrochemiluminescence immunoassay and Simoa." Clinical Chemistry and Laboratory Medicine (CCLM) 54.10 (2016): 1655-1661. Robotic instrumentation for performing these immunoassays are commercially available including, but not limited to Abbott AXSYM®, IMx®, or Commander® systems; Biolog 24i® or CLC480 systems; Beckman Coulter ACCESS®, ACCESS 2®, or Unicel Dxl 600/800 systems; bioMerieux VIDAS® or mini-VIDAS® systems; Chimera Biotec GmbH Imperacer® assay; Dade Behring STRATUS® system; DiaSorin LIAISON XL® or ETI-Max 300 systems; Dynex Agility® system; Gold Standard Diagnostics Thunderbolt® analyzer; Gyrolab xPlore/xPand® system; Hudson Robotics ELISA Workstation; Ortho Clinical Diagnostics Vitros® ECL or 3600 systems; Hamiltorn Robotics ELISA NIMBUS or STARlet systems; Luminex xMAP® system; PerkinElmer ALPHAscreen® or AlphaLISA®; Phadia Laboratory System 100E, 250, 1000, 2500, or 5000; Quanterix SIMOA® system; Quidel Sofia®2 POC systems; Radiometer AQT90 Flex system; Roche Diagnostics ElecSys® 2010, Cobas® 4000/6000/8000 Analyzers, or Integra® 400 Plus; c111, c311, c501, c502 family of analyzers; Seikisui Diagnostics FastPack® IP automated system; Siemens Dimension Vista® 1500 System, DPC Immulite 1000/2000 system, or DCA Vantage® Analyzer; Singulex Single Molecule Counting (SMC™) assay; Stratus® CS Acute Care Diagnostic System; Sysmex Eurolyser®; ThermoFisher MGC 240 Benchtop Analyzer; Tosoh Bioscience AIA®-360 or AIA-600II systems; UniCel Dxl 860i Synchron Access Clinical System, UniCel DxC 680i Synchron Access Clinical System, Access/Access 2 Immunoassay System, 600 Access Immunoassay System, 600i Synchron Access Clinical System, Dxl 800 Access Immunoassay System, DxC 880i Synchron Access Clinical System; and Vital Diagnostics PathFast® point-of-care chemiluminescence immunoassay analyzer. But any suitable immunoassay may be utilized, for example, enzyme-linked immunoassays (ELISA), radioimmunoassays (RIAs), competitive binding assays, and the like.

Other exemplary analytical systems include assay systems, such as, for example, optical systems containing one or more sources of radiation and/or one more detector. Such systems may use, for example, a light source that illuminates and a sample and a detector configured to detect light that is emitted by the sample (e.g., fluorescence spectroscopy), optical density (e.g., the portion of light that passes through the sample), and/or light that is diffracted by sample (e.g., diffraction optics). An analytical system may use, for example, ELISA (enzyme-linked immunosorbent assay). An analytical system may use, for example, LOCI (luminescent oxygen channeling), FOCI (fluorescent oxygen channeling), or ALPHAscreen. An analytical technique may involve incubating and/or diluting a sample before or during the analysis/assaying of the sample.

In some embodiments, the compositions, methods and devices described herein make use of fluorescent oxygen channeling immunoassay (FOCI) compositions and methods. FOCI is generally described in U.S. Pat. Nos. 5,807,675; 5,616,719; and 7,635,571, the entire contents of which are expressly incorporated herein by reference. In some embodiments, a first analyte-binding agent that is capable of binding to an analyte and comprises a photosensitizer is used in combination with a second analyte-binding agent comprising a fluorogenic dye. In some embodiments, the photosensitizer of the first analyte-binding agent generates singlet oxygen in an excited state thereby causing the fluorogenic dye of the second analyte-binding agent to emit fluorescence upon reacting with the singlet oxygen. In some embodiments, the emitted fluorescence can be detected to, e.g., determine the presence and/or absence of the analyte and/or to quantitate and/or analyze the analyte in a sample. In some embodiments, the first and the second analyte-binding agents bind to the same region (e.g., epitope) of the analyte (e.g., a protein). For example, in some embodiments, the first and the second analyte-binding agents comprise the same type of analyte-binding moiety or reagent (e.g., the same antibody). In some embodiments, the first and the second analyte-binding agents bind to separate regions (e.g., epitopes) of the analyte (e.g., a protein). In some embodiments, the first and the second analyte-binding agents bind to the separate regions of the analyte (e.g., a protein) that do not spatially overlap. In some embodiments, the first analyte-binding agent and the second analyte-binding agent are configured such that when both analyte-binding agents are bound to the analyte, the singlet oxygen generated by photosensitizer of the first analyte-binding agent is in close proximity to the fluorogenic dye of the second analyte-binding agent. In some embodiments, the first and/or second analyte binding agent(s) is an antigen-binding agent (e.g., an antibody). In some embodiments, the first and/or second analyte binding agent(s) is an affimer. In some embodiments, the first and/or second analyte binding agent(s) is an antigen-binding agent is an aptamer. In some embodiments, both the photosensitizer and fluorogenic dye are provided in the form of beads.

In some cases, arrays can use different probes (e.g., antibodies, scFvs, Fab fragments) attached to different particles or beads. In such arrays, the identity of which probe is attached to which particle or beads may be determinable from an encoding system. The probes can be antibodies or antigen-binding fragments or derivatives thereof.

The data pertaining to the sample can be compared to data pertaining to one or more control samples. In some cases, control samples can be samples from the same patient at different times. In some cases, the one or more control samples can comprise one or more samples from healthy subjects, unhealthy subjects, or a combination thereof. The one or more control samples can comprise one or more samples from healthy subjects, subjects suffering from pregnancy-associated conditions other than preeclampsia, subjects suffering chronic conditions along with pregnancy associated conditions, or subjects suffering from chronic conditions alone.

In some instances, the expression level data for various samples is used to develop or train an algorithm or classifier provided herein. In some instances, where the subject is a patient, such as a pregnant female; gene expression levels are measured in a sample from the patient and a classifier or algorithm (e.g., trained algorithm) is applied to the resulting data in order to detect, predict, monitor, rule out, or estimate the risk of a pregnancy-associated condition such as preeclampsia.

In some cases, analysis of expression levels initially provides a measurement of the expression level of each of several individual biomarkers. The expression level can be absolute in terms of a concentration of a biomarker, or relative in terms of a relative concentration of an expression product of interest to another biomarker in the sample. For example, relative expression levels of proteins can be expressed with respect to the expression level of a housekeeping or structural protein in the sample. Relative expression levels can also be determined by simultaneously analyzing differentially labeled samples bound to the same array. Expression levels can also be expressed in arbitrary units, for example, related to signal intensity.

Classifiers and Classifier Probe Sets

Disclosed herein is the use of a classification system comprising one or more classifiers. In some instances, the classifier is a 2-way classifier. In some instances, a two-way classifier can classify a sample from a pregnant patient into one of two classes comprising preeclampsia (PreE) and non-preeclampsia (nonPreE). In some instances, the classifier may be used classify a subject as not needing treatment for preeclampsia. In some instances, a multi-way classifier may be used (e.g., preeclampsia, non-preeclampsia, and indeterminate).

Classifiers and/or classifier probe sets (e.g., antibody sets) can be used to either rule-in or rule-out a sample as from a patient to be treated for preeclampsia. For example, a classifier can be used to classify a sample as being from a healthy subject. Alternatively, a classifier can be used to classify a sample as being from an unhealthy subject. Alternatively, or additionally, classifiers can be used to either rule-in or rule-out a sample as being from a subject who should be treated for preeclampsia.

Many statistical classification techniques are suitable to classify samples as described above. In supervised learning approaches, a group of samples from two or more groups (e.g. PE and non-PE) are analyzed with a statistical classification method. Biomarker presence/level data can be used as a classifier that differentiates between the two or more groups. A new sample can then be analyzed so that the classifier can associate the new sample with one of the two or more groups. Commonly used supervised classifiers include without limitation the neural network (multi-layer perceptron), support vector machines, k-nearest neighbors, Gaussian mixture model, Gaussian, naive Bayes, decision tree and radial basis function (RBF) classifiers. Linear classification methods include Fisher's linear discriminant, logistic regression, naive Bayes classifier, perceptron, and support vector machines (SVMs). Other classifiers for use with the invention include quadratic classifiers, k-nearest neighbor, boosting, decision trees, random forests, neural networks, pattern recognition, Bayesian networks and Hidden Markov models. One of skill will appreciate that these or other classifiers, including improvements of any of these, are contemplated within the scope of the invention.

Classification using supervised methods is generally performed by the following methodology:

In order to solve a given problem of supervised learning (e.g. learning to recognize handwriting) one has to consider various steps:

1. Gather a training set. These can include, for example, serum samples from pregnant female patients (e.g. PE and non-PE). The training samples are used to "train" the classifier.

2. Determine the input "feature" representation of the learned function. The accuracy of the learned function depends on how the input object is represented. Typically, the input object is transformed into a feature vector, which contains a number of features that are descriptive of the object. The number of features should not be too large, because of the curse of dimensionality; but should be large enough to accurately predict the output. The features might include a set of biomarkers as described herein.

3. Determine the structure of the learned function and corresponding learning algorithm. A learning algorithm (e.g. "trained algorithm") is chosen, e.g., artificial neural networks, decision trees, Bayes classifiers or support vector machines. The learning algorithm is used to build the classifier.

4. Build the classifier (e.g. classification model). The learning algorithm is run on the gathered training set. Parameters of the learning algorithm may be adjusted by optimizing performance on a subset (called a validation set) of the training set, or via cross-validation. After parameter adjustment and learning, the performance of the algorithm may be measured on a test set of naive samples that is separate from the training set.

Once the classifier (e.g. classification model) is determined as described above, it can be used to classify a sample, e.g., a serum sample from a pregnant patient that is being analyzed by the methods described herein.

Unsupervised learning approaches can also be used with the invention. Clustering is an unsupervised learning approach wherein a clustering algorithm correlates a series of samples without the use the labels. The most similar samples are sorted into "clusters." A new sample could be sorted into a cluster and thereby classified with other members that it most closely associates.

Data Analysis Systems and Methods

The methods, kits, and systems disclosed herein can comprise algorithms or uses thereof. The one or more algorithms can be used to classify one or more samples from one or more subjects. The one or more algorithms can be applied to data from one or more samples. The data can comprise biomarker expression data.

The methods disclosed herein can comprise assigning a classification to one or more samples from one or more subjects. Assigning the classification to the sample can comprise applying an algorithm to the expression level. In some cases, the gene expression levels are inputted to a data analysis system comprising a trained algorithm for classifying the sample as one of the conditions comprising preeclampsia, eclampsia, non-preeclampsia, chronic hypertension, gestational hypertension, or HELLP (Hemolysis, Elevated Liver enzymes, and Low Platelet count—see e.g., Weinstein et al. Am J Obstet Gynecol. 142(1982):159-67) syndrome. In some embodiments the algorithm can, as part of its execution, calculate an index for a sample and compare the sample index to a threshold value; the predefined relationship can be indicative of a likelihood of the sample belonging to a particular classification.

The algorithm can provide a record of its output including a classification of a sample and/or a confidence level. In some instances, the output of the algorithm can be the possibility of the subject of having a condition comprising preeclampsia, eclampsia, chronic hypertension, gestational hypertension, or HELLP syndrome.

A data analysis system can be a trained algorithm. The algorithm can comprise a linear classifier. In some instances, the linear classifier comprises one or more of linear discriminant analysis, Fisher's linear discriminant, Naïve Bayes classifier, Logistic regression, Perceptron, Support vector machine, or a combination thereof. The linear classifier can be a support vector machine (SVM) algorithm. The algorithm can comprise a two-way classifier. The two-way classifier can comprise one or more decision tree, random forest, Bayesian network, support vector machine, neural network, or logistic regression algorithms.

The algorithm can comprise one or more linear discriminant analysis (LDA), Basic perceptron, Elastic Net, logistic regression, (Kernel) Support Vector Machines (SVM), Diagonal Linear Discriminant Analysis (DLDA), Golub Classifier, Parzen-based, (kernel) Fisher Discriminant Classifier, k-nearest neighbor, Iterative RELIEF, Classification Tree, Maximum Likelihood Classifier, Random Forest, Nearest Centroid, Prediction Analysis of Microarrays (PAM), k-medians clustering, Fuzzy C-Means Clustering, Gaussian mixture models, graded response (GR), Gradient Boosting Method (GBM), Elastic-net logistic regression, logistic regression, or a combination thereof. The algorithm can comprise a Diagonal Linear Discriminant Analysis (DLDA) algorithm. The algorithm can comprise a Nearest Centroid algorithm. The algorithm can comprise a Random Forest algorithm. In some embodiments, for discrimination of preeclampsia and non-preeclampsia, the performance of logistic regression, random forest, and gradient boosting method (GBM) is superior to that of linear discriminant analysis (LDA), neural network, and support vector machine (SVM).

Biomarkers/Gene Expression Products

The term "biomarker" refers to a measurable indicator of some biological state or condition. In some instances, a biomarker can be a substance found in a subject, a quantity of the substance, or some other indicator. For example, a biomarker can be the amount of a protein and/or other gene expression products in a sample. In some embodiments, a biomarker is a full-length, unmodified protein. In other embodiments, a biomarker is an alternatively spliced, post-translationally cleaved, or post-translationally chemically modified (e.g., methylated, phosphorylated, glycosylated, formylated, etc) protein. In some embodiments, a biomarker is a complex of a protein with another protein at a particular stoichiometry. In some embodiments, a biomarker is a free protein in the absence of other associated binding partners.

The methods, compositions and systems as described here also relate to the use of biomarker panels and/or gene expression products for purposes of identification, diagnosis, classification, treatment or to otherwise characterize various conditions of pregnant patients comprising Non-PreE, PreE, chronic hypertension, gestational hypertension, or HELLP syndrome. Sets of biomarkers and/or gene expression products are provided, as well as methods of obtaining such sets of biomarkers. Often, the pattern of levels of gene expression biomarkers in a panel (also known as a signature) is determined from one or more references samples and then used to evaluate the signature of the same panel of biomarkers in a test sample, such as by a measure of similarity between the test sample signature and the reference sample signature.

The methods provided herein can comprise identifying or ruling out a condition from a combination of a species of PlGF with secondary biomarkers. The methods provided herein can comprise identifying or ruling out a condition (e.g. preeclampsia) from (e.g., based on analysis from) one or more biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) one or more biomarkers selected from sFLT, free sFLT, Endoglin, KIM-1, FGF21, Decorin, and CD274 in combination with PlGF(f), PlGF(d), or PlGF (% free).

Without wishing to be limited by theory, preeclampsia is thought to originate in abnormal trophoblast invasion, which results in incomplete spiral artery remodeling and hypoperfusion of the placenta, and that this hypoperfusion of the placenta triggers dysfunction in multiple body systems causing the signs and symptoms of preeclampsia. Such dysfunctional systems can include, as a result of placental hypoperfusion, angiogenesis and endothelial function, as evidenced e.g. by imbalances in pro-and-anti-angiogenic factors, many of which are released by the placenta in response to the abnormal physiology of preeclampsia, and which disrupt vascular homeostasis in the mother's body. SFLT1 (Soluble FMS-like tyrosine kinase 1, a tyrosine-protein kinase that acts as a cell-surface receptor for VEGFA, VEGFB and PlGF and decreases towards term, and plays an essential role in the development of embryonic vasculature), PlGF (Placental growth factor, a proangiogenic protein peaking at 30 weeks of gestation that stimulates endothelial cell growth, proliferation, and migration), DCN (Decorin, which is a functional component of the extracellular matrix and plays a role in tissue repair and regulation of cell adhesion and migration by binding to ECM molecules), ENG (Endoglin, which in its soluble form, sENG (Endoglin) is a powerful antiangiogenic molecule, and acts by inhibiting TGF-â1 binding), and FGF21 (Fibroblast growth factor 21, which has been demonstrated to be expressed in placental syncytiotrophoblasts, and is both an adipokine and a regulator of glucose transport) are considered to be markers of angiogenesis dysfunction in preeclampsia. Another such dysfunctional system is oxygen signaling, which results from hypoperfusion of the placenta, and leads to upregulation of oxidative stress factors. KIM-1 (Kidney Injury Molecule-1) is considered to be a marker of dysfunction in oxygen signaling in preeclampsia, as its expression is known to increase in response to local hypoxia/ischemia in proximal renal tubule cells.

The methods provided herein can comprise identifying or ruling out a condition (e.g. preeclampsia) from (e.g., based on analysis from) biomarkers comprising: (a) sFLT1 or Endoglin; and (b) PlGF (free, dissociated, or % free). The methods provided herein can comprise identifying or ruling out a condition (e.g. preeclampsia) from (e.g., based on analysis from) biomarkers comprising: (a) sFLT1 or Endoglin; (b) PlGF (free, dissociated, or % free); and (c) KIM1. The methods provided herein can comprise identifying or ruling out a condition (e.g. preeclampsia) from (e.g., based on analysis from) biomarkers comprising: (a) sFLT1 or Endoglin; (b) PlGF (free, dissociated, or % free); (c) KIM1; and (d) FGF21. The methods provided herein can comprise identifying or ruling out a condition (e.g. preeclampsia)

from (e.g., based on analysis from) biomarkers comprising: (a) sFLT1 or Endoglin; (b) PlGF (free, dissociated, or % free); (c) KIM1; and (d) Decorin. The methods provided herein can comprise identifying or ruling out a condition (e.g. preeclampsia) from (e.g., based on analysis from) biomarkers comprising: (a) sFLT1 or Endoglin; (b) PlGF (free, dissociated, or % free); (c) KIM1; (d) FGF21; and (e) Decorin.

Additionally, because sFLT1 and Endoglin are highly correlated but each of them also provide additional (exclusive) information that results in improved performance, the biomarkers may comprise both sFLT1 and Endoglin. The methods provided herein can comprise identifying or ruling out a condition (e.g. preeclampsia) from (e.g., based on analysis from) biomarkers comprising: (a) sFLT1; (b) Endoglin; and (c) PlGF (free, dissociated, or % free). The methods provided herein can comprise identifying or ruling out a condition (e.g. preeclampsia) from (e.g., based on analysis from) biomarkers comprising: (a) sFLT1; (b) Endoglin; (c) PlGF (free, dissociated, or % free); and (d) KIM1. The methods provided herein can comprise identifying or ruling out a condition (e.g. preeclampsia) from (e.g., based on analysis from) biomarkers comprising: (a) sFLT1; (b) Endoglin; (c) PlGF (free, dissociated, or % free); (d) KIM1; and (e) FGF21. The methods provided herein can comprise identifying or ruling out a condition (e.g. preeclampsia) from (e.g., based on analysis from) biomarkers comprising: (a) sFLT1; (b) Endoglin; (c) PlGF (free, dissociated, or % free); (d) KIM1; and (e) Decorin. The methods provided herein can comprise identifying or ruling out a condition (e.g. preeclampsia) from (e.g., based on analysis from) biomarkers comprising: (a) sFLT1; (b) Endoglin; (c) PlGF (free, dissociated, or % free); (d) KIM1; (e) FGF21; and (f) Decorin.

The methods provided herein can comprise identifying or ruling out a condition (e.g. preeclampsia) from (e.g., based on analysis from) two or more biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) three or more biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) four or more biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) five or more biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) six or more biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) seven or more biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) all of sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) two biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) three biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) four biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) five biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) six biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) seven biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) no more than two biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) no more than three biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) no more than four biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) no more than five biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) no more than six biomarkers selected from sFLT, free sFLT, Endoglin, KIM-1, FGF21, Decorin, Clec4A and CD274 in combination with PlGF(f), PlGF(d), or PlGF (% free). The methods provided herein can comprise identifying or ruling out a condition (e.g. preeclampsia) from (e.g., based on analysis from) no more than seven biomarkers selected from sFLT, free sFLT, Endoglin, KIM-1, FGF21, Decorin, Clec4A and CD274 in combination with PlGF(f), PlGF(d), or PlGF (% free).

Clinical/Therapeutic Applications

The methods, compositions, systems and kits provided herein can be used to detect, diagnose, predict or monitor a condition of a pregnant patient. In some instances, the methods, compositions, systems and kits described herein provide information to a medical practitioner that can be useful in making a clinical therapeutic decision. Clinical and therapeutic decisions can include decisions to: continue with a particular therapy, modify a particular therapy, alter the dosage of a particular therapy, stop or terminate a particular therapy, altering the frequency of a therapy, introduce a new therapy, introduce a new therapy to be used in combination with a current therapy, or any combination of the above. In some instances, medical action taken may comprise watchful waiting or the administration of one or more additional diagnostic tests of the same or different nature. In some cases, a clinical decision may be made to not induce labor, or to proceed with ambulant monitoring of the subject. In some cases, the methods provided herein can be applied in an experimental setting, e.g., clinical trial. In some instances, the methods provided herein can be used to monitor a pregnant patient who is being treated with an experimental agent such as an angiogenic/antiangiogenic drug, compound, or therapeutic cell type. In some instances, the methods provided herein can be useful to determine whether a subject can be administered an experimental agent (e.g., an agonist, antagonist, peptidomimetic, protein, peptide, nucleic acid, therapeutic cell, small molecule, or other drug candidate) to reduce the risk of preeclampsia. Thus, the methods described herein can be useful in determining if a subject can be effectively treated with an experimental agent and for monitoring the subject for risk of preeclampsia.

Detecting/Diagnosing a Condition of a Pregnant Patient

The methods, compositions, systems and kits provided herein are particularly useful for detecting, diagnosing, or ruling out a condition of a pregnant patient such as a condition the pregnant patient has at the time of testing. An exemplary condition that can be detected, diagnosed, or ruled out with the present method includes preeclampsia. The methods, compositions, systems, and kits provided herein can also be useful, in combination with other standard clinical data collected for pregnant patients, for ruling in or ruling out a diagnosis of preeclampsia, hypertension, gestational hypertension, or HELLP syndrome. The methods provided herein are particularly useful for pregnant patients who have exhibited one or more new-onset symptoms associated with preeclampsia prior to testing (e.g., hypertension, proteinuria, low platelet count, elevated serum creatinine levels, elevated liver enzymes, pulmonary edema, or cerebral/visual symptoms), such that the patients are suspected of having preeclampsia.

In some embodiments, the methods, compositions, systems and kits provided herein can rule out a diagnosis of preeclampsia for a specified number of days in the future. In some instances, the specified number of days in the future is 1 to 30 days. In some instances, the specified number of days in the future is at least 1 day. In some instances, the specified number of days in the future is at most 30 days. In some instances, the specified number of days in the future is 1 day to 5 days, 1 day to 10 days, 1 day to 30 days, 5 days to 10 days, 5 days to 30 days, or 10 days to 30 days. In some instances, the specified number of days in the future is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In some preferred embodiments, the specified number of days in the future is 5 days to 10 days. In other preferred embodiments, the specified number of days in the future is 5, 6, 7, 8, 9, or 10 days. In some embodiments, the methods, compositions, systems and kits provided herein can rule-out mothers for hospital admission and preterm delivery. In some embodiments, the methods, compositions, systems and kits provided herein can rule out a diagnosis of preeclampsia for a specified number of weeks in the future. In some instances, the specified number of weeks is at least 1 week. In some instances, the specified number of weeks is at least 2 weeks. In some instances, the specified number of weeks is at least 3 weeks. In some instances, the specified number of weeks is at least 4 weeks. In some instances, the specified number of weeks is at least 5 weeks. In some instances, the specified number of weeks is at least 6 weeks. In some instances, the specified number of weeks is at most 1 week. In some instances, the specified number of weeks is at most 2 weeks. In some instances, the specified number of weeks is at most 3 weeks. In some instances, the specified number of weeks is at most 4 weeks. In some instances, the specified number of weeks is at most 5 weeks. In some instances, the specified number of weeks is at most 6 weeks.

In some embodiments, the methods, compositions, systems and kits provided herein can rule out a diagnosis of preeclampsia for a specified number of weeks in the future with a particular PPV. In some cases, the positive predictive value (PPV) is at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, or 57%, or any range in between these values.

In some embodiments, the methods, compositions, systems and kits provided herein can rule out a diagnosis of preeclampsia for a specified number of weeks in the future with a particular NPV. The NPV can be at least about 80%, 81%, 82%, 83%, 84%, 85%, 86%, 87%, 88%, 89%, 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values.

In some embodiments, the methods, compositions, systems and kits provided herein can rule out a diagnosis of preeclampsia for a specified number of weeks in the future with a particular AUC. In some cases, the AUC of can be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

In some embodiments, the methods, compositions, systems and kits provided herein can rule out a diagnosis of preeclampsia for a specified number of weeks in the future with a particular AUP. The AUP can be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

The diagnosis, detection, or ruling out of a condition of the pregnant patient can be particularly useful in limiting the number of unnecessary invasive medical interventions that are administered to the patient, and/or indicating alternative less-invasive therapeutic interventions such as pharmacological therapies (anticonvulsants, antihypertensives, central alpha agonists, alpha-blockers, beta-blockers, calcium-channel blockers, vasodilators, cyclooxygenase inhibitors, or, acetylsalicylic acid). For example, the methods provided herein can limit, delay, or eliminate the use of preterm cesarean delivery or labor induction in patients suspected of having preeclampsia via high-confidence ruling out of a diagnosis of preeclampsia in the pregnant patient (e.g., via a high negative predictive value of the methods, compositions, systems, and kits provided herein).

In some cases, the methods provided herein can inform the clinical decision to proceed to delivery (e.g. when the pregnant patient is identified as being at-risk of preeclampsia). Such a decision may involve the administration of a labor-inducing or cervical ripening agent (e.g. prostaglandin, oxytocin, misoprostol, mifepristone, or relaxin), a corticosteroid (to aid in lung development prior to delivery), and/or performing a C-section.

In a further embodiment, the methods, compositions, systems and kits provided herein can be used alone or in combination with other standard diagnosis methods currently used to detect, diagnose, or rule out a condition of a pregnant patient, such as but not limited to blood pressure measurement, urine protein measurement, blood platelet counting, serum creatinine level measurement, creatinine clearance measurement, urine protein/creatinine ratio measurement, serum transaminase level measurement, serum LDH level measurement, serum bilirubin level measurement, or Doppler ultrasound indices (e.g., uterine artery indices). For example, hypertension in a pregnant patient can be indicative of conditions such as chronic hypertension, gestational hypertension, or preeclampsia; ruling out the diagnosis of preeclampsia via the methods, compositions, systems and kits provided herein allows for the patient to be correctly diagnosed with chronic hypertension or gestational hypertension.

Predicting a Condition of a Pregnant Patient

In some embodiments, the methods provided herein can predict preeclampsia prior to actual onset of the condition or symptoms associated with the condition (e.g., hypertension or proteinuria). In some instances, the methods provided herein can predict preeclampsia or other disorders in a pregnant patient at least 1 day, 1 week, 2 weeks, 3 weeks, 1 month, 2 months prior to onset of the condition or symptoms associated with the condition. In other instances, the methods provided herein can predict preeclampsia or other disorders in a pregnant patient at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days prior to onset. In other instances, the methods provided herein can predict preeclampsia or other disorders in a pregnant patient at least 1, 2, 3, or 4 months prior to onset.

Monitoring a Condition of a Pregnant Patient

Provided herein are methods, systems, kits and compositions for monitoring a condition of a pregnant patient. Often, the monitoring is conducted by serial testing, such as serial non-invasive tests, serial minimally-invasive tests (e.g., blood draws), or some combination thereof. Preferably, the monitoring is conducted by administering serial non-invasive tests or serial minimally-invasive tests (e.g., blood draws).

In some instances, the pregnant patient is monitored as needed (e.g., on an as-needed basis) using the methods described herein. Additionally, or alternatively the pregnant patient can be monitored weekly, monthly, or at any pre-specified intervals. In some instances, the pregnant patient is monitored at least once every 24 hours. In some instances, the pregnant patient is monitored at least once every 1 day to 30 days. In some instances, the pregnant patient is monitored at least once every at least 1 day. In some instances, the pregnant patient is monitored at least once every at most 30 days. In some instances the pregnant patient is monitored at least (optionally on average) once every 1 day to 5 days, 1 day to 10 days, 1 day to 15 days, 1 day to 20 days, 1 day to 25 days, 1 day to 30 days, 5 days to 10 days, 5 days to 15 days, 5 days to 20 days, 5 days to 25 days, 5 days to 30 days, 10 days to 15 days, 10 days to 20 days, 10 days to 25 days, 10 days to 30 days, 15 days to 20 days, 15 days to 25 days, 15 days to 30 days, 20 days to 25 days, 20 days to 30 days, or 25 days to 30 days. In some instances, the pregnant patient is monitored at least once every 1, 2, 3, 4, 5, 6, 7, 8, 9, 10, 11, 12, 13, 14, 15, 16, 17, 18, 19, 20, 21, 28, 29, 30 or 31 days. In some instances, the pregnant patient is monitored at least once every 1, 2, or 3 months. In some instances, the pregnant patient is monitored via the methods described herein no more frequently than one week, 10 days, two weeks, three weeks, or one month. In other words, the predictive value of the some of the methods described herein can be of clinical use for at least one week, at least 10 days, at least two weeks, at least three weeks, or at least one month.

In some instances, biomarker expression levels in the patients can be measured, for example, within, one week, two weeks, three weeks, or four weeks after detection of one or more symptoms associated with preeclampsia (e.g., hypertension or proteinuria). In some methods, biomarker expression levels are determined at regular intervals, e.g., every 1 week, 2 weeks, 3 weeks, 1 month, 2 months or 3 months post-conception, after the beginning of the $2^{nd}$ trimester, after the beginning of the $3^{rd}$ trimester, or after week 20 of the pregnancy, either indefinitely, or until evidence of a condition is observed. In some methods, biomarker expression levels are determined at regular intervals after week 20, 21, 22, 23, 24, 25, 26, 27, 28, 29, 30, 31, 32, 33, 34, 35, 36, 37, 38, 39, 40, 41, or 42 weeks. Where evidence of a condition is observed, the frequency of monitoring is sometimes increased. In some methods, baseline values of expression levels are determined in a subject before detection of one or more symptoms associated with preeclampsia (e.g., hypertension or proteinuria) in combination with determining expression levels after onset of symptoms.

Therapeutic Decisions/Regimens

The results of diagnosing, predicting, ruling out, or monitoring a condition of the pregnant patient can be useful for informing a clinical or therapeutic decision such as determining or monitoring a therapeutic regimen.

In some embodiments, an entity that acquires sample data and/or classifies a sample from a patient as having preeclampsia is other than the physician, caregiver, or medical institution performing the treatment. In some embodiments, the entity acquiring sample data (e.g. levels of levels of one or more biomarkers described herein), calculating an index based (at least in part) on the levels of the plurality of the protein biomarkers, and/or determining risk of preeclampsia is a third-party testing service. Thus, in some embodiments, determining or monitoring a therapeutic regimen first comprises receiving information from a third-party testing service, which can comprise, for example (but not limited to), classification of a sample as being at risk or not of preeclampsia, risk of a pregnant patient having preeclampsia, levels of a plurality of protein biomarkers from the sample associated with preeclampsia (e e.g. levels of levels of one or more biomarkers described herein), or the likelihood a pregnant patient will deliver preterm.

In some embodiments, an entity that acquires sample data, determines the risk of preterm birth of the patient from the sample, and/or classifies a sample from a patient as having a significant risk of preterm birth is the same entity that performing the treatment.

In some instances, determining a therapeutic regimen can comprise administering a therapeutic drug. In some instances, determining a therapeutic regimen comprises modifying, continuing, initiating or stopping a therapeutic regimen. In some instances, determining a therapeutic regimen comprises treating the disease or condition (e.g., preeclampsia, eclampsia, gestational hypertension, hypertension, or HELLP syndrome). In some instances, the therapy is an anti-hypertensive therapy. In some instances, the therapy is an anti-cyclooxygenase (COX) therapy. In some instances, the therapy is an anti-convulsant therapy.

Modifying the therapeutic regimen can comprise terminating a therapy. Modifying the therapeutic regimen can comprise altering a dosage of a therapy. Modifying the therapeutic regimen can comprise altering a frequency of a therapy. Modifying the therapeutic regimen can comprise administering a different therapy. In some instances, the results of diagnosing, predicting, or monitoring a condition of the pregnant patient can be useful for informing a therapeutic decision such as caesarean delivery. Other examples of therapeutic decisions can be cervical ripening and/or labor induction. Examples of agents that can be used for cervical ripening and/or labor induction include prostaglandins, misoprostol, mifepristone, relaxin, and oxytocin. Other examples of therapeutic decisions can be cesarean delivery.

Examples of a therapeutic regimen can include administering compounds or agents having anti-hypertensive properties (e.g., central alpha agonists such as methyldopa, vasodilators such as clonidine, diazoxide, hydralazine and prazosin, calcium-channel blockers such as nifedipine and verapamil, alpha-blockers such as labetalol, or beta-blockers such as oxprenolol), compounds or agents having anti-cyclooxygenase activity (e.g., acetylsalicylic acid), or compounds having anti-convulsant activity (e.g., phenytoin or magnesium sulfate). These compounds can be used alone or in combination.

In some cases, modifying the therapeutic regimen can comprise proceeding with treatment of said pregnant human in a manner that avoids unnecessary treatment of preeclampsia. For instance, in some embodiments, managing the pregnant human subject identified not as at risk for preeclampsia comprises ambulant monitoring, or refraining from the administration of any drug for treating preeclampsia. In some instances, in patients that are identified as patients that should not be treated for preeclampsia, antihypertensive drugs (rather than delivery) may be prescribed and/or administered to the patient. In some instances, in patients that are identified as not patients that should not be treated for preeclampsia, the preeclampsia test is repeated at an increased frequency. The test can be re-performed, and sample re-drawn from the patient weekly, monthly, or at any pre-specified intervals. In some instances, the pregnant patient is monitored at least once every 24 hours. In some instances, the pregnant patient is monitored at least once every 1 day to 30 days. In some instances, the pregnant patient is monitored at least once every at least 1 day. In some instances, the pregnant patient is monitored at least once every at most 30 days. In some instances the pregnant patient is monitored at least (optionally on average) once every 1 day to 5 days, 1 day to 10 days, 1 day to 15 days, 1 day to 20 days, 1 day to 25 days, 1 day to 30 days, 5 days to 10 days, 5 days to 15 days, 5 days to 20 days, 5 days to 25 days, 5 days to 30 days, 10 days to 15 days, 10 days to 20 days, 10 days to 25 days, 10 days to 30 days, 15 days to 20 days, 15 days to 25 days, 15 days to 30 days, 20 days to 25 days, 20 days to 30 days, or 25 days to 30 days. In some instances, the pregnant patient is monitored at least once every 1, 2, 3, 4, 5, 6, 7, 8, 9, 10, 11, 12, 13, 14, 15, 16, 17, 18, 19, 20, 21, 28, 29, 30 or 31 days. In some instances, the pregnant patient is monitored at least once every 1, 2, or 3 months. In some instances, the pregnant patient is monitored via the methods described herein no more frequently than one week, 10 days, two weeks, three weeks, or one month. In other words, the predictive value of the some of the methods described herein can be of clinical use for at least one week, at least 10 days, at least two weeks, at least three weeks, or at least one month.

Sensitivity, Specificity, NPV, PPV, AUC, AUP, and Accuracy

The methods, kits, and systems disclosed herein for use in identifying, classifying (or ruling out a classification) or characterizing a sample can be characterized by having a specificity of at least about 80% using the methods disclosed herein. In some embodiments, the specificity of the methods is at least about 85%. In some embodiments, the specificity of the methods is at least about 90%. In some embodiments, the specificity of the methods is at least about 95%. The specificity of the method can be at least about 80%, 81%, 82%, 83%, 84%, 85%, 86%, 87%, 88%, 89%, 90%, 91%, 92%, 93%, 94%, 95%, 96%, 97%, 98%, or 99%, or any range in between these values.

In some embodiments, the present invention provides a method of identifying, classifying (or ruling out a classification) or characterizing a sample that gives a sensitivity of at least about 80% using the methods disclosed herein. In some embodiments, the sensitivity of the methods is at least 85%. In some embodiments, the sensitivity of the methods is at least 90%. In some embodiments, the sensitivity of the methods is at least 95%. The sensitivity of the method can be at least about 80%, 81%, 82%, 83%, 84%, 85%, 86%, 87%, 88%, 89%, 90%, 91%, 92%, 93%, 94%, 95%, 96%, 97%, 98%, or 99%, or any range in between these values.

The methods, kits and systems disclosed herein can improve upon the accuracy of current methods of monitoring or predicting a status or outcome of a pregnancy (e.g. preeclampsia) or identifying or ruling out a classification of a sample. The accuracy of the methods, kits, and systems disclosed herein can be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

The methods, kits, and systems for use in identifying, classifying (or ruling out a classification) or characterizing a sample can be characterized by having a negative predictive value (NPV) greater than or equal to 90%. The NPV can be at least about 80%, 81%, 82%, 83%, 84%, 85%, 86%, 87%, 88%, 89%, 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values. The NPV can be greater than or equal to 95%. The NPV can be greater than or equal to 96%. The NPV can be greater than or equal to 97%. The NPV can be greater than or equal to 98%.

The methods, kits, and/or systems disclosed herein for use in identifying, classifying (or ruling out a classification) or characterizing a sample (e.g. for preeclampsia) can be characterized by having a positive predictive value (PPV) of at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, or 57%, or any range in between these values using the methods disclosed herein.

The methods, kits and systems disclosed herein can improve upon the AUC of current methods of monitoring or predicting a status or outcome of a pregnancy (e.g. preeclampsia) or identifying or ruling out a classification of a sample. The AUC of the methods, kits, and systems disclosed herein can be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

The methods, kits and systems disclosed herein can improve upon the AUP of current methods of monitoring or predicting a status or outcome of a pregnancy (e.g. preeclampsia) or identifying or ruling out a classification of a sample. The AUP of the methods, kits, and systems disclosed herein can be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

The methods, kits, and systems disclosed herein for use in diagnosing, prognosing, and/or monitoring a status or outcome of a pregnancy in a subject in need thereof can be characterized by having an accuracy of at least about 80%, 82%, 85%, 87%, 90%, 92%, 95%, or 97% or any range in between these values.

The methods, kits, and systems disclosed herein for use in diagnosing, prognosing, and/or monitoring a status or outcome of a pregnancy in a subject in need thereof can be characterized by having a specificity of at least about 80%, 82%, 85%, 87%, 90%, 92%, 95%, or 97%, or any range in between these values.

The methods, kits, and systems disclosed herein for use in diagnosing, prognosing, and/or monitoring a status or outcome of a pregnancy in a subject in need thereof can be characterized by having a sensitivity of at least about 80%, 82%, 85%, 87%, 90%, 92%, 95%, or 97%, or any range in between these values.

The methods, kits, and systems disclosed herein for use in diagnosing, prognosing, and/or monitoring a status or outcome of a pregnancy in a subject in need thereof can be characterized by having a negative predictive value (NPV) greater than or equal to 90%. The NPV can be at least about 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values. The NPV can be greater than or equal to 95%. The NPV can be greater than or equal to 96%. The NPV can be greater than or equal to 97%. The NPV can be greater than or equal to 98%.

The methods, kits, and systems disclosed herein for use in diagnosing, prognosing, and/or monitoring a status or outcome of a pregnancy in a subject in need thereof can be characterized by having a positive predictive value (PPV) of at least about 80%. In some embodiments, the methods, kits, and systems disclosed herein for use in diagnosing, prognosing, and/or monitoring a status or outcome of a pregnancy in a subject in need thereof can be characterized by having a positive predictive value (PPV) of at least about 85%. In some embodiments, the methods, kits, and systems disclosed herein for use in diagnosing, prognosing, and/or monitoring a status or outcome of a pregnancy in a subject in need thereof can be characterized by having a positive predictive value (PPV) of at least about 90%. The PPV can be at least about 80%, 85%, 90%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values. The PPV can be greater than or equal to 95%. The PPV can be greater than or equal to 98%.

In some embodiments, disclosure provides a test for confirming preeclampsia in a subject, preferably a pregnant subject, wherein the test is able to discern subjects not having preeclampsia but having one or more symptoms associated with preeclampsia from subjects having by preeclampsia with an NPV of at least about 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values. The one or more symptoms associated with preeclampsia can be diabetes (e.g. gestational, type I or type II), higher than normal glucose level, hypertension (e.g. chronic or non-chronic), excessive or sudden weight gain, higher than normal weight, obesity, higher than normal body mass index (BMI), abnormal weight gain, abnormal blood pressure, water retention, hereditary factors, abnormal proteinuria, headache, edema, abnormal protein/creatinine ratio, abnormal platelet count, stress, nulliparity, abnormal Papanicolaou test results (Pap smear), prior preeclampsia episodes (e.g., personal history of PreE), familial history of preeclampsia, preeclampsia in prior pregnancies, renal disease, thrombophilia, or any combination thereof. Gestational age may also be used in tests, such as tests for ruling out preeclampsia.

Computer Program

The methods, kits, and systems disclosed herein can include at least one computer program or use of the same. A computer program can include a sequence of instructions, executable in the digital processing device's CPU (i.e. processor), written to perform a specified task. Computer readable instructions can be implemented as program modules, such as functions, objects, Application Programming Interfaces (APIs), data structures, and the like, that perform particular tasks or implement particular abstract data types. In light of the disclosure provided herein, those of skill in the art will recognize that a computer program can be written in various versions of various languages.

The functionality of the computer readable instructions can be combined or distributed as desired in various environments. The computer program will normally provide a sequence of instructions from one location or a plurality of locations.

Further disclosed herein are systems for classifying (or ruling out a classification) one or more samples and uses thereof. The system can comprise (a) a digital processing device comprising an operating system configured to perform executable instructions and a memory device; (b) a computer program including instructions executable by the digital processing device to classify a sample from a subject comprising: (i) a first software module configured to receive a biomarker expression profile of one or more biomarkers from the sample from the subject; (ii) a second software module configured to analyze the biomarker expression profile from the subject; and (iii) a third software module configured to classify the sample from the subject based on a classification system. In some embodiments, the classification system comprises two classes. In other embodiments, the classification system comprises two or more classes. At least two of the classes can be selected from preeclampsia, non-preeclampsia (e.g., for at least a period of time), normal pregnancy, complicated pregnancy, and gestational hypertension. Analyzing the biomarker expression profile from the subject can comprise applying an algorithm. Analyzing the biomarker expression profile can comprise normalizing the biomarker expression profile from the subject.

Figure 11:
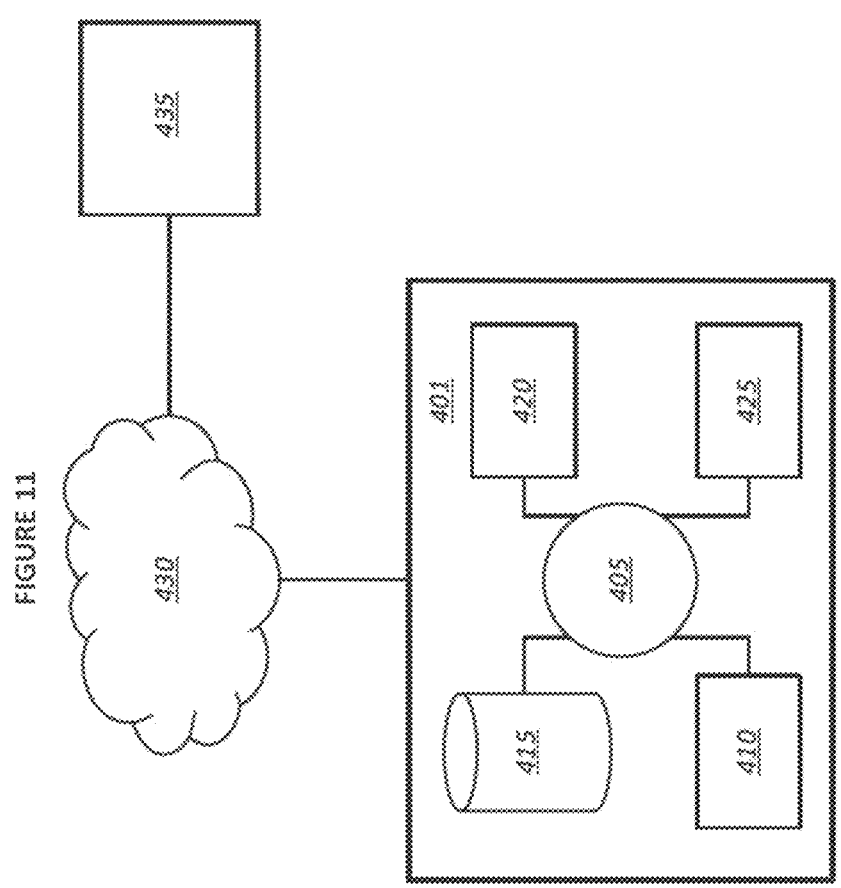
FIG. 11 shows an exemplary computer system that can be used alongside the methods, compositions, and systems described herein.

FIG. 11 shows a computer system (also "system" herein) 401 programmed or otherwise configured for implementing the methods of the disclosure, such as producing a selector set and/or for data analysis. The system 401 includes a central processing unit (CPU, also "processor" and "computer processor" herein) 405, which can be a single core or multi core processor, or a plurality of processors for parallel processing. The system 401 also includes memory 410 (e.g., random-access memory, read-only memory, flash memory), electronic storage unit 415 (e.g., hard disk), communications interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communications bus (solid lines), such as a motherboard. The storage unit 415 can be a data storage unit (or data repository) for storing data. The system 401 is operatively coupled to a computer network ("network") 430 with the aid of the communications interface 420. The network 430 can be the Internet, an internet and/or extranet, or an intranet and/or extranet that is in communication with the Internet. The network 430 in some instances is a telecommunication and/or data network. The network 430 can include one or more computer servers, which can enable distributed computing, such as cloud computing. The network 430 in some instances, with the aid of the system 401, can implement a peer-to-peer network, which can enable devices coupled to the system 401 to behave as a client or a server.

The system 401 is in communication with a processing system 435. The processing system 435 can be configured to implement the methods disclosed herein. In some examples, the processing system 435 is a microfluidic qPCR system. In other examples, the processing system 435 is an ALPHA screen or other plate reader. In other examples, the processing system 435 is a FACS sorter or analyzer. The processing system 435 can be in communication with the system 401 through the network 430, or by direct (e.g., wired, wireless) connection. In some embodiments, raw data from the processing system (e.g. a biomarker expression profile) is uploaded through the network to the system for processing (e.g. sample classification or determination of a probability of a certain classification). This data transfer may be direct (e.g. FTP, TCP, or other direct network connection between the processing system 435 and the system 401), or indirect (e.g. transfer to a cloud storage system which can be accessed by the system 401).

Methods as described herein can be implemented by way of machine (or computer processor) executable code (or software) stored on an electronic storage location of the system 401, such as, for example, on the memory 410 or electronic storage unit 415. During use, the code can be executed by the processor 405. In some examples, the code can be retrieved from the storage unit 415 and stored on the memory 410 for ready access by the processor 405. In some situations, the electronic storage unit 415 can be precluded, and machine-executable instructions are stored on memory 410.

Digital Processing Device

The methods, kits, and systems disclosed herein can include a digital processing device or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

The digital processing device will normally include an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

The device generally includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random-access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing-based storage. In further embodiments, the storage and/or memory device is a combination of devices such as those disclosed herein.

A display to send visual information to a user will normally be initialized. Examples of displays include a cathode ray tube (CRT, a liquid crystal display (LCD), a thin film transistor liquid crystal display (TFT-LCD, an organic light emitting diode (OLED) display. In various further embodiments, on OLED display is a passive-matrix OLED (PMOLED) or active-matrix OLED (AMOLED) display. In some embodiments, the display can be a plasma display, a video projector or a combination of devices such as those disclosed herein.

The digital processing device would normally include an input device to receive information from a user. The input device can be, for example, a keyboard, a pointing device including, by way of non-limiting examples, a mouse, trackball, track pad, joystick, game controller, or stylus; a touch screen, or a multi-touch screen, a microphone to capture voice or other sound input, a video camera to capture motion or visual input or a combination of devices such as those disclosed herein.

Non-Transitory Computer Readable Storage Medium

The methods, kits, and systems disclosed herein can include one or more non-transitory computer readable storage media encoded with a program including instructions executable by the operating system to perform and analyze the test described herein; preferably connected to a networked digital processing device. The computer readable storage medium is a tangible component of a digital device that is optionally removable from the digital processing device. The computer readable storage medium includes, by way of non-limiting examples, CD-ROMs, DVDs, flash memory devices, solid state memory, magnetic disk drives, magnetic tape drives, optical disk drives, cloud computing systems and services, and the like. In some instances, the program and instructions are permanently, substantially permanently, semi-permanently, or non-transitorily encoded on the media.

A non-transitory computer-readable storage media can be encoded with a computer program including instructions executable by a processor to create or use a classification system. The storage media can comprise (a) a database, in a computer memory, of one or more clinical features of two or more control samples, wherein (i) the two or more control samples can be from two or more subjects; and (ii) the two or more control samples can be differentially classified based on a classification system comprising two or more classes; (b) a first software module configured to compare the one or more clinical features of the two or more control samples; and (c) a second software module configured to produce a classifier set based on the comparison of the one or more clinical features. At least two of the classes can be selected from preeclampsia, non-preeclampsia, normal pregnancy, complicated pregnancy, and gestational hypertension.

Antigen/Biomarker Detection (E.g., Antibodies)

In some embodiments, at least one antigen binding reagent is used to detect any of the biomarkers identified herein. In some embodiments, the antigen binding reagent can be an antibody (monoclonal or polyclonal), antigen-binding fragment (e.g. Fab, Fab', F(ab)2, F(abc)2, or Fv fragment) of an antibody, or an antibody derivative (e.g. diabody, linear antibody, or scFv).

EXEMPLARY EMBODIMENTS

In some aspects, the present disclosure provides for a method of determining whether a pregnant human female is at risk of suffering from preeclampsia comprising: determining a free Placental Growth Factor to dissociated Placental Growth Factor (PlGF-f:PlGF-d) ratio of a biological sample collected from the pregnant human female. In some embodiments, the pregnant human female is identified as having a heightened risk of suffering from preeclampsia when a PlGF-f:PlGF-d ratio less than a first threshold value is determined. In some embodiments, the pregnant human female is identified as having a reduced risk of suffering from preeclampsia when a PlGF-f:PlGF-d ratio greater than a second threshold value is determined. In some embodiments, a PlGF-f:PlGF-d ratio less than a first threshold value indicates a heightened risk that the pregnant human female will suffer from preeclampsia. In some embodiments, a PlGF-f:PlGF-d ratio greater than a second threshold value indicates a reduced risk that the pregnant human female will suffer from preeclampsia.

The first and/or second threshold value can be determined by supervised learning using a trained algorithm. The trained algorithm can be trained using e.g. supervised learning approaches described herein.

In some embodiments, the method comprises collecting the biological sample. The biological sample may be collected by any of the methods described herein. The biological sample may be collected by venipuncture, fingerstick sampling, arterial sampling, or cervicovaginal fluid collection using an ophthalmic sponge. The biological sample may be any of the samples described for analysis herein. The biological sample may be a fluid, whole blood, peripheral blood, serum, plasma, urine, cervicovaginal secretion, or amniotic fluid sample.

A variety of different treatments may be applied to dissociate a PlGF complex. In some embodiments, the treatment is an elevated temperature; e.g. least 30° C., at least 37° C., or at least 45° C. In some embodiments, the treatment comprises increasing or decreasing the pH (e.g. to less than 6 or greater than 8). In some embodiments, the treatment is a surfactant, such as an anionic surfactant, a cationic surfactant, a zwitterionic surfactant, a nonionic surfactant, SDS, PFOA, cetrimonium bromide (CTAB), cetylpyridinium chloride (CPC), benzalkonium chloride (BAC), benzethonium chloride (BZT), dimethyldioctadecylammonium chloride, dioctadecyldimethylammonium bromide (DODAB), CHAPS (3-[(3-cholamidopropyl)dimethylammonio]-1-propanesulfonate), cocamidopropyl hydroxysultaine, Triton-X-100, tween-20, tween-40-tween-60, or tween-80, or any combination thereof. In some embodiments, the treatment is a chaotropic agent, such as a low concentration of urea or guanidinium hydrochloride. In some embodiments, the treatment is an agent that adjusts the ionic strength of the solution, such as NaCl, KCl, or ammonium chloride.

In some embodiments, the treatment is a steric treatment. Steric treatments include antibodies, antibody fragments or derivatives, aptamers, peptides, proteins, or other agents that bind an epitope of free PlGF or free sFLT, PlGF, or sFLT1 and prevent reassembly of a PlGF/sFLT1complex.

In some embodiments, a PlGF binding or blocking agent is selected based on reference to a published crystal structure of PlGF protein (see e.g. Iyer et al. J Biol Chem. 2001 Apr. 13; 276(15):12153-61. Epub 2000 Nov. 7). In some embodiments, the PlGF binding or blocking agent binds to residues on the PlGF-1 molecule that are involved in recognition of s-Flt-1.

In some embodiments, an agent, or an apparatus for dissociating PlGF (e.g. PlGF complexes) are used in methods, systems, kits, or compositions described herein. Such agent or apparatus can include a device for application for heat to a sample from a subject (e.g. a multiwell plate in combination with a thermocycler or heat block), a pH adjustment agent (e.g. hydrochloric acid solution or sodium/potassium acetate for acidic adjustment, or bicarbonate, sodium hydroxide, or potassium hydroxide for alkaline adjustment), a surfactant (e.g., anionic surfactant, a cationic surfactant, a zwitterionic surfactant, a nonionic surfactant, SDS, PFOA, cetrimonium bromide (CTAB), cetylpyridinium chloride (CPC), benzalkonium chloride (BAC), benzethonium chloride (BZT), dimethyldioctadecylammonium chloride, dioctadecyldimethylammonium bromide (DODAB), CHAPS (3-[(3-cholamidopropyl)dimethylammonio]-1-propanesulfonate), cocamidopropyl hydroxysultaine, Triton-X-100, tween-20, tween-40-tween-60, or tween-80, or any combination thereof), a chaotropic agent (e.g. urea or guanidinium hydrochloride), an ionic strength adjustment agent (e.g., a concentrated solution of NaCl, KCl, or ammonium chloride), or a steric agent. In some embodiments the agent is provided in the form of a concentrated solution. In some embodiments the concentrated solution consists essentially of the reagent. In some embodiments, the concentrated solution has a concentration of the agent of at least 50 mM, at least 100 mM, at least 150 mM, at least 200 mM, at least 250 mM, at least 300 mM, at least 350 mM, at least 400 mM, at least 450 mM, at least 500 mM, at least 550 mM, at least 600 mM, at least 650 mM, at least 700 mM, at least 750 mM, at least 800 mM, at least 850 mM, at least 900 mM, at least 950 mM, at least 1 M, at least 2 M, at least 4M, or at least 5 M.

In some embodiments, dissociated PlGF level or total PlGF level is measured by solid-phase extraction rather than dissociation per se. In some iterations of this embodiment, recombinant sFLT1 or another PlGF binding partner is added to the sample at a supersaturating concentration to bind all free PlGF, and the PlGF complex is captured using an sFLT antibody (or an antibody against the other PlGF binding partner). The captured PlGF is then dissociated from the sFLT (or the other PlGF binding partner) and measured using a PlGF ELISA, immunoassay, or mass spectrometry using standard temperature conditions. In other iterations of this embodiment, PlGF(f) is measured by anion exchange chromatography, cation exchange chromatography, or gel filtration chromatography or filtration by identifying a free PlGF peak separate from the other PlGF complexes.

In some embodiments, following treatment to dissociate a PlGF complex, the PlGF complex is then treated with an agent to prevent reassembly of the PlGF complex with other agents.

In some embodiments, PlGF-d is not determined by dissociation but rather by binding of an antibody, antibody fragment, antibody derivative, aptamer, peptide binder, or protein binder with an alternative epitope to those described herein. In some cases, such an antibody binds PlGF at an epitope that is not blocked by binding of sFLT.

Treatments to dissociate a PlGF complex may be applied for various amounts of time. In some embodiments, the treatment is applied for at least 5, 10, 15, 20, 25, 30, 40, 50, 60, 90, or 120 minutes, or at least 8, 12, or 16 hours.

In some embodiments the first unmodified portion of said biological sample has not been stored at a temperature above about 20° C. In some embodiments, the first unmodified sample is then contacted to a PlGF capture antibody at a temperature of e.g. 30° C., 28° C., 25° C., or 22° C. or less to prevent dissociation any PlGF:sFLT complexes in the sample. In some embodiment, the first unmodified sample is contacted to a PlGF capture antibody with high affinity for a brief period of time to prevent dissociation of any PlGF:sFLT complexes in the sample. In some embodiments, the PlGF is measured in a homogenous assay format (e.g. a format that does not require washing such as TR-FRET, LOCI, or alpha screen) to prevent dissociation of PlGF complexes.

In some embodiments, PlGF-d is measured at multiple time points in the same subject to determine a change in dissociation rate. For example, PlGF-d may be measured every 2, 4, 6, 8, 12, 18, 24, 36, 48, 96, 120, 144, 168 or more hours.

In some embodiments, PlGF-f is not measured by preventing dissociation of PlGF complexes but rather by use of an antibody with an alternative epitope. Such an epitope may be an epitope specifically blocked by sFLT (e.g. a mono-mono antibody).

In some embodiments, PlGF-f is measured by preventing dissociation of other PlGF complexes using addition of a chemical crosslinking agent. Such agents react with labile groups naturally present on protein surfaces (e.g. amino-, sulfhydryl-groups) to covalently stabilize protein-protein interactions. In some embodiments, the crosslinking agent comprises an amine-to-amine crosslinking moiety such as an NHS ester (e.g. DSG, DSS, BS3, TSAT, BS(PEG)5, PS(PEG)9, DSP, DTSSP, DST, BSOCOES, EGS, Sulfo-EGS), an imidoester (e.g. DMA, DMP, DMS, DTBP), or a difluro group (e.g. DFDNB). In some embodiments, the crosslinking agent comprises a sulfhydryl-to-sulfhydryl group crosslinker, such as an NHS-Haloacetyl Crosslinker (e.g. SIA, SBAP, SIAB, Sulfo-SIAB), NHS-maleimide (e.g. AMAS, BMPS, GMBS, sulfo-GMBS, MBS, sulfo-MBS, SMCC, sulfo-SMCC, EMCS, sulfo-EMCS, SMPB, sulfo-SMPB, SMPH, LC-SMCC, sulfo-KMUS), or an NHS-Pyridyldithiol Crosslinker (e.g. SPDP, LC-SPDP, sulfo-LC-SPDP, SMPT, PEG4-SPDP, PEG12-SPDP).

In some embodiments, the measurement of PlGF-f has a LLOQ of less than or equal to 10 pg/ml, 20 pg/ml, 30 pg/ml, 40 pg/ml, 50 pg/ml, or 100 pg/ml. In some embodiments, the measurement of PlGF-d has a LLOQ of less than or equal to 10 pg/ml, 20 pg/ml, 30 pg/ml, 40 pg/ml, 50 pg/ml, or 100 pg/ml.

In some aspects, the present disclosure provides for a method for determining a PlGF-f:PlGF-d ratio in a biological sample comprising PlGF, the method comprising: determining an amount of PlGF-f in a first aliquot of the biological sample by: contacting a first aliquot with a capture reagent for a first time at a first temperature, wherein the PlGF-f binds to the capture reagent to form a PlGF-f-capture reagent complex; contacting the PlGF-f-capture reagent complex with a detector reagent for a second time at a second temperature, wherein the PlGF-f-capture reagent complex binds to the second reagent to form a first ternary complex comprising PlGF-f, the capture reagent, and the detector reagent; and detecting the first ternary complex; and determining an amount of PlGF-d in a second aliquot of the biological sample by: contacting a second aliquot with the capture reagent for a third time at a third temperature, wherein the PlGF-d binds to the capture reagent to form a PlGF-d-capture reagent complex; contacting the PlGF-d-capture reagent complex with the detector reagent for a fourth time at a fourth temperature, wherein the PlGF-d- capture reagent complex binds to the second reagent to form a second ternary complex comprising PlGF-d, the capture reagent, and the detector reagent; and detecting the second ternary complex; wherein a PlGF-s-Flt1 complex is stable at the first temperature and the PlGF-s-Flt1 complex dissociates at the second temperature. In some embodiments, the first temperature is less than 30° C., less than 25° C., between 15° C. and 30° C., between 15° C. and 25° C., between 20° C. and 25° C., or about 22° C. In some embodiments, the second temperature is less than 30 C, less than 25 C, between 15 C and 30 C, between 15° C. and 25° C., between 20° C. and 25° C., or about 22° C. In some embodiments, the third temperature is at least 30° C., at least 35° C., between 30° C. and 45° C., about 30° C., about 37° C. or about 45° C. In some embodiments, the fourth temperature is at least 30° C., at least 35° C., between 30° C. and 45° C., about 30° C., about 37° C. or about 45° C. In some embodiments, the first time is less than 1 hour, less than 45 minutes, between 10 minutes and 30 minutes, about 30 minutes, about 20 minutes, or about 15 minutes. In some embodiments, the second time is less than 1 hour, less than 45 minutes, between 10 minutes and 30 minutes, about 30 minutes, about 20 minutes, or about 15 minutes. In some embodiments, the third time is at least 1 hour, between 1 hour and 3 hours, between 90 minutes and 150 minutes, or about 120 minutes. In some embodiments, the fourth time is at least 1 hour, between 1 hour and 3 hours, between 90 minutes and 150 minutes, or about 120 minutes. In some embodiments, the first time is about 30 minutes, the second time is about 30 minutes, the third time is about 2 hours, the fourth time is about 2 hours, the first temperature is about 22° C., the second temperature is about 22° C., the third temperature is about 37° C., and the fourth temperature is about 37° C. In some embodiments, the second step is conducted in the presence of a blocking antibody that prevents s-FLT from rebinding to PlGF.

Kits

In some embodiments, the disclosure provides assay kits for analysis of any of the sets of biomarkers included herein for the detection of preeclampsia. In some cases, the assay kits comprise one or more antigen-binding reagents. In some embodiments, the one or more antigen-binding reagents comprise combinations of antigen-binding reagents with specificities for the antigens/biomarkers presented below. In some embodiments, the assay kits comprise one or more antigen-binding reagents in combination with a reagent capable of dissociating a PlGF complex, such as a pH adjustment agent (e.g. a solution of sodium or potassium acetate for acidic adjustment or a solution of bicarbonate or sodium/potassium hydroxide for alkaline adjustment), a surfactant (e.g., an anionic surfactant, a cationic surfactant, a zwitterionic surfactant, a nonionic surfactant, SDS, PFOA, cetrimonium bromide (CTAB), cetylpyridinium chloride (CPC), benzalkonium chloride (BAC), benzethonium chloride (BZT), dimethyldioctadecylammonium chloride, dioctadecyldimethylammonium bromide (DODAB), CHAPS (3[(3-cholamidopropyl)dimethylammonio]-1-propanesulfonate), cocamidopropyl hydroxysultaine, Triton-X-100, tween-20, tween-40-tween-60, or tween-80, or any combination thereof), a chaotropic agent (e.g., urea or guanidinium hydrochloride, or a combination thereof), an ionic strength adjustment agent (e.g. a concentrated solution of NaCl, KCl, or ammonium chloride, or a combination thereof) or a steric agent (e.g an antibody, antibody fragment or derivative, aptamer, peptide, protein, or other agent that binds an epitope of free PlGF or free sFLT, PlGF, or sFLT1 and prevent reassembly of a PlGF/sFLT1 complex). In some embodiments, the assay kits comprise one or more antigen-binding reagents described herein in combination with: (a) an antibody, antibody fragment or derivative, aptamer, peptide, protein, or other agent that binds an epitope that reports total (e.g. free plus dissociated) PlGF; and/or (b) an antibody, antibody fragment or derivative, aptamer, peptide, protein, or other agent that binds an epitope that reports free (e.g. without binding to dissociated) PlGF. In some embodiments the reagent capable of dissociating a PlGF complex is provided in the form of a concentrated solution. In some embodiments the concentrated solution consists essentially of the reagent. In some embodiments, the concentrated solution has a concentration of the reagent of at least 50 mM, at least 100 mM, at least 150 mM, at least 200 mM, at least 250 mM, at least 300 mM, at least 350 mM, at least 400 mM, at least 450 mM, at least 500 mM, at least 550 mM, at least 600 mM, at least 650 mM, at least 700 mM, at least 750 mM, at least 800 mM, at least 850 mM, at least 900 mM, at least 950 mM, at least 1 M, at least 2 M, at least 4M, or at least 5 M.

In some embodiments, the one or more antigen-binding reagents comprise antigen-binding reagents with specificities for one or more biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for: (a) sFLT1 or Endoglin; and (b) PlGF (free, dissociated, or % free). In some embodiments, the one or more antigen-binding reagents comprise antigen-binding reagents with specificities for: (a) sFLT1 or Endoglin; (b) PlGF (free, dissociated, or % free); and (c) KIM1. In some embodiments, the one or more antigen-binding reagents comprise antigen-binding reagents with specificities for: (a) sFLT1 or Endoglin; (b) PlGF (free, dissociated, or % free); (c) KIM1; and (d) FGF21. In some embodiments, the one or more antigen-binding reagents comprise antigen-binding reagents with specificities for: (a) sFLT1 or Endoglin; (b) PlGF (free, dissociated, or % free); (c) KIM1; and (d) Decorin. In some embodiments, the one or more antigen-binding reagents comprise antigen-binding reagents with specificities for: (a) sFLT1 or Endoglin; (b) PlGF (free, dissociated, or % free); (c) KIM1; (d) FGF21; and (e) Decorin.

In some embodiments, the one or more antigen-binding reagents comprise antigen-binding reagents with specificities for: (a) sFLT1; (b) Endoglin; and (c) PlGF (free, dissociated, or % free). In some embodiments, the one or more antigen-binding reagents comprise antigen-binding reagents with specificities for: (a) sFLT1; (b) Endoglin; (c) PlGF (free, dissociated, or % free); and (d) KIM1. In some embodiments, the one or more antigen-binding reagents comprise antigen-binding reagents with specificities for: (a) sFLT1; (b) Endoglin; (c) PlGF (free, dissociated, or % free); (d) KIM1; and (e) FGF21. In some embodiments, the one or more antigen-binding reagents comprise antigen-binding reagents with specificities for: (a) sFLT1; (b) Endoglin; (c) PlGF (free, dissociated, or % free); (d) KIM1; and (e) Decorin. In some embodiments, the one or more antigen-binding reagents comprise antigen-binding reagents with specificities for: (a) sFLT1; (b) Endoglin; (c) PlGF (free, dissociated, or % free); (d) KIM1; (e) FGF21; and (f) Decorin.

In some embodiments, the one or more antigen-binding reagents comprise antigen-binding reagents with specificities for two or more biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for three or more biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for four or more biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for five or more biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for six or more biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for seven or more biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for all of sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for two biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for three biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for four biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for five biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for six biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for seven biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for no more than two biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for no more than three biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for no more than four biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for no more than five biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for no more than six biomarkers selected from sFLT, free sFLT, Endoglin, KIM-1, FGF21, Decorin, Clec4A and CD274 in combination with PlGF(f), PlGF(d), or PlGF (% free). In some embodiments, the one or more antigen-binding reagents comprise antigen-binding reagents with specificities for no more than seven biomarkers selected from sFLT, free sFLT, Endoglin, KIM-1, FGF21, Decorin, Clec4A and CD274 in combination with PlGF(f), PlGF(d), or PlGF (% free).

In some embodiments, the assay kit provided is suitable for a multiplex homogenous biomarker assay, suitable for detection of all the analytes in a single reaction (e.g. in the same solution compartment). In such assays, multiple antibodies or antigen detection reagents that bind to separate epitopes are provided against the same analyte/biomarker, and detection of coincident binding/interaction of both antibodies to the same molecule of analyte/biomarker serves to detect the analyte/biomarker in the sample. Thus, such kits provide two antibodies or antigen-binding reagents against each analyte.

In the case of a multiplex homogenous biomarker assay detectable by TR-FRET, such kits provide a pair of antibodies or antigen-binding reagents for each analyte conjugated to a complementary pair of FRET dyes, wherein one antibody or antigen-binding reagent of the pair is conjugated to a FRET donor and the other is conjugated to a FRET acceptor. In the case of a multiplex homogenous biomarker assay detectable by LOCI, such kits provide a pair of antibodies or antigen-binding reagents wherein one antibody or antigen-binding reagent of the pair is conjugated to a photosensitizer and the other antibody or antigen-binding reagent of the pair is conjugated to an oxygen sensitive dye.

In some embodiments, the assay kit provided is suitable for a multiplex non-homogenous biomarker assay suitable for detection of all the analytes in separate reactions (e.g. in separate solution compartments). In some embodiments of such assays (e.g. sandwich ELISA), antibodies or antigen binding reagents against the relevant set of biomarkers are provided attached to a substrate (e.g. in a well of a multiwell plate, or in a lateral flow assay lane). A second free antibody against each of the biomarkers provided attached to the substrate is also provided; this antibody can be labeled (e.g. with a fluorescent dye, with a chemiluminescent enzyme, or a luminescent enzyme) or unlabeled. In the case where an unlabeled antibody is provided, a secondary labeled (e.g. with a fluorescent dye, with a chemiluminescent enzyme, or a luminescent enzyme) antibody or antigen-binding reagent is provided which has binding specificity against the second free antibody.

In some embodiments, the kit is for use as an in vitro diagnostic kit that includes one or more cartridges with reagents for testing on third-party platforms. Data collected from third-parties could be uploaded to a server (the cloud), put through a model/algorithm, and results can be shared with a doctor or other medical practitioner. Kits may also include instructions for use (e.g., according to any of the methods described herein).

In some embodiments, the assay kits comprise apparatus for collecting a biological sample from a pregnant female subject. Such apparatus can include, but is not limited to, an ophthalmic sponge or collection tube, with or without any reagents or preservatives necessary for sample preparation or stable storage (e.g. any of anti-microbials such as sodium azide and sodium fluoride, anti-coagulants such as EDTA, sodium citrate, potassium oxalate, heparin, and acid citrate dextrose, or fixatives such as methanol, ethanol, and formaldehyde). Collection tubes may be configured for or suitable for collection of any of the samples described herein, such as blood, peripheral blood, serum, plasma, urine, cervicovaginal mucus, or saliva. Collection tubes include e.g., red-top tubes; mottled red/gray-top, gold-top, or cherry red-top (gel-barrier) tubes; lavender-top tubes, and gray-top tubes.

In some embodiments, the assay kits comprise apparatus facilitating any of the assays described herein. Such apparatus can include, but is not limited to, lateral flow strips or multiwell plates containing any of the antibodies or antigen-binding fragments thereof described herein conjugated or adsorbed to a surface thereof.

In some embodiments, the assay kits comprise instructions for carrying out any of the assays described herein. Such assays include immunoassays, ELISA assays, sandwich ELISA assays, TR-FRET assays, proximity extension assays, amplified luminescent proximity (LOCI) assays, or luminescent oxygen channeling immunoassays.

In some cases, the assay kits comprise no more than 20, no more than 15, no more than 10, no more than 9, no more than 8, no more than 7, no more than 6, nor more than 5, no more than 4, no more than 3, no more than 2, or no more than 1 probes, antibodies, or antigen binding fragments or derivatives of antibodies specific for any of the biomarkers described herein.

EXAMPLES

Example 1. —Development of Assays for Free and Dissociated PlGF Protein

During the development of an ELISA capture assay for PlGF from patient sera, it was discovered that there was a divergence in values measured from samples using different assay protocols. This divergence was only in samples with a high sFLT concentration. Further testing identified the assay temperature as a putative source of the divergence: room temperature and 30° C. incubations yielded divergent results.

The dependence of the phenomenon on temperature and sFLT concentration indicated the phenomenon might be the result of dissociation of PlGF complexes at higher assay temperatures. Specifically, it was hypothesized that variable dissociation of PlGF:sFLT 1:1 and PlGF:sFLT 2:1 complexes during the ELISA capture assay at high temperature might lead to artificial increases in the measured "free PlGF" during the assay protocol (see FIG. 1A and FIG. 1B).

Figure 2A:
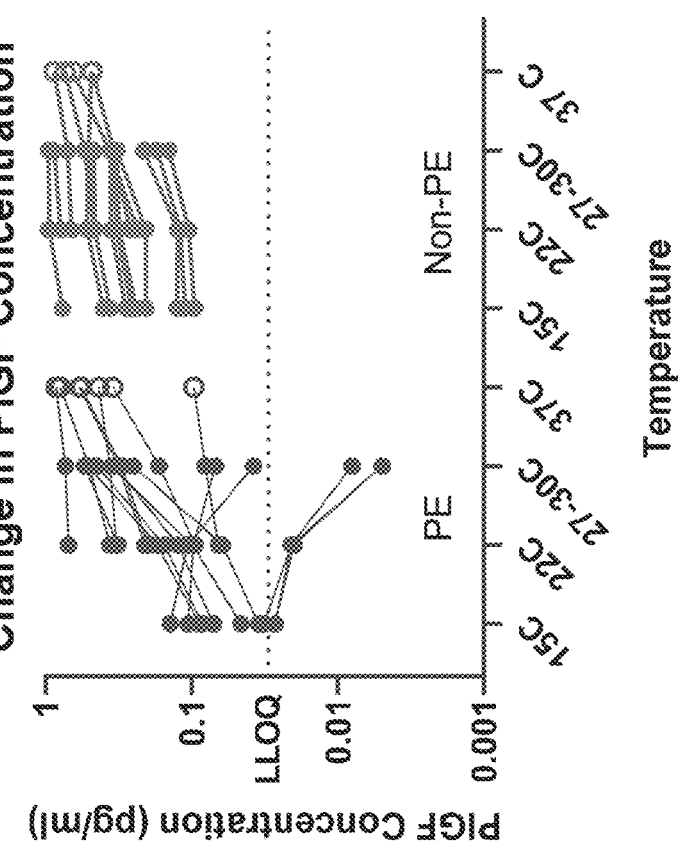

Accordingly, experiments were performed to directly determine the relationship between temperature, time, sFLT levels, and measured PlGF levels. In a first experiment, serum samples from pregnant women identified as preeclamptic (PE) or non-preeclamptic (non-PE) by later clinical outcome were exposed measured by ELISA at various temperatures between 15° C. and 37° C. during incubation with PlGF capture antibodies, as well as after washing and during incubation with PlGF labeled detection antibody (see FIG. 2A). ELISAs performed at 37° C. showed higher detected PlGF concentrations than those performed at 15° C., and this effect was stronger in PE samples (which tend toward higher sFLT concentrations).

These data indicated that % free PlGF values (measured as a ratio of "naturally" free PlGF versus in-vitro dissociated PlGF) could be measured using this dissociation phenomenon and have value in generating more accurate PlGF-based prediction of preeclamptic patients.

Figure 3A:
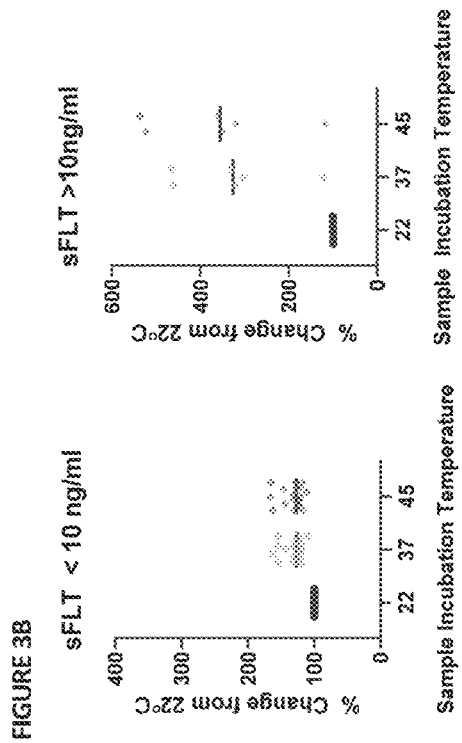
FIGS. 3A and 3B illustrate the effects of various capture temperatures and sFLT concentrations on the detection of PlGF using 3rd trimester pregnancy samples.
Figure 3B:
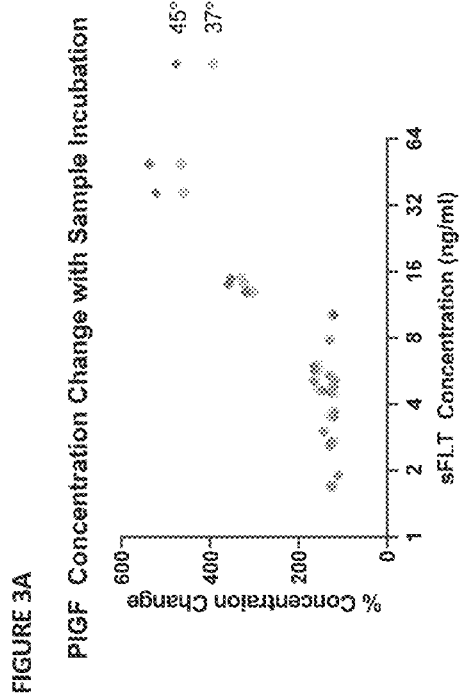

Accordingly, experiments were first performed on third-trimester pregnant patient serum samples naturally containing various quantities of sFLT (e.g. 1-64 ng/ml sFLT and applying various incubation conditions (2 hours capture at 37° C. or 45° C., while keeping incubation with detection antibody after wash at 22° C.) to the serum samples to optimize capture incubation time (see FIG. 3A). Samples with "high" sFLT (>10 ng/ml, which would favor formation of the 1:1 and 2:1 PlGF:sFLT complex) showed larger % changes in detected PlGF concentration than samples with "low" sFLT (<10 ng/ml, which would favor "free" PlGF) sFLT when incubated at 37° C., and incubation at a higher temperature such as 45° C. showed minimal additional benefit (see FIG. 3B). This indicated that 37° C. was adequate to dissociate PlGF heteromultimers in solution.

Next, incubation time for capture was optimized. First, a separate set of third-trimester serum samples also containing variable sFLT concentrations as above (e.g. 1-64 ng/ml sFLT) to capture incubations at 37° C. for various different incubation times, varying capture and post-wash detection incubation times simultaneously (see FIG. 4A, where the x-axis shows the incubation time used for both the PlGF capture and detection incubation). While samples with sFLT <4 ng/ml and >25 ng/ml diverged in measured PlGF concentrations at short incubation times, measured PlGF concentrations in all samples converged when the incubation was extended to 120 minutes, indicating that a capture time of 120 minutes was adequate to dissociate and capture PlGF from PlGF:sFLT complexes. Second, because of the promising results at 120 minutes, the mixtures of PlGF and sFLT were subjected to additional capture time/detection time combinations including an overnight capture incubation (see FIG. 4B, where the times are listed in order of capture time/detection incubation time; and FIG. 4C); this demonstrated that overnight capture may have some advantages over 120 min but that the differences are minimal. Third, capture incubation times for solutions containing only recombinant PlGF of different concentrations was measured, to verify that the capture times determined for the PlGF:sFLT mixtures was also applicable to measure PlGF alone with maximal sensitivity (see FIG. 4D) When capture incubation times were tested for various PlGF concentrations, it was also found that a 2 hr incubation maximized sensitivity for measuring PlGF.

Standard protocols for PlGF-f and PlGF-d quantification were established based on the results of temperature and time optimization. PlGF-f is measured at less than 22° C. with a 30-minute capture incubation a 30-minute detector incubation; and PlGF-d is measured at 37° C. with a 2-hour capture incubation and a 2-hour detector incubation. For comparison, the legacy PlGF ELISA protocol (PlGF(II)) had intermediate conditions with a 1-hour capture incubation and a 1-hour detector incubation is measured at 30° C.

Figure 5B:
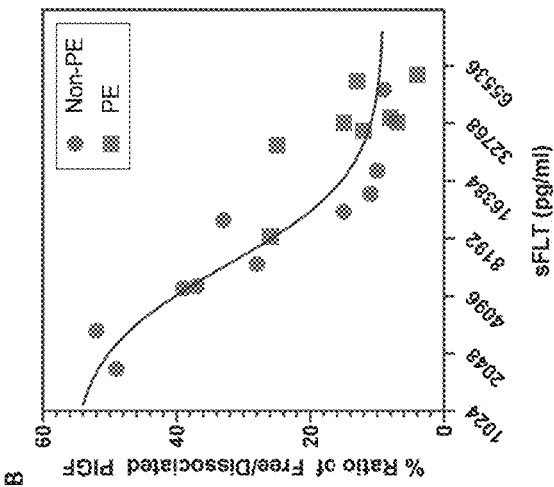
FIGS. 5A and 5B illustrate a pilot study of where PlGF was measured at various temperatures—22° C. for PlGF(f), 30° C. for PlGF(II), and 37° C. for PlGF(d)—and in the presence of various amounts of sFLT in serum from patients with and without preeclampsia.
Figure 5A:
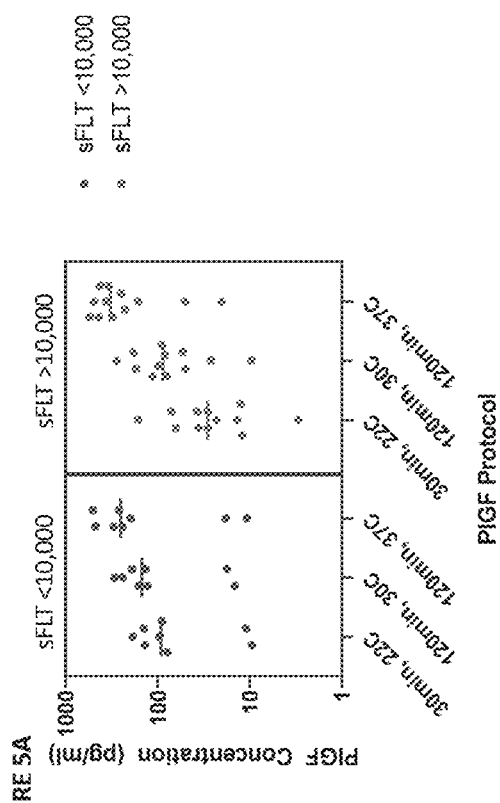

Finally, using these optimized conditions, PlGF (free) and PlGF (dissociated) conditions were measured from patient serum samples (see FIG. 5A, where the samples are segregated into high and low sFLT concentrations in the left and right panels). As, expected, more PlGF was detected in the PlGF(d) conditions, especially at higher sFLT concentrations. Accordingly, this protocol was applied to measure PlGF-f:PlGF-d ratios in a set of pregnant patient serum samples containing (n=10) preeclamptic samples and (n=15) non-preeclamptic samples (see FIG. 5B, where PlGF ratio is plotted versus sFLT concentration). Measurement of the PlGF f:d ratio in these samples revealed a population of low-sFLT, non-PE samples (see leftmost red dots in FIG. 5B), and also provided separation between PE samples and higher sFLT non-PE samples, indicating that the f:d ratio may improve of the ability to discriminate between PE and non-PE populations in a screening test compared to the PlGF/sFLT ratio used in a commercially available screening test.

Figure 7A:
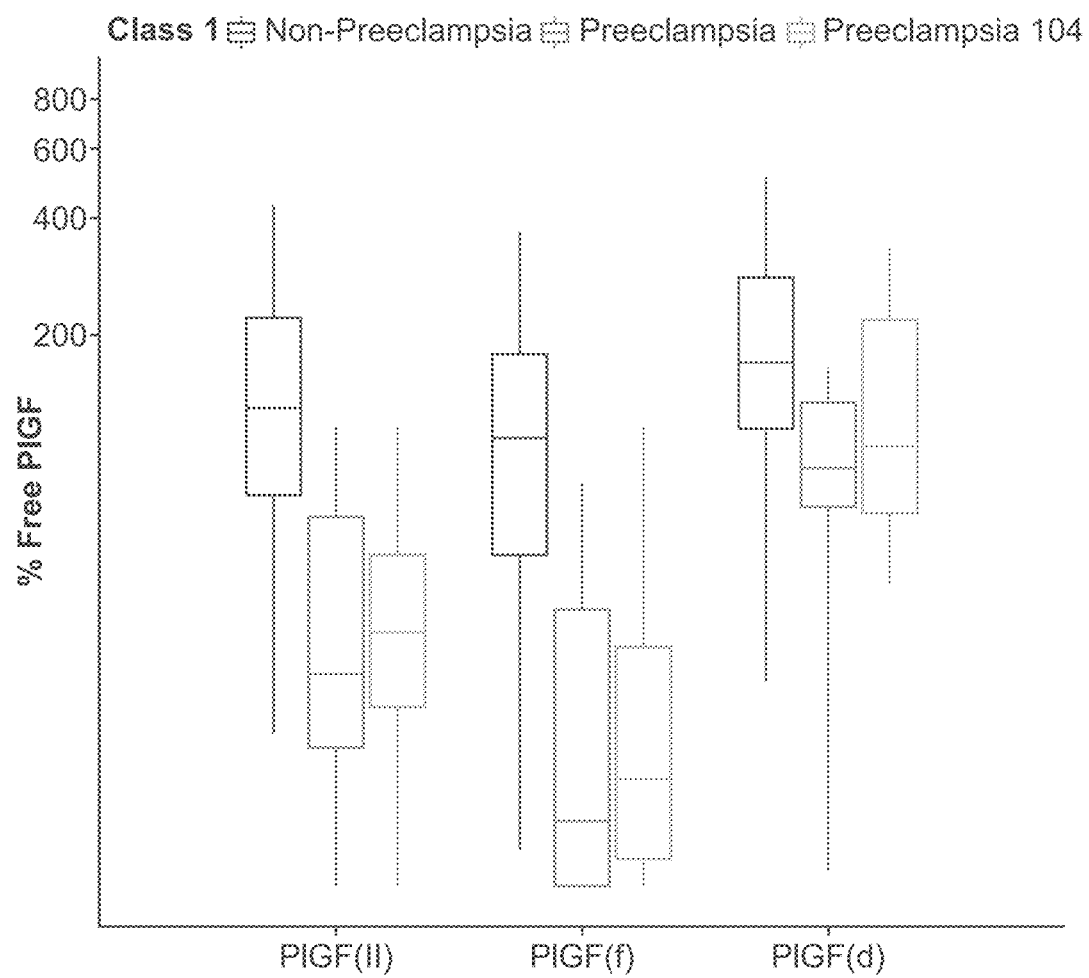
FIGS. 7A, 7B, and 7C show PlGF measurements of a larger set of PE and non-PE serum samples using different protocols for measuring species of PlGF—22 C for PlGF(f), 30 C for PlGF(II), and 37 C for PlGF(d)—and in the presence of various amounts of sFLT, demonstrating that % free PlGF can improve separation of PE from non-PE samples.
Figure 7B:
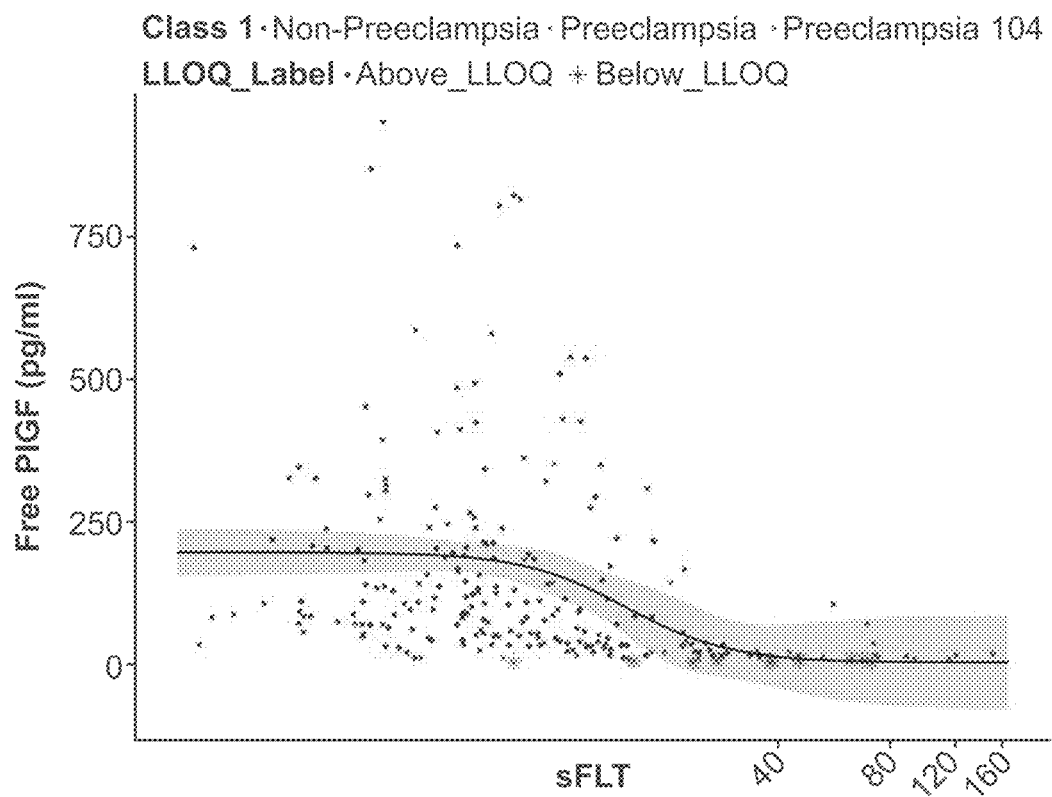
Figure 7C:
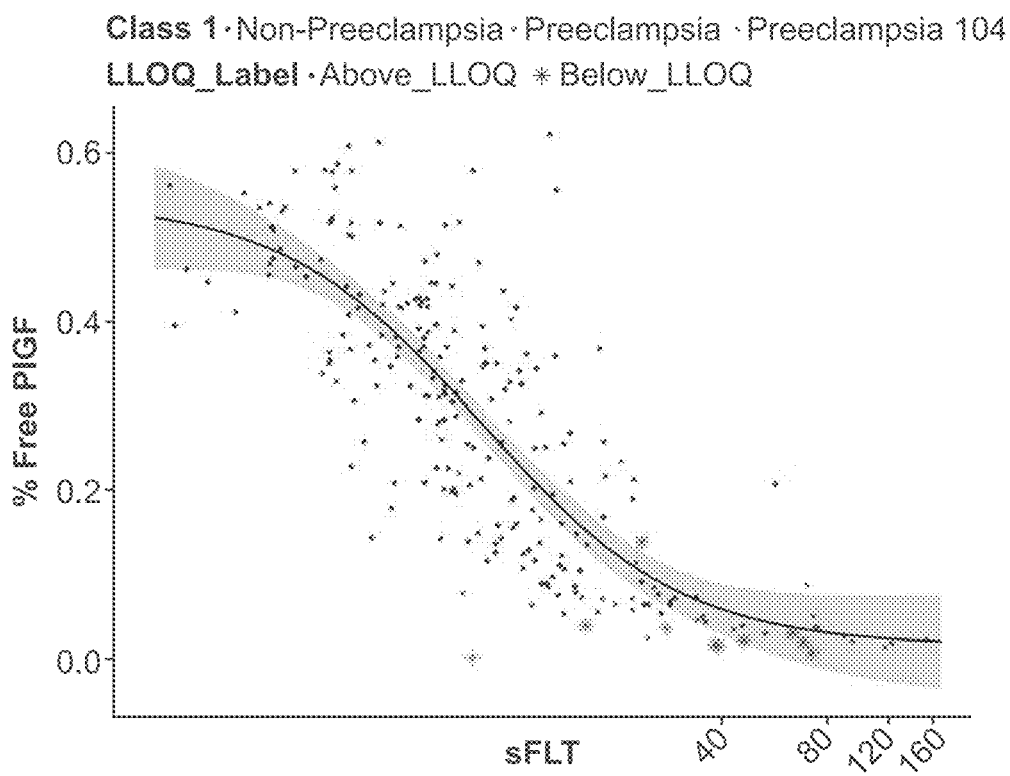

Based on the results in a limited set of pregnant patient PE/non-PE samples, the PlGF f:d ratio was determined for a larger set of PE-nonPE pregnant patient samples from two recent studies (PE-104 and PE-105, described herein, see Example 3). FIG. 6 shows plots of PE and non-PE patients from the studies segregated using PlGF(f) conc or % free PlGF ((f)/(d)×100) demonstrating that both show improved separation of PE samples from non-PE samples. FIG. 7A shows the -f and -d levels measured for preeclamptic and non-preeclamptic patients alongside results from the legacy PlGF assay ("PlGF(II)", which was determined above to measure intermediate concentrations of dissociated PlGF). PlGF(f) provided better discrimination between PE and non-PE samples than PlGF(II) or PlGF(d) individually. Graphing the same data as free PlGF versus sFLT (FIG. 7B) and % free PlGF vs sFLT (FIG. 7C) demonstrated that use of a PlGF f:d ratio (such as % free PlGF) increased the dynamic range of PlGF measurement between non-PE and PE samples and improved their separation (see blue vs orange dots in FIGS. 7B and 7C).

Figure 8:
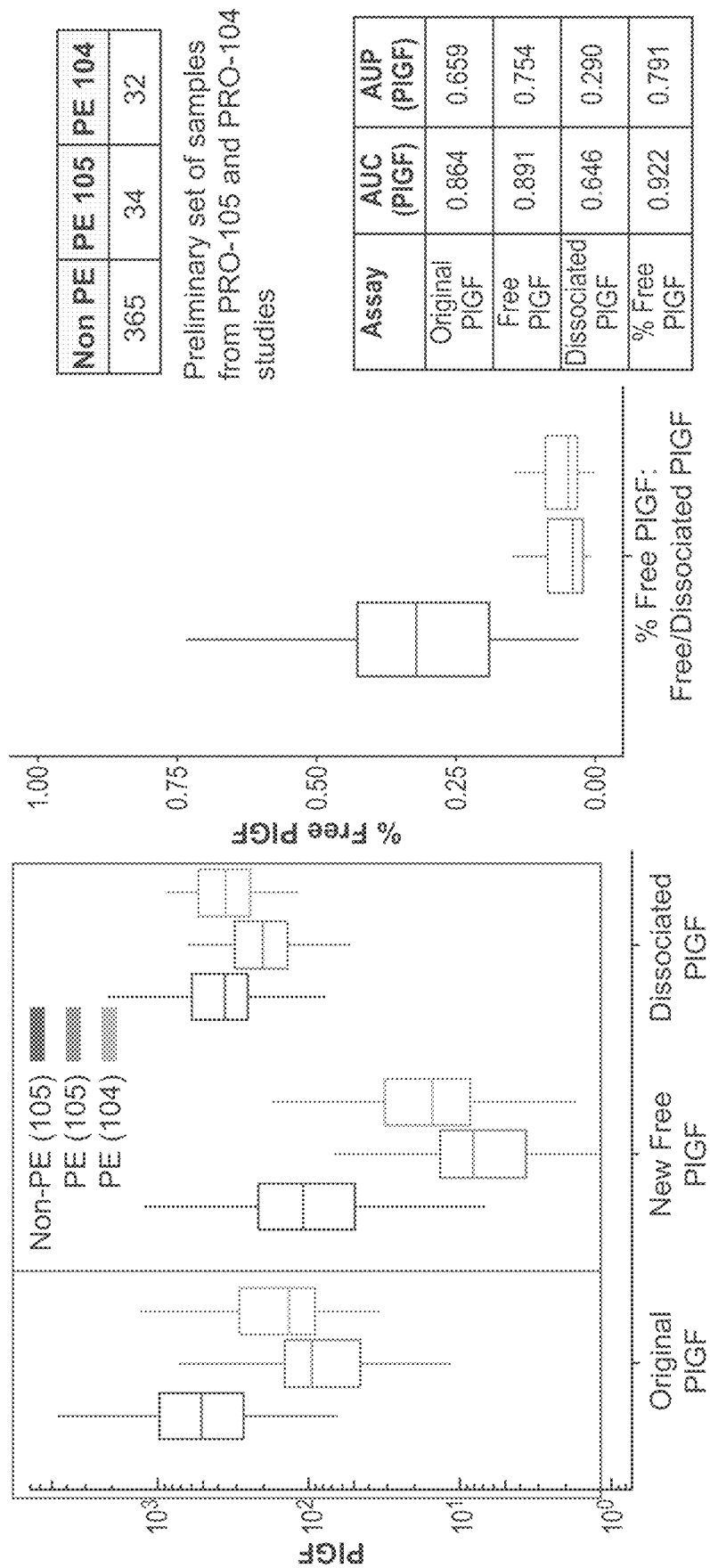
FIG. 8 illustrates determination of performance metrics for PlGF(f), PlGF(d), and PlGF (% f) alongside the old PlGF protocol ("PlGF(II)" as markers to discriminate PE from non-PE patients.
Figure 9:
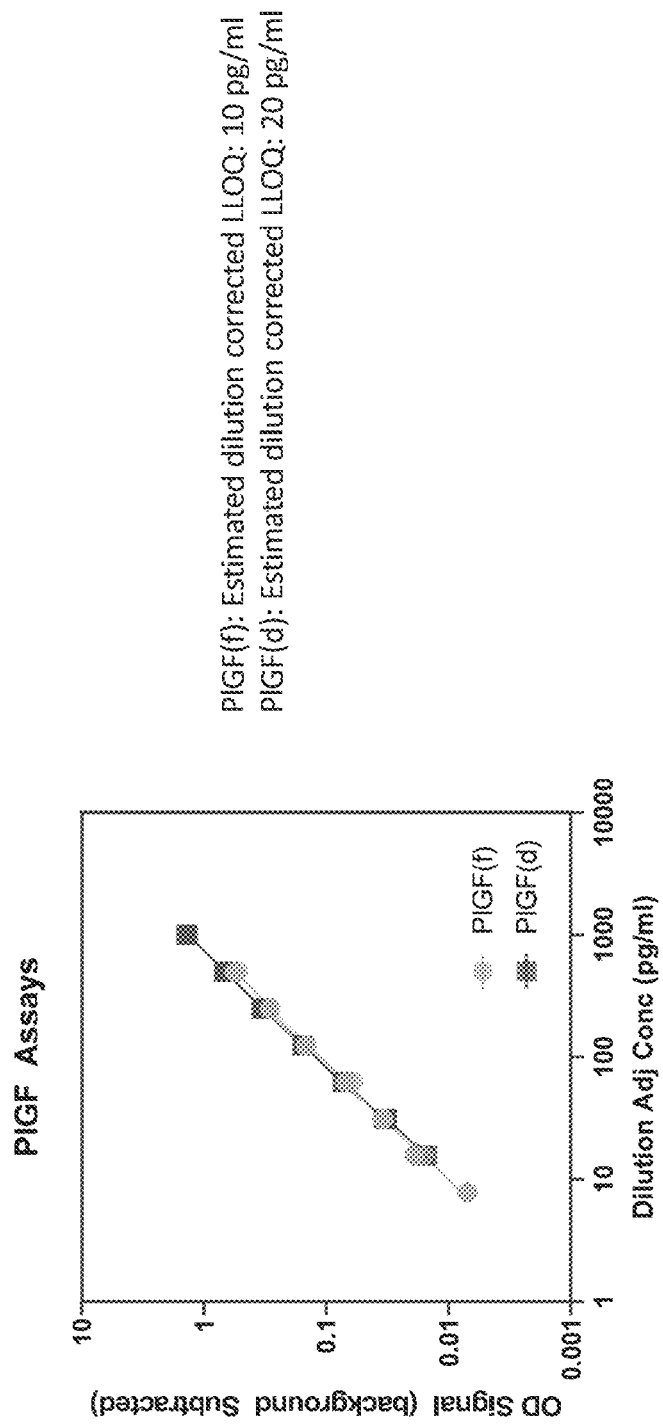
FIG. 9 illustrates a calibration curve using recombinant PlGF using the optimized conditions described in Example 2 which was used to estimate LLOQ for PlGF(f) (10 pg/ml) and PlGF(d) (20 pg/ml) species.

Accordingly, formal performance statistics including were calculated for PlGF(f), PlGF(d), PlGF (% f), and PlGF(II) (the old PlGF measurement protocol) to discriminate PE from non-PE pregnant patient serum samples using this data set (see FIG. 8). Use of either the PlGF(f) or PlGF (% f) showed improvements of both AUC and AUP versus the previous assay conditions that measured an indeterminate amount of PlGF(f) and PlGF(d), indicating that the free and percent free PlGF metrics may add additional discrimination power to biomarker assays using PlGF to detect preeclampsia.

Figure 10:
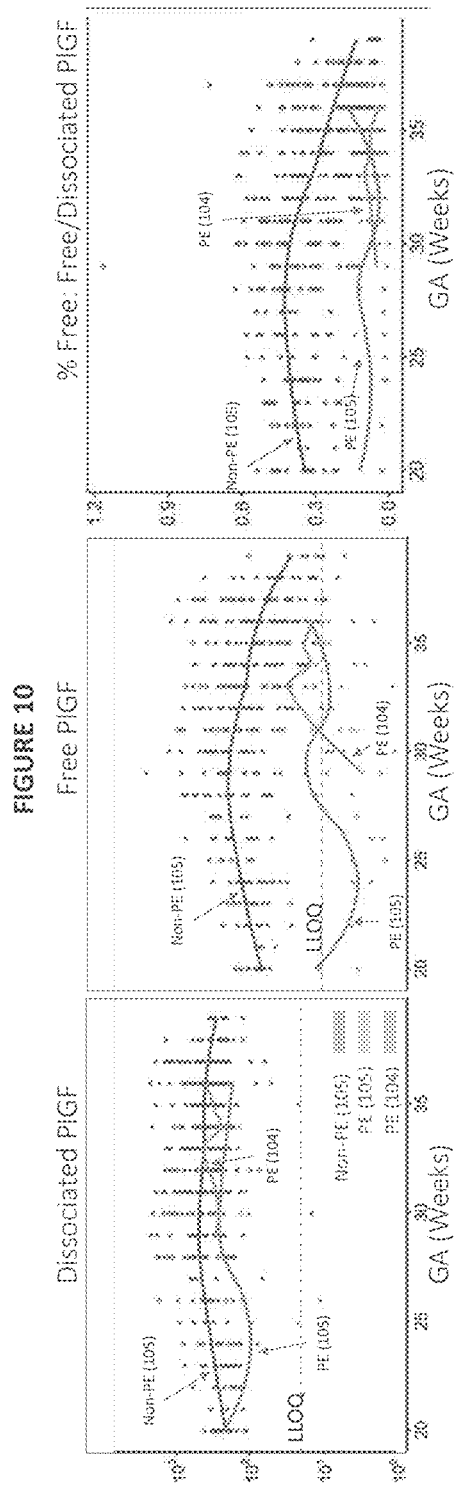
FIG. 10 illustrates analysis of PlGF(d), PlGF(f), and PlGF (% free) versus gestational age (GA), showing that free PlGF offers a robust segregation into earlier gestational age (<28 weeks), indicating that free PlGF (or modifications thereof) could further enable stratification of the preeclampsia cohort at earlier gestational ages. The separation of non-PE and PE lines for dissociated PlGF, free PlGF, and % free PlGF indicates that the ratio of free to dissociated PlGF can allow for normalization within a patient while maintaining separation between non-PE and PE samples. Further, it appears low dissociated PlGF may identify a subset of patients with a different risk profile.

Lastly, an analysis of PlGF(f), PlGF(d), and PlGF (% free) was performed versus gestational age using pregnant patient serum samples from the PE-104 and PE-105 studies (see FIG. 10). The graphs demonstrate that free PlGF improves segregation of non-PE/PE samples into earlier gestational age (<28 weeks), indicating that the marker could further enable stratification of the disease cohort at earlier gestational ages. Further, the graphs indicate that the amount of dissociated PlGF is not a function of the gestational age, and that onset of the disease may be triggered by dissociation/ cleavage of FLT from the cell surface into the free form (sFlt) which subsequently binds to PlGF and results in reduction of free PlGF. Finally, the graphs indicate that as the free PLGF naturally decreases from 30 weeks gestational age onward, such information can further be used to control the false positive rate when interrogating the serum for free PlGF.

Example 2.—Optimized Protocol for Detection of PlGF (Free) and PlGF (Dissociated)

Blood samples are collected from pregnant patients using red top blood collection tubes; the tubes are allowed to clot at room temperature for 30-60 minutes, are centrifuged 20 minutes at 1300 g to remove the clot and are aliquoted for long term storage at below −80° C.

Measurement of PlGF (Free)

Blood samples are collected from pregnant patients using red top blood collection tubes; the tubes are allowed to clot at room temperature for 30-60 minutes, are centrifuged 20 minutes at 1300 g to remove the clot and are aliquoted for long term storage below −80° C.

Measurement of PlGF (Free)

R&D Systems Quantikine kit (Catalog number DPG00) is used to measure the free form of PlGF [PlGF(f)]. In brief, 100 ul of assay diluent RD1-22 (part #895490) is added to each well of the PlGF microplate coated with the monoclonal anti-PlGF antibody (part #890509). Each sample is diluted 1:2 in calibrator diluent RD6-11 (part #895489) and 100 ul of a diluted serum sample is aliquoted into each well of the 96-well plate. The serum samples are incubated in the plate with low shaking for 30 minutes at ambient temperature. Following incubation, the sample from each well of the plate was aspirated and the well was not washed. During a second incubation addition of 200 ul of PlGF conjugate (part #890510) per well is incubated with low shaking for 30 minutes at ambient temperature, followed by washing 4 times with 400 ul of wash solution. This is followed by adding 200 ul TMB substrate solution (Enhanced K-Blue TMB from Neogen, part #308177) in each well and left to incubate for 30 minutes at ambient temperature with low shaking. Finally, the reaction is stopped with the addition of 50 ul of stop solution (2N sulfuric acid from Honeywell part #35276-1L) and the optical density of each well is measured using a microplate reader set at 450 nm.

Measurement of PlGF (Dissociated)

R&D Systems Quantikine kit (Catalog number DPG00) is used to measure the dissociated form of PlGF (PlGF(d)]. In brief, 100 ul of assay diluent RD1-22 (part #895490) is added to each well of the PlGF microplate coated with the monoclonal anti-PlGF antibody (part #890509). Each sample is diluted 1:2 in calibrator diluent RD6-11 (part #895489) and 100 ul of a diluted serum sample is aliquoted into each well of the 96-well plate. The serum samples are incubated in the plate with low shaking for 120 minutes at 37° C. Following incubation, the sample from each well of the plate was aspirated and the well was not washed. During a second incubation addition of 200 ul of PlGF conjugate (part #890510) per well is incubated with low shaking for 120 minutes at 37° C., followed by washing 4 times with 400 ul of wash solution. This if followed by adding 200 ul TMB substrate solution (Enhanced K-Blue TMB from Neogen, part #308177) in each well and left to incubate for 20 minutes at 37° C. with low shaking. Finally, the reaction is stopped with the addition of 50 ul of stop solution (2N sulfuric acid from Honeywell part #35276-1L) and the optical density of each well is measured using a microplate reader set at 450 nm.

Example 3.—Studies Used as Sources of PE and Non-PE Samples

Samples from two studies were used to develop embodiments of new, improved PlGF assays described herein: PRO-105 and PRO-104.

PRO-105: Pregnant women who were 18 years or older (20 weeks to 39 weeks of gestation at first visit) with suspected preeclampsia (based on new onset symptoms, elevated blood pressure, proteinuria, edema or others) were selected for participation in the PRO-105 study. Baseline procedures were performed, including collection of demographic, medical and obstetric histories, list of concomitant medications, weight, height, blood pressure, and other clinical information, as well as obtaining blood and urine samples for use in biomarker assays. After discharge, all patients in the study were followed by interim research visits every 14 days (+/−3 days). For patients who developed PreE, the time (in days) from baseline sampling, the gestational age at diagnosis, and the severity of the disease was recorded. Patients who did not develop preeclampsia before or at delivery were included in the NEGATIVE-PRE-E CONTROL (NonPreE) group. For these NEGATIVE PRE-E CONTROLS, the time from baseline sampling (in days) to either delivery or loss to follow-up was recorded.

The interim study visits occurred every 14 days [+/−3 days] and continued until the subject either: 1) reached 37 weeks' gestation, 2) developed PreE, 3) delivered, or 4) was lost to follow-up.

Delivery outcomes (maternal and neonatal clinical information) were collected on all subjects enrolled in the study. Additionally, if possible, during admission for delivery, blood and urine samples were collected for analysis at delivery.

The study demographics are presented below in Table 1A:

TABLE 1A

Demographic and Clinical Variables for PRO-105 Study

| Demographic and Clinical Variables Demographic | Missing (n = 12) | Clinical Study PRO-105 (n = 1277) | | |
|---|---|---|---|---|
| | | 18 2/7 to 27 6/7 (n = 337) | 28 0/7 to 34 6/7 (n = 550) | 35 0/7 to 36 6/7 (n = 378) |
| Maternal Age (median, IQR) | NA | 30 (8) | 29 (8) | 30 (9) |
| under 25 | 0 (0.00%) | 67 (19.88%) | 124 (22.55%) | 73 (19.31%) |
| 25 to 29 | 0 (0.00%) | 88 (26.11%) | 172 (31.27%) | 108 (28.57%) |
| 30 to 34 | 0 (0.00%) | 101 (29.97%) | 148 (26.91%) | 100 (26.46%) |
| 35 to 39 | 0 (0.00%) | 64 (18.99%) | 88 (16.00%) | 75 (19.84%) |
| 40 to 45 | 0 (0.00%) | 17 (5.04%) | 18 (3.27%) | 22 (5.82%) |
| Missing | 12 (100.00%) | 0 (0.00%) | 0 (0.00%) | 0 (0.00%) |
| BMI (median, IQR) | NA | 36.21 (12.63) | 35.88 (11.28) | 37.44 (10.93) |
| Underweight (<18.5) | 0 (0.00%) | 0 (0.00%) | 0 (0.00%) | 0 (0.00%) |
| Normal (18.5 through 24 BMI) | 0 (0.00%) | 25 (7.42%) | 29 (5.27%) | 20 (5.29%) |
| Overweight (25 through 29 BMI) | 0 (0.00%) | 59 (17.51%) | 88 (16.00%) | 58 (15.34%) |
| Obese-class 1 (30 through 34 BMI) | 0 (0.00%) | 71 (21.07%) | 132 (24.00%) | 69 (18.25%) |
| Obese-class 2 (35 through 39 BMI) | 0 (0.00%) | 59 (17.51%) | 129 (23.45%) | 98 (25.93%) |
| Obese-class 3 (40 or greater BMI) | 0 (0.00%) | 123 (36.50%) | 170 (30.91%) | 132 (34.92%) |
| Missing | 12 (100.00%) | 0 (0.00%) | 2 (0.36%) | 1 (0.26%) |

TABLE 1A-continued

Demographic and Clinical Variables for PRO-105 Study

| Demographic and Clinical Variables Demographic | Missing (n = 12) | Clinical Study PRO-105 (n = 1277) | | |
|---|---|---|---|---|
| | | 18 2/7 to 27 6/7 (n = 337) | 28 0/7 to 34 6/7 (n = 550) | 35 0/7 to 36 6/7 (n = 378) |
| Race | | | | |
| American Indian or Alaskan Native | 0 (0.00%) | 1 (0.30%) | 1 (0.18%) | 0 (0.00%) |
| Asian | 0 (0.00%) | 3 (0.89%) | 7 (1.27%) | 7 (1.85%) |
| Black or African American | 0 (0.00%) | 114 (33.83%) | 194 (35.27%) | 143 (37.83%) |
| Native Hawaiian or Other Pacific Islander | 0 (0.00%) | 1 (0.30%) | 0 (0.00%) | 1 (0.26%) |
| White | 0 (0.00%) | 204 (60.53%) | 335 (60.91%) | 221 (58.47%) |
| Two or more races | 0 (0.00%) | 0 (0.00%) | 0 (0.00%) | 0 (0.00%) |
| Unknown | 0 (0.00%) | 13 (3.86%) | 12 (2.18%) | 6 (1.59%) |
| Refused | 0 (0.00%) | 1 (0.30%) | 1 (0.18%) | 0 (0.00%) |
| Ethnicity | | | | |
| Hispanic or Latino | 0 (0.00%) | 10 (2.97%) | 16 (2.91%) | 13 (3.44%) |
| Not Hispanic or Latino | 0 (0.00%) | 214 (63.50%) | 361 (65.64%) | 273 (72.22%) |
| Unknown/Not Provided | 12 (100.00%) | 113 (33.53%) | 173 (31.45%) | 92 (24.34%) |
| Pregnancy History | | | | |
| Gestational Age (GA) at Enrollment (median, IQR) | NA | 23.71 (4.29) | 32 (3.29) | 36.71 (1.85) |
| <28 0/7 | 0 (0.00%) | 337 (100.00%) | 0 (0.00%) | 0 (0.00%) |
| 28 0/7 to 28 6/7 | 0 (0.00%) | 0 (0.00%) | 72 (13.09%) | 0 (0.00%) |
| 29 0/7 to 29 6/7 | 0 (0.00%) | 0 (0.00%) | 55 (10.00%) | 0 (0.00%) |
| 30 0/7 to 30 6/7 | 0 (0.00%) | 0 (0.00%) | 65 (11.82%) | 0 (0.00%) |
| 31 0/7 to 31 6/7 | 0 (0.00%) | 0 (0.00%) | 75 (13.64%) | 0 (0.00%) |
| 32 0/7 to 32 6/7 | 0 (0.00%) | 0 (0.00%) | 95 (17.27%) | 0 (0.00%) |
| 33 0/7 to 33 6/7 | 0 (0.00%) | 0 (0.00%) | 87 (15.82%) | 0 (0.00%) |
| 34 0/7 to 34 6/7 | 0 (0.00%) | 0 (0.00%) | 101 (18.36%) | 0 (0.00%) |
| 35 0/7 to 35 6/7 | 0 (0.00%) | 0 (0.00%) | 0 (0.00%) | 96 (25.40%) |
| 36 0/7 to 36 6/7 | 0 (0.00%) | 0 (0.00%) | 0 (0.00%) | 112 (29.63%) |
| >= 37 0/7 | 0 (0.00%) | 0 (0.00%) | 0 (0.00%) | 170 (44.97%) |
| Missing | 12 (100.00%) | 0 (0.00%) | 0 (0.00%) | 0 (0.00%) |
| Gravidity (median, IQR) | NA | 3 (3) | 2 (2) | 2 (3) |
| 1 | 0 (0.00%) | 39 (11.57%) | 113 (20.55%) | 96 (25.40%) |
| >1 | 0 (0.00%) | 238 (70.62%) | 350 (63.64%) | 256 (67.72%) |
| Missing | 12 (100.00%) | 60 (17.80%) | 87 (15.82%) | 26 (6.88%) |
| # of births (median, IQR) | NA | 1 (2) | 1 (2) | 1 (2) |
| Nulliparous (0) | 0 (0.00%) | 59 (17.51%) | 138 (25.09%) | 123 (32.54%) |

TABLE 1A-continued

Demographic and Clinical Variables for PRO-105 Study

| Demographic and Clinical Variables | Missing (n = 12) | Clinical Study PRO-105 (n = 1277) 18 2/7 to 27 6/7 (n = 337) | 28 0/7 to 34 6/7 (n = 550) | 35 0/7 to 36 6/7 (n = 378) |
|---|---|---|---|---|
| >0 | 0 (0.00%) | 144 (42.73%) | 217 (39.45%) | 138 (36.51%) |
| Missing | 12 (100.00%) | 134 (39.76%) | 195 (35.45%) | 117 (30.95%) |
| History of Previous Preeclampsia | NA | 77 (22.85%) | 95 (17.27%) | 49 (12.96%) |
| Paternity Match | | | | |
| Yes | NA | NA | NA | NA |
| No | NA | NA | NA | NA |
| Unknown | NA | NA | NA | NA |
| N/A | NA | NA | NA | NA |
| Type of Pregnancy | | | | |
| Spontaneous | NA | NA | NA | NA |
| Assisted Reproductive Technology | NA | NA | NA | NA |
| Fetal Reduction | NA | NA | NA | NA |
| Vanishing Twin Syndrome | NA | NA | NA | NA |
| Medical History and Ongoing Conditions | | | | |
| Chronic Hypertension (CHTN) | NA | 147 (43.62%) | 151 (27.45%) | 118 (31.22%) |
| Gestational Hypertension (GHTN) | NA | NA | NA | NA |
| Diabetes | | | | |
| Type I | NA | 11 (3.27%) | 20 (3.64%) | 8 (2.12%) |
| Type II | NA | 41 (12.17%) | 35 (6.36%) | 22 (5.82%) |
| Gestational Diabetes | | | | |
| Type A1 | NA | NA | NA | NA |
| Type A2 | NA | NA | NA | NA |
| Smoker | | | | |
| Current | NA | NA | NA | NA |
| Past | NA | NA | NA | NA |
| Autoimmune Disease | NA | 12 (3.56%) | 26 (4.73%) | 12 (3.17%) |
| Nephropathy/ Kidney Disease | NA | 4 (1.19%) | 6 (1.09%) | 1 (0.26%) |
| Antiphospholipid Syndrome | NA | 0 (0.00%) | 2 (0.36%) | 1 (0.26%) |
| Cervical Dysplasia | NA | NA | NA | NA |
| Endometriosis | NA | NA | NA | NA |
| Labor and Delivery | | | | |
| Type of Labor | | | | |
| No labor | NA | NA | NA | NA |
| Spontaneous | NA | NA | NA | NA |
| Augmented | NA | NA | NA | NA |
| Induced | 3 (25.00%) | 105 (31.16%) | 194 (35.27%) | 175 (46.42%) |
| Mode of Delivery | | | | |
| Cesarean | 7 (58.33%) | 165 (48.96%) | 223 (40.55%) | 171 (45.24%) |
| Vaginal | 3 (25.00%) | 134 (39.77%) | 256 (46.54%) | 179 (47.48%) |
| NA | 2 (16.67%) | 38 (11.28%) | 71 (12.91%) | 28 (7.41%) |
| Birth Weight in Grams (median, IQR) | NA | NA | NA | NA |
| Size for Gestational Age | | | | |
| Small for GA (SGA) | NA | NA | NA | NA |
| Appropriate for GA (AGA) | NA | NA | NA | NA |
| Large for GA (LGA) | NA | NA | NA | NA |
| GA at Delivery (median, IQR) | 36.86 (1.71) | 38.29 (2.28) | 38.14 (2.28) | 38.71 (1.72) |
| Preterm (<37 weeks' GA) | 5 (41.67%) | 86 (25.52%) | 134 (24.36%) | 23 (6.08%) |
| Full-term (≥37 weeks' GA) | 5 (41.67%) | 238 (70.62%) | 399 (72.54%) | 348 (92.06%) |
| Missing | 2 (16.67%) | 13 (3.86%) | 17 (3.10%) | 7 (1.85%) |
| APGAR (median, IQR) | | | | |
| 1 min | NA | NA | NA | NA |
| 5 min | NA | NA | NA | NA |
| Intrauterine Fetal Demise (IUFD) | 0 (0.00%) | 4 (1.19%) | 3 (0.55%) | 0 (0.00%) |

PRO-104: Select samples from PRO-104 were used as positive controls to further develop the assay. Pregnant women who were 18 to 45 years of age with 32 weeks 0 days to 36 weeks and 6 days weeks of gestation age who presented at clinical sites with signs and symptoms of preeclampsia (based on new onset or worsening of symptoms including elevated blood pressure, proteinuria, edema amongst others) were eligible for participation in the PRO-104 study. Baseline procedures were performed, including collection of demographic, medical and obstetric histories, list of concomitant medications, weight, height, blood pressure, and other clinical information, as well as obtaining blood and urine samples for use in biomarker assays. Study subjects were followed by several study visits until the delivery visit.

Study subjects who were diagnosed with PreE, within the first 24 hours of enrollment were included in the POSITIVE CONTROL cohort.

Subjects who did not develop preeclampsia before or at delivery or subjects who were diagnosed with PreE after 24 h of enrollment were included in the NEGATIVE-PRE-E CONTROL (NonPreE) cohort. For all subjects, the time from baseline sampling (in days) to either delivery or loss to follow-up was recorded.

Delivery outcomes (maternal and neonatal clinical information) were collected on all subjects enrolled in the study. Additionally, if possible, during admission for delivery, blood and urine samples were collected for analysis at delivery.

Example 4. —Use of VEGF as an Additional Diagnostic Marker for Preeclampsia

PlGF-f, PlGF-d, sFlt are measured in serum samples from pregnant women. VEGF is additionally measured in the serum from pregnant women with high PlGF-d, and/or high sFlt. VEGF above 10 pgs/ml or 50 pgs/ml or 100 pgs/ml is indicative of a reduced risk of preeclampsia.

Figure 12:
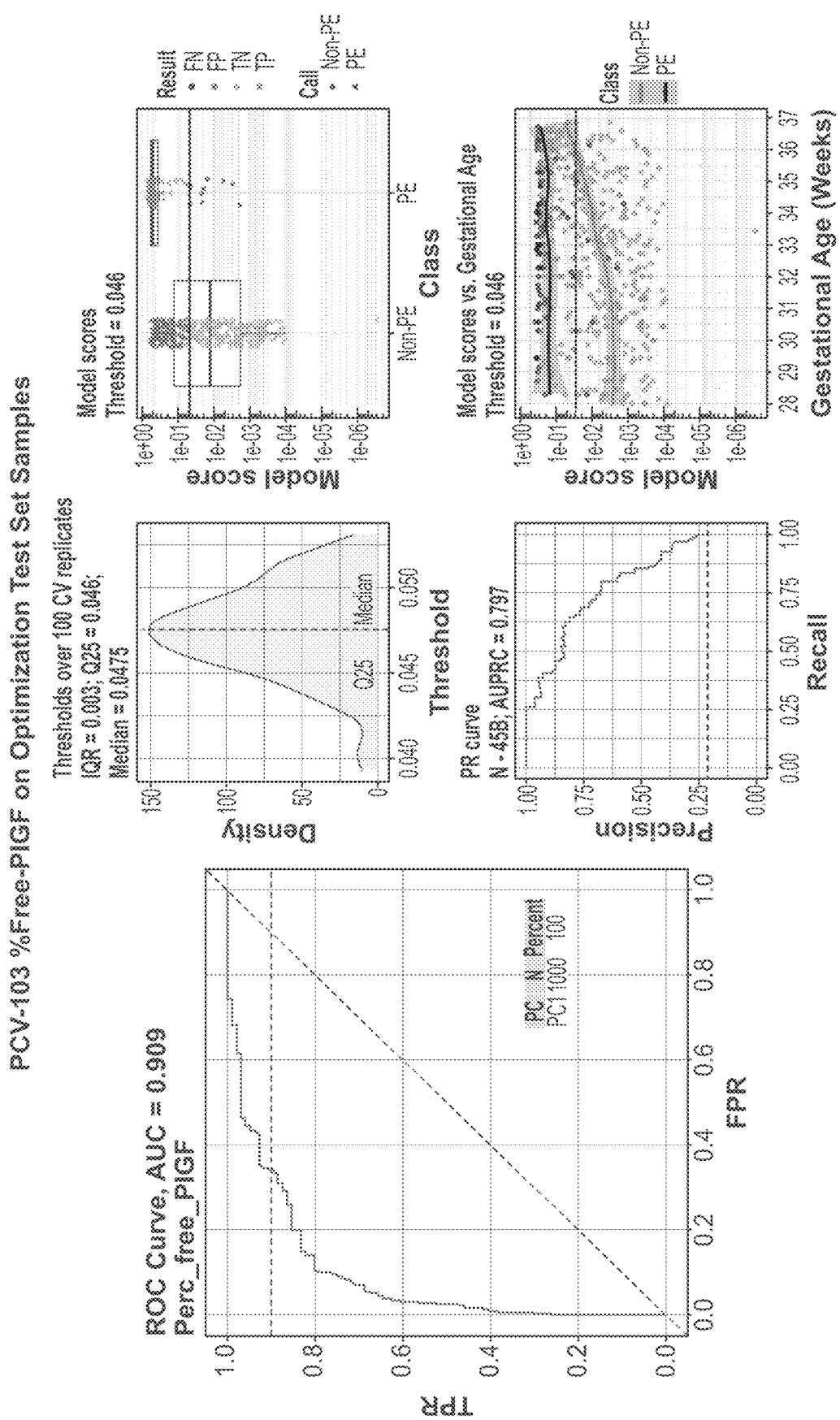
FIG. 12 shows an AUC analysis for a univariate model based on % free PlGF as described in Example 5.
Figure 13:
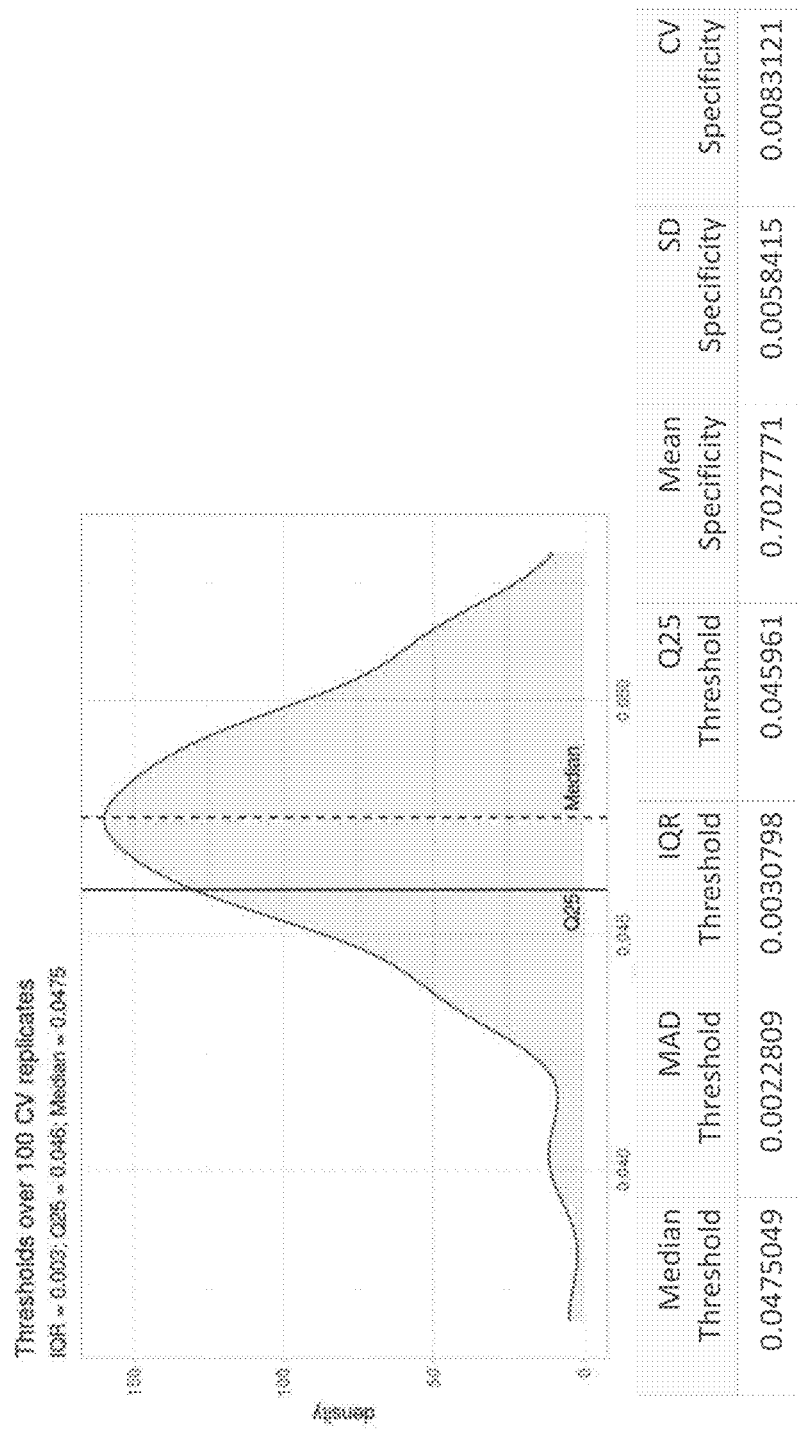
FIG. 13 depicts cutoff parameters for the univariate model based on % free PlGF as described in Example 5.
Figure 14:
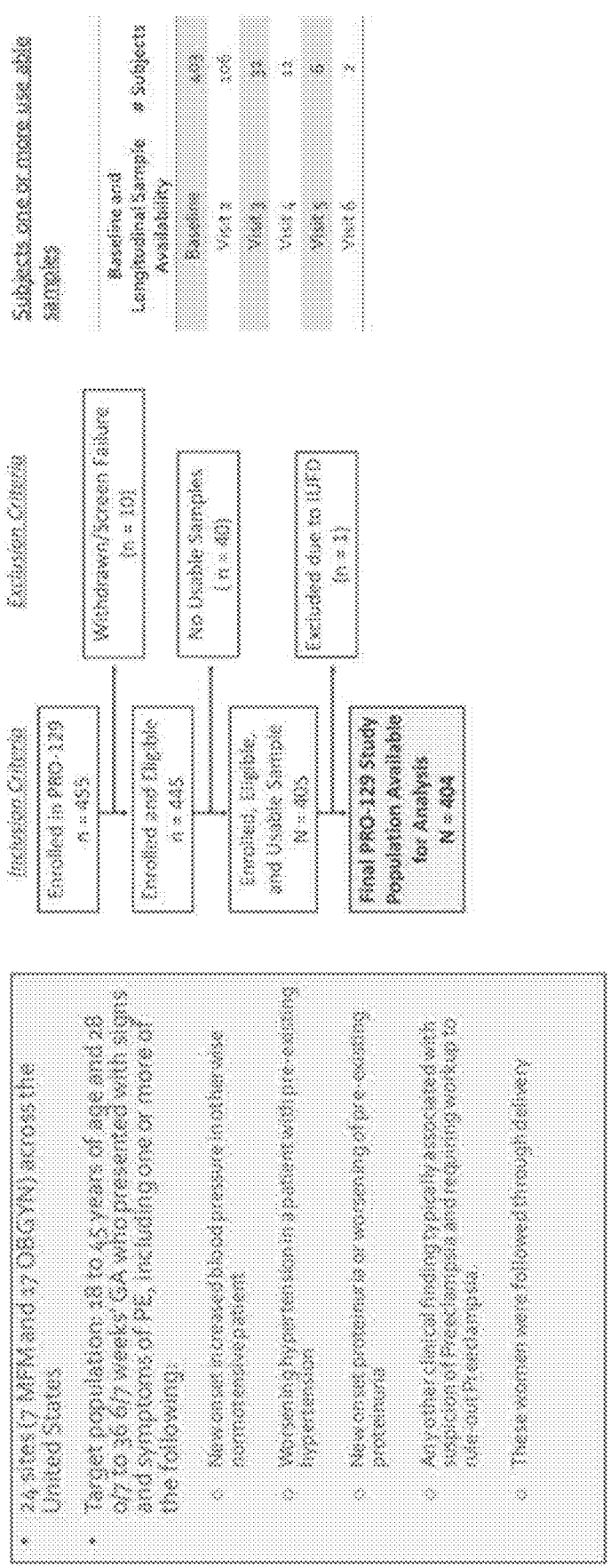
FIG. 14 depicts inclusion/exclusion criteria for the PRO-129 study used to validate the models and clinical profile/model combinations described herein.

Example 5. —Establishing Threshold for Test Using PlGF-d and PlGF-f in Detection of Preeclampsia or Absence Thereof Threshold analysis was performed to identify a threshold for a univariate model utilizing % $PlGF_{free}$ ($PlGF_{free}$/$PlGF_{dissociated}$) as a predictor of preeclampsia or absence thereof with a single cutoff using the $PlGF_{free}$/$PlGF_{dissociated}$ protocols described in Example 2 (in this model, % $PlGF_{free}$ levels higher than the threshold indicate preeclampsia). An AUC curve analysis of % $PlGF_{free}$ in the PRO-105 study populations from Example 3 were performed (see FIG. 12). 100 repeats of 10-fold cross-validation on the data from the study population was used to identify a threshold that achieved 90% sensitivity on the study population; the threshold was set at the $25^{th}$ percentile of the 100 repeats of 10-fold cross validation. The $25^{th}$ percentile threshold (Q25 Threshold) was determined to be 0.046; this threshold alongside other threshold distribution data is summarized below and in FIG. 13:

| Median Threshold | MAD Threshold | IQR Threshold | Q25 Threshold | Mean Specificity | SD Specificity | CV Specificity |
|---|---|---|---|---|---|---|
| 0.0475049 | 0.0022809 | 0.0030798 | 0.045961 | 0.7027771 | 0.0058415 | 0.0083121 |

Surprisingly, this model utilizing both PlGF-d and PlGF-f exhibited high performance in terms of NPV.

Next, with this model locked at the defined Q25 threshold, the performance of the model was tested in a forward-looking analysis in a new study cohort recruited and designated PRO-129. The target population for the study was pregnant women 18 to 45 years of age and 28 to 36 6/7 weeks gestational age who presented with signs and symptoms of PE, including one or more of: (i) new onset increased blood pressure in an otherwise normotensive patient; (ii) worsening hypertension in a patient with pre-existing hypertension; (iii) new onset proteinuria or worsening of pre-existing proteinuria; (iv) any other clinical finding typically associated with suspicion of preeclampsia and requiring workup to rule-out preeclampsia. The study demographics are presented below in Table B.

TABLE B

Demographic and Clinical Variables for PRO-129 Study

| | Gestation at Enrollment (weeks, days) | |
|---|---|---|
| Demographic and Clinical Variables | <35 0/7 (n = 269) | 35 0/7 to 36 6/7 (n = 135) |
| Demographic | n (%) | |
| Maternal Age (median, IQR) | 30 (8.00) | 30 (10.00) |
| under 25 | 50 (18.59%) | 27 (20.00%) |
| 25 to 29 | 78 (29.00%) | 37 (27.41%) |
| 30 to 34 | 80 (29.74%) | 36 (26.67%) |
| 35 to 39 | 47 (17.47%) | 25 (18.52%) |
| 40 to 45 | 14 (5.20%) | 10 (7.41%) |
| BMI (mean, SD) | 35.16 (10.90) | 34.75 (9.32) |
| Underweight (<18.5) | 0 (0.00%) | 0 (0.00%) |
| Normal (18.5 through 24 BMI) | 11 (4.09%) | 7 (5.19%) |
| Overweight (25 through 29 BMI) | 51 (18.96%) | 27 (20.00%) |
| Obese-class 1 (30 through 34 BMI) | 70 (26.02%) | 36 (26.67%) |
| Obese-class 2 (35 through 39 BMI) | 59 (21.93%) | 32 (23.70%) |

With this model locked at the defined Q25 threshold, the performance of the model was tested in a cross-sectional analysis on the PRO-105 study population, segregating the samples from the study into either "positive Pre-E controls" or "non-cases" as illustrated in FIG. 15A.

The performance parameters for this univariate model-based analysis applying the Q25 threshold for a cross-sectional analysis are displayed in Table 1A below:

| N | TP | TN | FP | FN | Sensitivity | Specificity | Prevalence | PPV | NPV |
|---|---|---|---|---|---|---|---|---|---|
| 458 | 86 | 238 | 124 | 10 | 89.6 [82.9-94.2] | 65.8 [60.7-70.4] | 10% | 22.5 [17.4-28.6] | 98.3 [95.8-99.3] |

TABLE B-continued

Demographic and Clinical Variables for PRO-129 Study

| Demographic and Clinical Variables Demographic | Gestation at Enrollment (weeks, days) | |
|---|---|---|
| | <35 0/7 (n = 269) | 35 0/7 to 36 6/7 (n = 135) |
| | n (%) | |
| Obese-class 3 (40 or greater BMI) | 77 (28.62%) | 33 (24.44%) |
| Missing | 1 (0.37%) | 0 (0.00%) |
| Race | | |
| American Indian or Alaskan Native | 2 (0.74%) | 1 (0.74%) |
| Asian | 12 (4.46%) | 3 (2.22%) |
| Black or African American | 42 (15.61%) | 18 (13.33%) |
| Native Hawaiian or Other Pacific Islander | 0 (0.00%) | 0 (0.00%) |
| White | 182 (67.66%) | 100 (74.07%) |
| Two or more races | 6 (2.23%) | 0 (0.00%) |
| Unknown | 22 (8.18%) | 13 (9.63%) |
| Refused | 3 (1.12%) | 0 (0.00%) |
| Ethnicity | | |
| Hispanic or Latino | 5 (20.45%) | 35 (25.93%) |
| Not Hispanic or Latino | 200 (74.35%) | 94 (69.63%) |
| Unknown/Not Provided | 14 (5.20%) | 6 (4.44%) |
| Pregnancy History | | |
| Gestational Age (GA) at Enrollment (median, IQR) | 32.14 (3.28) | 36 (1.00) |
| 28 0/7 to 28 6/7 | 32 (11.90%) | 0 (0.00%) |
| 29 0/7 to 29 6/7 | 18 (6.69%) | 0 (0.00%) |
| 30 0/7 to 30 6/7 | 31 (11.52%) | 0 (0.00%) |
| 31 0/7 to 31 6/7 | 43 (15.99%) | 0 (0.00%) |
| 32 0/7 to 32 6/7 | 45 (16.73%) | 0 (0.00%) |
| 33 0/7 to 33 6/7 | 46 (17.10%) | 0 (0.00%) |
| 34 0/7 to 34 6/7 | 54 (20.07%) | 0 (0.00%) |
| 35 0/7 to 35 6/7 | 0 (0.00%) | 59 (43.70%) |
| 36 0/7 to 36 6/7 | 0 (0.00%) | 76 (56.30%) |
| Gravidity (median, IQR) | 2 (3) | 2 (2) |
| 1 | 71 (26.39%) | 39 (28.89%) |
| >1 | 198 (73.61%) | 96 (71.11%) |
| # of births (median, IQR) | 1 (2) | 1 (1) |
| Nulliparous (0) | 93 (34.57%) | 60 (44.44%) |
| >0 | 176 (65.43%) | 75 (55.56%) |
| History of Previous Preeclampsia | 47 (17.47%) | 22 (16.30%) |
| Chronic Hypertension (CHTN) | 53 (19.70%) | 20 (14.81%) |
| Gestational Hypertension (GHTN) | 98 (36.43%) | 52 (38.52%) |
| Diabetes | | |
| Type I | 3 (1.12%) | 1 (0.74%) |
| Type II | 18 (6.69%) | 10 (7.41%) |
| Gestational Diabetes | | |
| Type A1 | 19 (7.06%) | 6 (4.44%) |
| Type A2 | 23 (8.55%) | 16 (11.85%) |
| Smoker | | |
| Current | 12 (4.46%) | 3 (2.22%) |
| Past | 39 (14.50%) | 15 (11.11%) |
| Nephropathy/Kidney Disease | 4 (1.49%) | 1 (0.74%) |
| Antiphospholipid Syndrome | 0 (0.00%) | 0 (0.00%) |
| Cancer | | |
| Lumpectomy | 1 (0.37%) | 0 (0.00%) |
| Melanoma | 0 (0.00%) | 1 (0.74%) |
| Thyroid Cancer | 2 (0.074%) | 0 (0.00%) |
| Cervical Dysplasia | 3 (1.12%) | 1 (0.74%) |
| Endometriosis | 5 (1.86%) | 0 (0.00%) |
| Focal Segmental Glomerulosclerosis | 1 (0.37%) | 0 (0.00%) |
| Labor and Delivery | | |
| Type of Labor | | |
| No labor | 94 (34.94%) | 28 (20.74%) |
| Spontaneous | 64 (23.79%) | 27 (20.00%) |
| Augmented | 5 (1.86%) | 12 (8.89%) |
| Induced | 106 (39.41%) | 68 (50.37%) |
| Mode of Delivery | | |
| Cesarean | 143 (53.16%) | 53 (39.26%) |
| Vaginal | 126 (46.84%) | 82 (60.74%) |
| Birth Weight in Grams (median, IQR) | 3130 (862) | 3138.5 (730) |
| Size for Gestational Age | | |
| Small for GA (SGA) | | |
| Appropriate for GA (AGA) | | |
| Large for GA (LGA) | | |
| GA at Delivery (median, IQR) | 37.71 (2.57) | 37.86 (2.00) |
| Preterm (<37 weeks' GA) | 78 (29.00%) | 24 (17.78%) |
| Full-term (≥37 weeks' GA) | 191 (71.00%) | 111 (82.22%) |
| APGAR (median, IQR) | | |
| 1 min | 8 (1) | 8 (1) |
| 5 min | 9 (0) | 9 (0) |
| Intrauterine Fetal Demise (IUFD) | 0 (0.00%) | 0 (0.00%) |

Figure 15B:
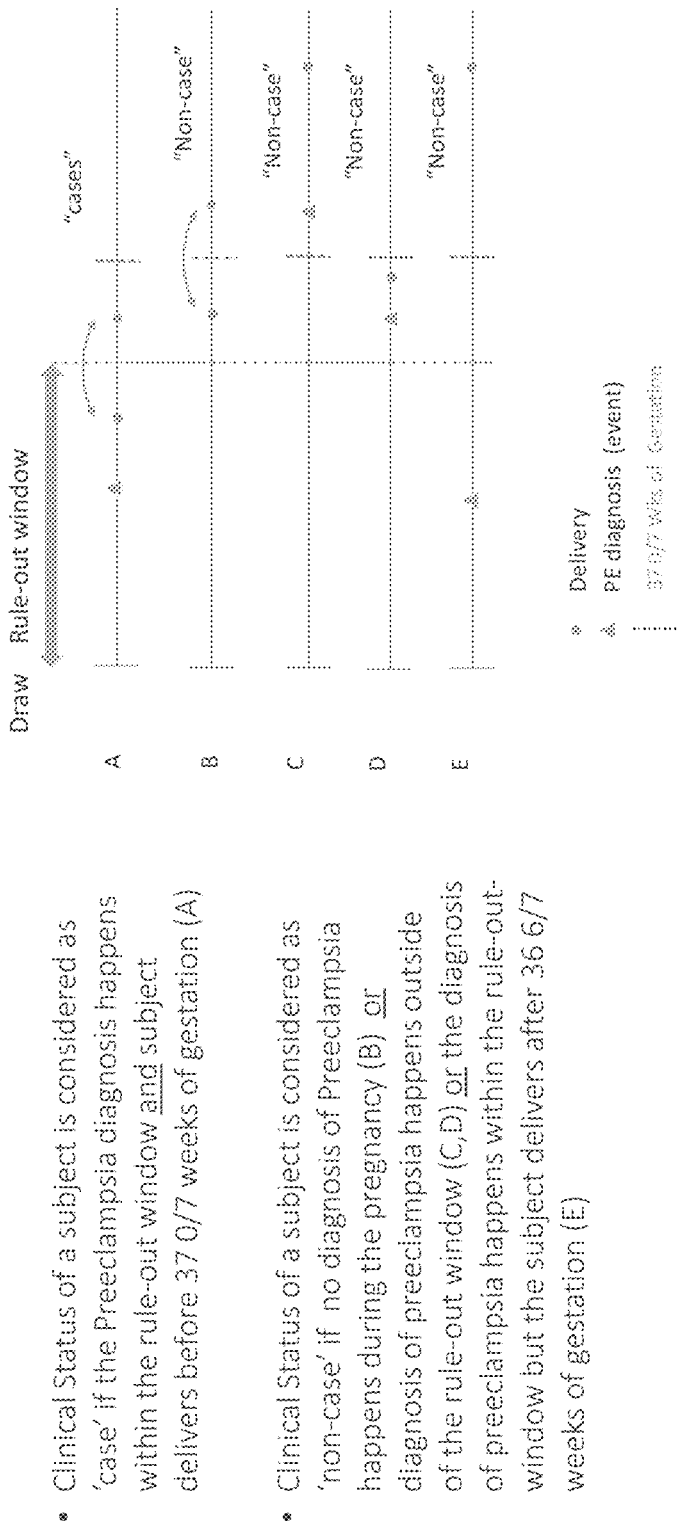

As part of this forward-looking rule out analysis, the samples from the PRO-129 study were re-segregated into either "cases" or "non-cases" as shown in FIG. 15B. As part of this scheme, the clinical status of a subject is considered "case" if the preeclampsia diagnosis happens within the rule-out window and subject delivers before 37 0/7 weeks of gestation, and the clinical status of a subject is considered as 'non-case' if no diagnosis of Preeclampsia happens during the pregnancy or diagnosis of preeclampsia happens outside of the rule-out window or the diagnosis of preeclampsia happens within the rule-out-window but the subject delivers after 36 6/7 weeks of gestation As part of this forward-looking rule out analysis, the same % $PLGF_{free}$-based univariate model above with the Q25 threshold locked was used to rule-out preeclampsia when the % $PLGF_{free}$ value was below the threshold. The performance parameters for this univariate model-based analysis applying a "rule out" window of 14 days based on the Q25 threshold are described in Table 1B below:

TABLE 1B

Performance Of % PLGF$_{free}$ Model For Ruling Out Preeclampsia Over A Window Of 14 Days

| N | TP | TN | FP | FN | Sensitivity | Specificity | Prevalence | PPV | NPV |
|---|---|---|---|---|---|---|---|---|---|
| 350 | 44 | 179 | 121 | 6 | 88.0 [76.2-94.4] | 59.7 [54.0-65.1] | 10% | 19.5 [14.2-26.2] | 97.8 [94.5-99.1] |

Surprisingly, this model utilizing both PlGF-d and PlGF-f exhibited high performance even at a relatively stringent task—ruling out future preeclampsia in patients over a window of 14 days.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining levels of free and dissociated PlGF in a biological sample from a pregnant human female subject, the method comprising:
   (a) determining an amount of PlGF-f in the biological sample;
   (b) applying a treatment to the biological sample to dissociate PlGF complexes; and
   (c) determining an amount of PlGF-d in the biological sample.

2. The method of claim 1, further comprising obtaining the biological sample prior to (a).

3. The method of claim 1, further comprising determining an amount of at least sFLT.

4. The method of claim 1, further comprising determining an amount of Endoglin in the biological sample.

5. The method of claim 1, further comprising determining an amount of KIM-1 in the biological sample.

6. The method of claim 1, further comprising determining an amount of CD274 in the biological sample.

7. The method of claim 1, further comprising determining an amount of FGF21 in the biological sample.

8. The method of claim 1, wherein the treatment comprises contacting the biological sample with an agent that prevents PlGF from assembling into a PlGF complex or disables PlGF from a PlGF:sFLT1 complex.

9. The method of claim 8, wherein the agent is selected from: a surfactant, a detergent, a chaotropic agent, a PlGF-binding protein, and an s-FLT-binding protein.

10. The method of claim 1, wherein the amount of PlGF-f, PlGF-d, or both is determined by an immunoassay.

11. The method of claim 10, wherein the immunoassay is selected from a capture ELISA, an indirect ELISA, a TR-FRET assay, a proximity extension assay, an amplified luminescent proximity (LOCI) assay, an electrochemiluminescence immunoassay, a luminescent oxygen channeling assay, or a lateral flow assay.

12. The method of claim 1, wherein (a) or (c) involve contacting the biological sample with a capture reagent.

13. The method of claim 12, wherein the capture agent comprises an aptamer or an antibody or an antigen-binding fragment thereof.

14. The method of claim 1, wherein the biological sample is serum or plasma.

15. The method of claim 1, wherein the amount of PlGF-f and the amount of PlGF-d are determined using same reagents.

16. The method of claim 1, wherein the pregnant human female has been pregnant for at least 20 weeks.

17. The method of claim 1, wherein the pregnant human female has been pregnant for no more than 30 weeks.

18. The method of claim 1, wherein determining the amount of PLGF-d in the biological sample comprises determining a total amount of PLGF in the biological sample.

* * * * *